(12) United States Patent
Berckmans et al.

(10) Patent No.: US 10,076,273 B2
(45) Date of Patent: Sep. 18, 2018

(54) REAL-TIME MONITORING AND CONTROL OF PHYSICAL AND AROUSAL STATUS OF INDIVIDUAL ORGANISMS

(75) Inventors: Daniel Berckmans, Kessel-Lo (BE); Stijn Quanten, Hasselt (BE); Jean-Marie Aerts, Haasrode (BE)

(73) Assignee: BIORICS NV, Leuven (BE)

( * ) Notice: Subject to any disclaimer, the term of this patent is extended or adjusted under 35 U.S.C. 154(b) by 387 days.

(21) Appl. No.: 12/307,602

(22) PCT Filed: Jul. 6, 2007

(86) PCT No.: PCT/BE2007/000075
§ 371 (c)(1),
(2), (4) Date: Jan. 6, 2009

(87) PCT Pub. No.: WO2008/003148
PCT Pub. Date: Jan. 10, 2008

(65) Prior Publication Data
US 2009/0312998 A1    Dec. 17, 2009

(30) Foreign Application Priority Data

Jul. 6, 2006  (GB) .................................. 0613446.4
Jul. 7, 2006  (GB) .................................. 0613523.0

(51) Int. Cl.
*A61B 5/16*       (2006.01)
*A61B 5/024*      (2006.01)
(Continued)

(52) U.S. Cl.
CPC .............. *A61B 5/165* (2013.01); *A61B 5/024* (2013.01); *A61B 5/1118* (2013.01); *G16H 50/50* (2018.01); *G06F 19/3481* (2013.01)

(58) Field of Classification Search
None
See application file for complete search history.

(56) References Cited

U.S. PATENT DOCUMENTS 6,030,342 A  *  2/2000  Amano et al. ................ 600/301
6,104,947 A  *  8/2000  Heikkila et al. .............. 600/519
(Continued)

FOREIGN PATENT DOCUMENTS

WO    WO 02/098213 A2    12/2002
WO    WO 04/032719 A2     4/2004
WO    WO 06/009830 A2     1/2006

OTHER PUBLICATIONS

Gentilini, A. et al. Multitasked closed-loop control in anesthesia. IEEE Engineering in Medicine and Biology Magazine 20, 39-53 (2001).*

(Continued)

*Primary Examiner* — Soren Harward
(74) *Attorney, Agent, or Firm* — Browdy and Neimark, PLLC

(57) ABSTRACT

The present invention relates to methods and systems for monitoring and controlling the status of humans or animals, in particular relating to both the physical and the arousal status of an individual human or animal. These methods and systems rely on a dynamic and adaptive data-based on-line modelling technique wherein information on bioprocess inputs and outputs is measured in real-time and the model predicts an output based on the bioprocess input. The provided methods are particularly useful to monitor and/or control processes in which performance is important.

34 Claims, 41 Drawing Sheets

(51) Int. Cl.
*A61B 5/11* (2006.01)
*G16H 50/50* (2018.01)
*G06F 19/00* (2018.01)

(56) References Cited

U.S. PATENT DOCUMENTS

| | | | |
|---|---|---|---|
| 7,027,621 | B1 | 4/2006 | Prokoski et al. |
| 2004/0152957 | A1* | 8/2004 | Stivoric et al. ............... 600/300 |
| 2004/0199275 | A1 | 10/2004 | Berckmans et al. |
| 2005/0217674 | A1 | 10/2005 | Burton et al. |

OTHER PUBLICATIONS

Knopp, W. D., Wang, T. W. & Bach, B. R. Ergogenic drugs in sports. Clinics in Sports Medicine 16, 375-392 (1997).*
Ravussin, E., Lillioja, S., Anderson, T. E., Christin, L. & Bogardus, C. Determinants of 24-hour energy expenditure in man. methods and results using a respiratory chamber. The Journal of clinical investigation 78, 1568-1578 (1986).*
Ravussin, E. & Bogardus, C. A brief overview of human energy metabolism and its relationship to essential obesity. American Journal of Clinical Nutrition 55, 242S-245S (1992).*
Seematter, G. et al. Effects of mental stress on insulin-mediated glucose metabolism and energy expenditure in lean and obese women. Am J Physiol Endocrinol Metab 279, E799-805 (2000).*
Quanten, S., de Valck, E., Cluydts, R., Aerts, J.-M. & Berckmans, D. Individualized and time-variant model for the functional link between thermoregulation and sleep onset. Journal of Sleep Research 15, 183-198 (2006).*
Young, P. Stochastic, Dynamic Modelling and Signal Processing: Time Variable and State Dependent Parameter Estimation. In Nonlinear and Nonstationary Signal Processing (ed. Fitzgerald, W. J.) 74-114 (Cambridge University Press, 2000).*
Young, P. & Chotai, A. Data-based mechanistic modeling, forecasting, and control. IEEE Control Systems Magazine 21, 14-27 (2001).*
International Preliminary Report on Patentability (PCT/BE2007/000075) dated Oct. 17, 2008.
International Search Report (PCT/BE2007/000075) dated Nov. 14, 2007.
Written Opinion of the International Searching Authority (PCT/BE2007/000075) dated Nov. 14, 2007.
Response to the Written Opinion of the International Searching Authority (PCT/BE2007/000075) dated May 6, 2008.
Office Action for Australian Patent Application No. 2007271741, dated Jul. 14, 2011.
Patent Examination Report No. 2 issued in Australian Patent Application No. 2007271741, dated Jul. 17, 2012 (4 pages).
Jos F. Brosschot et al., "Heart rate response is longer after negative emotions than after positive emotions", International Journal of Psychophysiology, vol. 50, No. 3, Nov. 1, 2003, pp. 181-187.
G. B. Moody, "ECG-based indices of physical activity", Computers in Cardiology 1992, Proceedings of Durham, NC, USA 11-14 Oct. 1, Los Alamitos, CA, USA,IEEE Comput. Soc, US, Oct. 11, 1992, pp. 403-406.
Michael Myrtek et al., "Stress and strain of blue and white collar workers during work and leisure time: results of psychophysiological and behavioral monitoring", Applied Ergonomics., vol. 30, No. 4, Aug. 1, 1999, pp. 341-351.

* cited by examiner

General Schedule

Compare dynamic parameters to pre-learned bounding box

⇒ Result: *1* if behaviour occurs, *0* else

REAL-TIME MONITORING AND CONTROL OF PHYSICAL AND AROUSAL STATUS OF INDIVIDUAL ORGANISMS

CROSS-REFERENCE TO RELATED APPLICATIONS

This application is the U.S. National Stage of International Application No. PCT/BE2007/000075, filed Jul. 6, 2007, which, in turn, claims the benefit of British Patent Application Nos. GB 0613446.4, filed Jul. 6, 2006 and GB 0613523.0, filed Jul. 7, 2006.

FIELD OF THE INVENTION

The present invention relates to a method and a system for monitoring and controlling the status of humans or animals, in particular relating to the arousal of an individual human or animal. The provided methods are thus particularly useful to monitor and/or control processes in which performance is important. The present invention also provides software and computer program products for executing the methods of the invention.

BACKGROUND OF THE INVENTION

For many processes and activities, it would be useful to be able to efficiently monitor, predict or control the status of the organisms taking part in these processes or activities. This applies particularly to processes involving physical activity or where metabolic energy is produced by the body, and thus to organisms capable of physical activity or producing metabolic energy such as humans or animals. One way to monitor and manage bioprocesses of living organisms is through systems biology. To gain more insight in the functioning of biological systems and the responses of the living organisms to those systems, purely experimental deduction will not suffice because of the intrinsic complexity of biological systems (Kitano, 2002). However, the combination of engineering system identification theory and experimental biology—called systems biology—offers great perspectives. Systems biology advocates decompositions of complex biological systems in several subsystems according to traditional engineering (e.g. McAdams et. al, 1995; Hartwell et. al, 1999) and engineering control theory (e.g. Csete et. al, 2002).

The basic idea behind systems biology is to identify a mathematical model of the system and then use this model to control or to design a controller so that the behaviour of the system will follow a desired profile (e.g. Tomlin et. al, 2005). The most commonly used control processes are feedback connections. However the essential part of an efficient control is the prediction of how the so-called considered process output will dynamically respond to the variation of a system input. Consider for example a driver who is driving a car (see FIG. 1). A possible process output is the driving direction of the car and another possible process output is the position of the steering wheel. First the driver will at every moment use the principle of continuous feedback by visually comparing the actual driving direction with the desired one and use the difference to control the position of the steering wheel. The feedback however is a necessary but not a sufficient condition for efficient process control. If feedback would be enough for an efficient control, then everybody could drive a car, or sail a boat, or skate a skateboard which obviously is not the case. An efficient control needs at every moment a good prediction of how the process output will dynamically respond to a variation of the process input. This is what a driver is doing when driving a car, this is why a skater can skate, as he knows how the skateboard will respond to a variation of the control input. If an engineer would design an autopilot function for driving a car (FIG. 1) than he first would design a mathematical model of the vehicle dynamics, which describes how the driving direction of the car (output) changes when turning the steering wheel (input). By using sensors to measure the output continuously, the engineer uses the model to calculate how these measurements should be employed to adjust the inputs automatically, so that if the car does not follow the desired driving direction, it is quickly and smoothly guided back to the desired driving track (after Berckmans and De Moor, 1996).

Thus, by applying the modern control theory with model based control techniques, (bio)processes can be monitored and controlled (Golten and Verwer, 1991; Camacho and Bordons, 1999). This requires at every moment the availability of a process model that allows predicting the dynamic response of the process output to a variation of one or more process inputs.

Many different models have been described in the art. A first category are mechanistic models. These describe the dynamic response based on physical, physiological and biochemical laws, resulting in complex models, consisting of many equations and model parameters. Such models are suitable for gaining insight, transfer of scientific knowledge and for simulation of processes, but a practical drawback is that they are too complex and too inaccurate for control purposes in practice.

Beside mechanistic models, also empirical (non-linear) models are found in literature. These models are mainly the result of a non-linear regression analysis applied to data from a human or animal. The advantages of such models are that they are accurate and have not such a complex structure. However, the models are estimated off-line (after all the data are gathered). Since these models are not updated in real time and not all relevant process inputs or disturbing factors are taken into account, these known models are also less useful for monitoring or control purposes.

Ideally, monitoring and controlling bio-response of living organisms should be done by using less complex models and modelling techniques to model the dynamic response of a bioprocess output to a variation of one or more process inputs, or to a variation in one or more disturbing variables that influence the process outputs. For application of the modelling approach to living organisms such a process model should be simple and compact so that it can be applied in real time to be accurate. To be applicable on living organisms, such a model should overcome three problems often encountered in the prior art.

A first important consideration that needs to be made is that a living organism is a very complex system. Today it is for example not possible to write down all dynamic biochemical and biological processes that occur in a single cell of a human, animal or plant. E.g. the process of infection is not analyzed or understood to that level since it is so complex.

Secondly, a living organism (be it human, animal or plant) is not responding or behaving like the average of a population. The subjects to be monitored have thus far been regarded as the average of a population, but not as an individual living organism. For instance, the training of athletes or the handling of animals is done by considering the living organism as the average of a population. Existing equipment (e.g. commercially available heart rate monitors)

is based on statistical relationships taken from a population of many individuals, the amount and concentration of medication in the whole health care systems is not individualized, research about sports training is based on statistical curves measured on many different athletes. In reality however no living organism is acting or behaving as an average of a population, but instead as an individual.

Each living organism is individually different. Unlike mechanical objects that can be produced in a very accurate and identical way, individual living organisms differ in many ways from each other and also behave in an individual way.

Thirdly, an individual living organism is not always responding to process inputs or environmental variables (physical environment, stress, medication, food, etc.) in an identical way. Thus, all biological responses or behaviour in a same individual can be time varying. The way individuals fall asleep for example can differ from one time to another. One moment, they are concentrated and the next moment this might be totally different. Living organisms are not responding dynamically in a standard way: they are time-varying systems. A living organism is responding in a dynamic way (i.e. biological responses or bioresponses) to variations of most environmental variables but can show spontaneous biological behaviour as well. Living organisms also are dynamic systems: they respond and behave in a dynamic way.

Looking to these higher mentioned most important characteristics in relation to the monitoring and controlling of the status of living organisms it can be stated that living organisms are Complex, Individual, Time varying and Dynamic ("CITD") systems.

The final problem relates to the monitoring and controlling of these CITD systems. Most existing monitoring techniques or controlling tools are not developed for CITD systems. For instance, a calibration curve of a sensor assumes that the individual differences of the sensors will be small enough to guarantee a high accuracy. However, for living organisms (i.e. CITD systems) this does not work since none of them is acting as the theoretical average of a population. One approach to circumvent this problem is by taking many more samples, like in neural networks for classification. However, for CITD systems this means that the solution never can be more accurate than the standard deviation around the theoretical average and for living organisms this ends up in a high error for each individual at a given moment.

This problem has been solved previously, as described in European patent EP1392109. A method is described to monitor and control individual living organisms as CITD systems. The mathematical model underlying this method is a dynamic and adaptive data-based on-line modelling technique, which manages to model accurately the CITD systems using only a limited number of parameters. Although the exemplified embodiments mainly relate to monitoring biomass production in different animals, the methods are applicable in many other situations. Indeed, it is made clear that any bioresponse can be monitored based on the appropriate real-time information on bioprocess inputs and outputs. This applies to humans, animals, as well as plants.

Although the method proposed in EP1392109 can be used to adequately monitor and control almost all bioprocesses, there are some embodiments where this method can be made more efficient. This specifically applies to circumstances in which the relationship between bioprocess inputs and outputs involves factors other than those directly related to mechanical activity or basal metabolism, e.g. because of the involvement of mental or emotional processes, arousal, stress, fear or the like. Up till now, these components could not be adequately described and thus not be used as an input or output to the model.

Nevertheless, it is well recognized that there is a link between the mental/emotional/psychological/psychophysiological/cognitive or general arousal status of an individual (human or animal) and performance of a task.

The classic description of the relationship between arousal and performance is the Yerkes-Dodson law (Yerkes and Dodson, 1908). This empirically based law, which was originally demonstrated using mice, dictates that performance increases with cognitive arousal, but only to a certain point: when levels of arousal become too high, performance will decrease. A corollary is that there is an optimal level of arousal for a given task. The process is often demonstrated graphically as an inverted U-shaped curve (FIG. 2), increasing and then decreasing with higher levels of arousal. It has been proposed that different tasks may require different levels of arousal. For example, difficult or intellectually demanding tasks may require a lower level of arousal for optimal performance (to facilitate concentration), whereas tasks demanding stamina or persistence may be performed better with higher levels of arousal (to increase motivation). The effect of the difficulty of tasks later on led to the hypothesis that the Yerkes-Dodson Law can be decomposed into two distinct factors. The upward part of the converted U can be thought of as the energizing effect of arousal. The downward part on the other hand is caused by negative effects of arousal (or stress) on cognitive processes, like attention ("tunnel vision"), memory, and problem-solving.

This principle is central to the science of psychophysiology. Psychophysiology studies interactions between the mind and body by recording how the body is functioning and relating the functions recorded to behaviour. Changes in the body's functioning cause changes in behaviour and vice versa. Psychophysiological recording techniques are generally non-invasive. That is, they record from the body's surface and nothing goes into the person being recorded. Psychophysiological recordings are frequently used to help assess problems with how the body is functioning.

Psychophysiology is the science of understanding the link between psychology and physiology. Psychophysiology is different from physiological psychology in that psychophysiology looks at the way psychological activities produce physiological responses, while physiological psychology looks at the physiological mechanisms which lead to psychological activity. Historically, most psychophysiologists tended to examine the physiological responses and organ systems innervated by the autonomic nervous system. More recently, psychophysiologists have been equally, or potentially more, interested in the central nervous system, exploring cortical brain potentials such as the many types of event related potentials (ERPs), brain waves, functional neuroimagery (fMRI), PET, MEG, etc.

A psychophysiologist may look at how exposure to a stressful or physiological arousing situation will produce a result in physiological variables such as the cardiovascular system (a change in heart rate (HR), vasodilation/vasoconstriction, myocardial contractility, or stroke volume). To control these psychophysiological events, biofeedback is often used.

With biofeedback is meant providing real time information from psychophysiological recordings about the levels at which physiological systems are functioning. Biofeedback does not need to involve the use of computers, electronic devices etc. For example, a mirror is a perfectly good biofeedback device for many aspects of gait retraining.

Electronic biofeedback devices are designed to record physiological functions non-invasively. Most record from the surface of the skin. The information recorded by surface sensors is frequently sent to a computer for processing and then displayed on the monitor and/or through speakers. The individual being recorded and any therapist or coach who may be present can attend to the display of information and incorporate it into what ever process they are attempting to perform.

The basic principles of biofeedback have been demonstrated while doing animal experimentation conditioning the behaviour of rats. It was found that, by stimulating the pleasure centre of a rat's brain with electricity; it was possible to train them to control phenomena ranging from their heart rates to their brainwaves. Until that point, it was believed that bodily processes such as heart rate were under the control of the autonomic nervous system and not responsive to conscious effort.

The phenomenon of biofeedback is believed to work as follows: stressful or physiological arousing events produce strong emotions or mental processes, which in turn lead to certain physiological responses. Many of these responses are controlled by the sympathetic nervous system, the network of nerve tissues that helps prepare the body to meet emergencies by preparing the typical "flight or fight" response.

The typical pattern of response to emergencies probably emerged during the time when all humans faced mostly physical threats. Although the "threats" we now live with are seldom physical, the body reacts as if they were: The pupils dilate to let in more light. Sweat pours out, reducing the chance of skin cuts. Blood vessels near the skin contract to reduce bleeding, while those in the brain and muscles dilate to increase the oxygen supply. The gastrointestinal tract, including the stomach and intestines, slows down to reduce the energy expensed in digestion. The heart beats faster, and blood pressure rises. Normally, people calm down when a stressful or physiological arousing event is over especially if they have done something to cope with it. For instance, when someone is walking down a dark street and hears someone running towards him, he typically will get aroused, i.e. his body will prepare him to ward off an attacker or run fast enough to get away. When the potentially threatening situation is over, he gradually relaxes.

If someone gets angry at his boss, it's a different matter. His body may prepare to fight. But in order not to lose his job, he will try to ignore the angry feelings. Similarly, if an individual gets stalled in traffic, there's nothing he can do to get away. These situations can literally make someone sick. Their body has prepared for action, but they cannot act. Individuals differ in the way they respond to stress or arousal. In some, one function, such as blood pressure, becomes more active while others remain normal. Many experts believe that these individual physical responses to stress or arousal can become habitual. When the body is repeatedly aroused, one or more functions may become permanently overactive. Actual damage to bodily tissues may eventually result.

Biofeedback is often aimed at changing habitual reactions to stress that can cause pain or disease. Many clinicians believe that some of their patients and clients have forgotten how to relax. Feedback of physical responses such as skin temperature and muscle tension provides information to help patients recognize a relaxed state. The feedback signal may also act as a kind of reward for reducing tension.

The value of a feedback signal as information and reward may be even greater in the treatment of patients with paralyzed or spastic muscles. With these patients, biofeedback seems to be primarily a form of skill training like learning to pitch a ball. Instead of watching the ball, the patient watches the machine, which monitors activity in the affected muscle. Stroke victims with paralyzed arms and legs, for example, see that some part of their affected limbs remains active. The signal from the biofeedback machine proves it. This signal can guide the exercises that help patients regain use of their limbs. Perhaps just as important, the feedback convinces patients that the limbs are still alive. This reassurance often encourages them to continue their efforts.

Clinical biofeedback techniques that grew out of the early laboratory procedures are now widely used to treat an ever-lengthening list of conditions. These include amongst others migraine, headaches, tension headaches, and many other types of pain, disorders of the digestive system, high blood pressure and its opposite, low blood pressure, irregular heartbeats or cardiac arrhythmias (abnormalities, sometimes dangerous, in the rhythm of the heartbeat), Raynaud's disease (a circulatory disorder that causes uncomfortably cold hands), epilepsy, paralysis and other movement disorders, asthma, irritable bowel syndrome, hot flashes, nausea and vomiting associated with chemotherapy, and incontinence. Biofeedback is also used to improve performance under physiologically arousing conditions, e.g. for training pilots (Cowings et al., 2001).

From the Yerkes-Dodson law, it follows that it would be beneficial to monitor and control arousal to facilitate or enhance task performance. Multiple variables indicative of arousal are known in the art (e.g. EEG, heart rate, skin conductance, ... ). These indices of arousal however are not only influenced by arousal. Total heart rate for instance is composed of heart rate required for basal metabolism, for mechanical activity, for heat balance, as well as for arousal. In practice, arousal will be measured in two conditions: in (resting) subjects as such, and in (resting) subjects subjected to conditions increasing arousal. The differences between the two settings are then attributed to (physiological) arousal, the other components attributing to the index of arousal (such as mechanical activity, basal metabolism and heat balance) are considered invariable between the settings. However, this precludes the possibility of accurately measuring arousal in settings where changes in mechanical activity (or basal metabolism, or heat balance) will certainly have an impact on the index of arousal variable (e.g. in sports or other physical activities). Also, such studies are often based on off-line measurements (i.e. before and after induction of arousal). Moreover, there are pitfalls in relying on any single measure of arousal. For example, alerting caused by fear-evoking stimuli causes an increase in heart rate and other autonomic indices. In contrast, phasic alerting caused by orienting toward a non-threatening stimulus causes a slowing of the heart and other internal organs. Thus there is a need for methods that can specifically monitor the component of the index of arousal that is indicative of actual arousal, independent of physical activity. More particularly, such methods should take into account the complex, individual, time-varying and dynamic character of the individual organism monitored and be suitable for monitoring physical activity related variables and environmental variables as well.

SUMMARY OF THE INVENTION

There is a need to be able to isolate a factor (e.g. an arousal factor) related to a state of a human of animal such as a mental state, e.g. excitement, nervousness, anxiety, drowsyness, that are difficult to measure directly and to be able to control activity of the human or animal based upon such a factor. The present invention is based on the surprising fact that analysis of measured values relating to metabolic rate, physical effort such as mechanical effort or heat production using a model can obtain a control variable that relates to a state such as the mental state of the human of animal. The present invention starts from the premise that it is difficult to measure directly some states such as a mental state of a human of animal—such a state can however be obtained by comparing measured metabolic factors and/or variables relating to arousal and outputs of the model. One aim is to provide methods and systems for obtaining an index of arousal, whereby arousal can be "positive" such as excitement or "negative" such as drowsiness. Thus the present invention is based on the concept of obtaining a difficult to measure control variable from measurable values and a model.

According to a first embodiment, methods of monitoring and controlling the status of an individual human or animal are provided. These methods are based on a model capable of integrating measured, real-time information on one or more bioprocess inputs and one or more bioprocess outputs and linking this to the status of the individual human or animal. The methods comprise the steps of generating the model on-line, inputting the real-time information on bioprocesses of the human or animal, generating model outputs using a dynamic and adaptive on-line modelling technique, wherein at least one of the bioprocess inputs or outputs used as model input is a metabolism related variable of the human or animal and at least one of the bioprocess model outputs is an estimation of a component of an arousal variable (e.g. an arousal variable related to an index of arousal of the human or animal) based on the at least one metabolism related variable.

According to a particular embodiment, the mentioned variable that relates to an index of arousal of the individual human or animal is also measured as a bioprocess input or output.

According to a particular embodiment, the component of an arousal variable relating to an index of arousal of the human or animal (a model output) is based on the at least one metabolism related variable in that it is related to the variation of the at least one metabolism related variable used as a process input.

According to another particular embodiment, the estimated component of the arousal variable is an estimated physical component of the arousal variable, typically (but not necessarily) the mechanical component.

According to one embodiment, the model used is a so called black box model. According to another embodiment, the model used is a data-based model. According to another embodiment, the model used is a data-based mechanistic model (meaning that the parameters in the model have got physical or biological meaning).

According to a particular embodiment of the invention, the metabolism related variable is a performance related variable. According to yet a further particular embodiment, the metabolism related variable is a physical performance related variable.

According to one aspect of the invention, the estimated component of the arousal variable of the individual human or animal is linked to the status of the human or animal. For instance, the estimated heart rate component can be linked to health status or physical condition. According to a further specific embodiment, the measured metabolism related variable is also taken into account when linking the bioprocess inputs and outputs to the status of the individual.

According to another aspect, both the measured variable relating to an index of arousal and the estimated component of the arousal variable (which estimation is based on the at least one metabolism related variable used as model input) are used to link to the status of the individual. In one embodiment according to this aspect, the method comprises the step of determining a value for an unknown, e.g. a control variable from calculations involving a set of equations wherein at least the measured variable relating to an index of arousal and the estimated component of the arousal variable are known variables for the set of equations. A set of equations as used here means at least one equation with at least one unknown variable. This unknown variable can be attributed to the arousal of the individual if the estimated component of the arousal variable takes into account the physical related variables of the individual, which is normally the case when using metabolism related variables. The unknown variable can be used for control.

According to a particular embodiment, however, a component of the arousal variable relating to basal metabolism and a component of the arousal variable relating to heat balance are additional known variables in the set of equations. These three components (i.e. the component estimated on the basis of the metabolism related variable (which is a physical component often reflective of the mechanical component), the basal metabolism component, and the heat balance component) together form at least a good approximation to the total physical component of the arousal variable.

According to a specific embodiment, the value of the unknown, e.g. control variable can be used to monitor the arousal component of the variable relating to an index of arousal. This information is directly indicative of the status of the individual human or animal (e.g. the arousal status) and can thus be linked to the status of the individual. Methods according to yet a further embodiment use the value of the unknown variable to control the arousal component (i.e. the index of arousal) of the arousal variable.

A specific embodiment envisages that the determining of the value of the unknown, e.g. control variable is done by subtracting the estimated component of the arousal variable based on the at least one metabolism related variable, the component of the arousal variable relating to basal metabolism and the component of the arousal variable relating to heat balance from the measured variable relating to an index of arousal. In this embodiment, the resulting difference is the value of the unknown, e.g. unknown or control variable. This thus corresponds to the index of arousal.

According to a further aspect of particular embodiments, the value of the unknown, e.g. control variable can be used as a model input in an additional model or algorithm. This additional model or algorithm is then used for monitoring or controlling purposes.

According to another aspect, two models according to the aspect where an unknown, e.g. control variable is determined can simultaneously be used to monitor bioprocesses with different dynamic time windows (i.e. the model parameters and or the bioprocess variables do not change on a similar time scale). According to a further particular embodiment, at least one of the two models is a black box model. According to another particular embodiment, at least on of the two models is a data-based model. According to another particular embodiment at least one of the two models is a data-based mechanistic model. According to one specific embodiment, both dynamic, adaptive and on-line models use the same modelling technique.

According to a further particular aspect, the output of both models (e.g. the value of the unknown, e.g. control variable) is used as a model input in a further model or algorithm. Thus, these methods not only comprise the step of using the value of the unknown e.g. control variable as a model input in an additional model or algorithm for monitoring or controlling purposes, but further also generate a second unknown, e.g. second control variable and use this second unknown, e.g. control variable as additional model input in the additional model or algorithm for monitoring or controlling purposes. In a particular embodiment according to this aspect, the model output of this additional model or algorithm is used for the detection of Normal to Excessive Sleepiness in an Active Subject (NESAS). This means that the subject, for example, is doing an activity and fighting against sleep which is a different process from trying to go to sleep intentionally, e.g. when going to bed. According to a further particular embodiment, the additional model or algorithm is a black box model. According to another particular embodiment, the additional model or algorithm is a data-based model. According to another particular embodiment the additional model is a data-based mechanistic model. According to one specific embodiment, the additional model or algorithm uses the same modelling technique as at least one of the dynamic, adaptive and on-line models used for the generation of the additional model or algorithm input. According to another specific embodiment, the additional model or algorithm uses a different modelling technique than the two dynamic, adaptive and on-line models used for the generation of the additional model input.

Methods according to the particular aspect of the invention where an unknown, e.g. control variable is determined based on the difference between the measured variable containing an index of arousal and the total physical part of this variable (i.e. the estimated part of this variable related to the metabolic heat production or physical performance added with the parts related to basal metabolism and heat balance), offer a whole new perspective by allowing the on-line determination of an index of arousal, as well as the determination of the physical component of an arousal variable. Indeed, there is a need in the art for methods (techniques, protocols) to reliable quantify the physical status and/or arousal of an individual human or animal in real-time, especially during activity, without disturbing the normal activity of the subject.

It is known that the total performance of a person or animal depends on the physical status and the mental status/arousal as well (see FIG. 3A). When measuring a variable like heart rate it is impossible to measure this variable without the possible influence of arousal. For example excitement (an arousal) can increase heart rate as well as physical exertion. Hence mental processes may be a component of the level of heart rate. Consequently a same physical training will not generate a unique heart rate in a same person since the heart rate is influenced by the arousal. This means that today's practice to use the measured total heart rate as a measure for physical condition is not an accurate measurement since the influence of arousal is not considered. Heart rate monitors used to train physical heart rate actually measure total heart rate and cannot distinguish between heart rate due to arousal (e.g. involving mental such as emotional components) and heart rate related to physical activity (or in particular mechanical activity). So this way of working is not the most efficient training of physical condition. For instance, a formula 1 pilot who does not perform physical activity while visualising himself driving a round on a track can still achieve a very high heart rate. This is due to arousal and not due to physical activity. Thus, the arousal component of heart rate cannot be neglected, and it is an objective of specific embodiments to be able to monitor both physical and arousal components of a variable relating to containing an index of arousal.

The same applies for other variables, the present invention is not limited to heart rate. For example, when an individual blushes (e.g. due to shyness or embarrassment), he or she will not perform physical activity, yet the arousal status of the individual changes: there is vasodilatation and increased blood flow through the cheeks which also results in temperature differences that can be measured, as well as other physical effects such as sweating will increase, etc. These changes, e.g. blushing, can also occur when performing physical activity (e.g. running), again stressing that physical and arousal components influence bioprocesses and that both need to be first known and then secondly taken into account separately to allow efficient monitoring. Note that the dynamics of the arousal component often are much faster: One can start blushing immediately after a remark, while blushing related to physical activity usually takes longer to develop.

In accordance with embodiments of the present invention it is possible to decompose the total variable containing an index of arousal (e.g. heart rate) into a physical and an arousal component and to measure this in real time during an activity, so that the physical training of the individual also becomes more efficient since now there is a good measure for physical performance and there is more accurate feedback about the physical condition (See FIG. 3B the General scheme of physical and arousal HR component). In this case, training can be achieved using the component of heart rate effectively related to physical activity, instead of total heart rate.

According to a specific embodiment, this is achieved through 1) on-line and continuous measurement of both individual activity/performance or metabolic heat production related variable (input) and responding effect on a total variable relating to an index of arousal (output) and 2) decomposition of the total variable relating to an index of arousal into 'physical' and 'arousal' components of the variable relating to an index of arousal. Under these conditions, the physical status and/or arousal of any individual can be quantified, even during an activity under different changing environmental conditions and by use of relatively simple technology, e.g. a heart rate measurement device and a device for measuring activity.

The first condition implies that, in order to quantify, for instance, a training session of a sports athlete, the (mathematical) relation between performed training activity and the response of the athlete's body to this activity contains valuable information. The second condition stipulates that, in order to quantify physical status and/or arousal characteristics from the variable relating to an index of arousal, one has to separate arousal and physical aspects since otherwise it is not known how much they influence each other and disturb the calculated features. The physical component of the variable relating to an index of arousal can be estimated by using one or more physical performance related or metabolic heat production related variables as bioprocess inputs and using the model to calculate the part of the variable relating to an index of arousal that is related to this (these) metabolic heat production related or physical performance related variable(s). Based on these one or more inputs, the arousal component can be estimated e.g. by subtracting the sum of the estimated physical/metabolic related component and the basal metabolic and the heat balance related component, from the total, measured variable relating to an index of arousal.

When the two conditions mentioned above are fulfilled, existing techniques for process monitoring and control can be applied to both components of an individual's performance, in order to monitor and/or control both arousal and physical components of the index of arousal, particularly during activity of an individual. In particular, data based on-line modelling techniques are envisaged to be implemented in the methods according to specific embodiments.

The use of a data based on-line modelling technique, based on real-time information, measured dynamically on inputs and outputs of the bioprocess offers the advantage that such models can have a simple structure with a low number of parameters that can be updated in real time, yet surprisingly enable accurate prediction of the dynamic CITD behaviour of complex bioprocesses. Thanks to their simple structure and low number of parameters, said models can be readily implemented in (real-time) process control means, at commercially acceptable costs.

In accordance with the present invention, on-line modelling at least refers to techniques where a model of the process is identified as the output or input-output data of the process become available. Synonyms are real-time identification and recursive identification (Ljung, 1987. System Identification: theory for the user, p. 303-304, New Jersey: Prentice Hall). With these modelling techniques the model parameters of a mathematical model structure are estimated, based on on-line measurements of the process inputs and outputs. This parameter estimation can be performed recursively during the process resulting in a dynamic model with time-variant model parameters that can cope with the dynamic behaviour of most bioprocesses (Ljung, 1987; Goodwin and Sin, 1984) or behaviour of individual living organisms.

By applying the methods according to the present invention there is at every moment a dynamic model available of the physical and arousal status of an individual. This dynamic model can subsequently be used in real time to estimate and predict the process output several time steps ahead. These predictions can be compared to actual measured output values to decide whether the model needs updating. When the model is correct and updated then the predictions can be compared to actual measured output values and a predefined, reference output, based on which comparison a suitable monitoring and/or control strategy can be determined, to control the input of the process such as to achieve the predefined output trajectory, preferably with a minimum of input effort.

One way to on-line model the dynamic responses of an individual or a bioprocess with time-variant characteristics according to one embodiment is by applying in real time recursive linear regression. Such approach offers the advantage that, although it is based on a simple model structure, it can cope with non-linear characteristics of processes by estimating the model parameters each time new information is measured on the process. Furthermore the model structure and number of parameters can cope with multiple process inputs and/or multiple process outputs.

The recursive modelling technique according to such embodiments requires on-line measured input-output information of the process. From practice, systems are known which can measure the required information automatically. However, it is also known that such automatic measurement systems may sometimes yield incorrect measurement values. In order to prevent such incorrect measurements from affecting the model accuracy, a method according a specific embodiment may be provided with features to evaluate incoming measurements and reject or adapt said measurements in the event inconsistencies are detected. For the evaluation of the measured output data, effective use can be made of the model. For instance, the predicted average output of said model can be used to evaluate the validity of measured output values.

According to a particular embodiment of methods according to the aspect wherein the value of the unknown, e.g. control variable is determined, the value of the unknown, e.g. control variable is determined over time, resulting in knowledge of the dynamics of the unknown, e.g. control variable. According to a further embodiment, the value of the unknown, e.g. control variable is then classified as containing arousal events or not, depending on the dynamics of the unknown, e.g. control variable (which corresponds to the arousal component of the index of arousal). In an alternative embodiment, the value of the unknown, e.g. control variable can be classified as containing arousal events or not, depending on the dynamics of the (total) index of arousal.

According to yet a further particular embodiment, the arousal events are not only classified as containing arousal events or not, but further classified as contributing to positive, neutral or negative arousal. As with the first classification, the classification depends on the dynamics of the unknown, e.g. control variable (i.e. the arousal component of the index of arousal), or, alternatively, on the dynamics of the (total) index of arousal.

Of course, the division of the index of arousal into a physical and arousal component also allows monitoring and controlling the physical component of the index of arousal instead of only the arousal component. According to a particular embodiment, the methods further comprise the step of using the estimated component of the arousal variable based on the at least one metabolism related variable to monitor and/or control the physical component of the arousal variable. According to a further particular embodiment, in addition to the estimated component of the arousal variable based on the at least one metabolism related variable, a component of the arousal variable relating to basal metabolism and a component of the arousal variable relating to heat balance are taken into account to monitor and/or control the physical component of the arousal variable.

This information is directly indicative of the status of the individual human or animal (e.g. the physical status) and can thus be linked to the status of the individual.

According to a particular embodiment of methods to decompose the physical status and the arousal the dynamics of the model parameters modelling the physical status of the individual will be different from the dynamics of the model parameters modelling the arousal component of the individual. The physical response of the body to a physical performance of metabolic production needs more time to change in time than the arousal component that can change rapidly. This difference in time to develop can be used in accordance with embodiments of the present invention to decompose more accurately the physical component from the arousal component by dynamics analysis. For example, according to a particular embodiment, the dynamics of the model parameters modelling the physical status of the individual can be used to detect whether the individual has taken or been administered medication, stimulants or some form of drugs or doping. Indeed, if the timescale for updating the model parameters modelling the physical status of the individual becomes significantly smaller, this is indicative of an unnatural change in the body of the individual, as the body normally only gradually adapts itself to new circumstances (hence the slower timescale of change for physical relative to arousal model parameters). Such a sudden change of how the body reacts can however be achieved using performance-enhancing drugs or doping. Thus, according to a particular embodiment, the dynamics of the model parameters modelling the physical status of the individual are used to detect whether the individual has taken or been administered doping.

According to another particular embodiment of methods to decompose the physical status and the arousal component in the variable containing an index of arousal, the data where the dynamics of this measured variable occurs without a corresponding variation in the measured physical/metabolic related variable shows that in such case the variable containing an index of arousal is composed of mainly arousal without a physical related component. This is for instance the case for the training of a Formula 1 pilot visualising himself driving around a track without actually performing physical activity. Thus, according to a specific embodiment, the physical and arousal component of the variable relating to an index of arousal can be monitored, even though one of the components does not change over time, or when its value is zero. Even when the value is zero, the component (whether it is a physical or arousal component) is deemed to be present.

According to a specific embodiment, the variable relating to an index of arousal is heart rate.

According to a further specific embodiment, the estimated index of arousal (i.e. the estimated heart rate) is based on at least the estimated heart rate required for mechanical activity. According to a further embodiment, the estimated heart rate is based on at least the estimated heart rate required for mechanical activity and at least one variable selected from the heart rate required for basal metabolism and the heart rate required for maintaining heat balance.

According to yet a further specific embodiment, the estimated heart rate is based on the estimated heart rate required for basal metabolism, the estimated heart rate required for mechanical activity and the estimated heart rate required for heat balance.

According to another specific embodiment, the variable relating to an index of arousal is muscle activity, body movement or body motion. The variable, e.g. muscle activity, body movement or body motion can be monitored by any suitable technique. According to yet another specific embodiment, muscle activity, body movement or body motion is monitored by using image analysis or image processing. For instance, video images can be used to record movement, as well as e.g. (facial) expression. The process of obtaining movement information from images can be automated. So too can the process of obtaining specific movement information (e.g. facial expression information) from total movement information.

According to another specific embodiment, the variable relating to an index of arousal is the sound produced by the living organism. According to yet another specific embodiment, sound produced by an organism is monitored fully automatically by using real time sound analysis. For instance, sound production can be used to record sound related to physical performance such as body movement, body motion or displacement.

According to a particular embodiment, the variable relating to an index of arousal is heart rate, EEG, sound production, image information or muscle activity.

It is envisaged that the methods of the invention can be practised on all animals. According to a particular aspect, the methods of the invention are used to monitor and/or control vertebrate animals. According to a further aspect, the methods are put into practice to monitor and/or control fish. According to another aspect, the methods are put into practice to monitor and/or control mammalian or avian species. According to yet a further particular aspect, the methods are used to monitor and/or control the status of an individual chicken, e.g. a laying hen. According to yet a further particular aspect, the methods are used to monitor and/or control the status of an individual horse. According to yet a further particular aspect, the methods are used to monitor and/or control the status of an individual cow. According to another particular aspect, the methods are used to monitor and/or control an individual human.

The metabolism related variable used as model input can be selected from a wide variety of variables. According to a specific embodiment, the metabolism related variable is selected from training activity, body movement, body part movement (e.g. head movement), power production, motion, speed, speed as a vector, acceleration, acceleration as a 3D vector, cadence of a cyclist, and any other form of behaviour. According to another specific embodiment, the metabolism related variable is selected from training activity, body movement or body part movement, and power production.

It is particularly envisaged that the models can take into account the changing relationship between bioprocess inputs and outputs. The relationship between bioprocess inputs and outputs typically will change under the influence of environmental variables or disturbing variables or due to the time varying character of the individual living organism. Methods according to a specific embodiment make use of a model that takes into account effects of external disturbances of a time varying character to redefine the relation between bioprocess inputs and bioprocess outputs. According to another particular embodiment, the method uses a model that takes into account effects of external disturbances or variables considered as external disturbances to redefine the relation between bioprocess inputs and bioprocess outputs. According to yet another particular embodiment, the method uses a model that takes into account effects of external disturbances to redefine the relation between bioprocess inputs and bioprocess outputs.

The methods currently provided are very well suited to monitor bioprocesses in an individual human or animal, and by monitoring these bioprocesses, they provide information on the physical status and/or arousal status of the human or animal. According to one aspect of the invention, these methods can be used to control a bioprocess in the human or animal. As a result, the status of the individual animal can be changed. Controlling of a bioprocess is typically achieved by changing the bioprocess input, as thereby the bioprocess output will be changed. As the model used in the methods models the bioprocess by describing the relation between bioprocess input and bioprocess output, predictions can be made of the change in value of the bioprocess output when a bioprocess input is changed. This way, the bioprocess output can be 'guided' to a desired value, or a desired trajectory (i.e. more than one desired value over a time range) by appropriately changing or adjusting the bioprocess input. According to this specific embodiment, the use of a method to direct a bioprocess output towards a desired output value or trajectory is envisaged. If, according to a particular aspect, the bioprocess output is split up into different components, the different components can be directed separately towards a desired output value or trajectory. For instance, the arousal component of a variable relating to an index of arousal can be controlled in this manner. Similarly, the physical component of the variable relating to an index of arousal can be controlled. Both components can be monitored and/or controlled at the same time, during a normal period to train athletes for example. Alternatively, only one of the components is monitored and/or controlled.

According to another aspect, systems are provided that can be used to practice the methods described herein. According to a first embodiment, a system is provided for monitoring the status of an individual human or animal, comprising

- (a) means for collecting and storing real-time information on bioprocess inputs and outputs, wherein at least one of the bioprocess inputs or outputs is a metabolism related variable of the human or animal, and wherein a measured variable relating to an index of arousal of the individual human or animal is another bioprocess input or output;
- (b) means for on-line modelling and generating an estimation of a component of the same variable relating to an index of arousal of the human or animal mentioned in (a), based on the at least one metabolism related variable.

According to a further embodiment, the system provided can also be used to control the status of the individual human or animal.

According to a further embodiment, a system is provided that further comprises

- (c) means for on-line modelling and generating the value of an unknown, e.g. a control variable from calculations using a set of equations wherein the measured variable containing an index of arousal and the estimated component of the arousal variable are known variables for the set of equations.

According to yet a further embodiment, systems for controlling the index of arousal are provided that further comprise:

- (d) means for comparing and determining the variance between the estimated component of the arousal variable and a preset reference physical component of the arousal variable;
- (e) means for comparing and determining the variance between the generated value of the unknown, e.g. control variable and a preset reference index of arousal (i.e. arousal component of the arousal variable);
- (f) means for determining how one or more bioprocess inputs should be adjusted in relationship to the variance determined with (d) and/or (e).

Variance as used in these claims is also intended to include the term dynamic variation.

Any of the provided systems can be used to monitor and control the status of an individual human or animal. Depending on the bioprocess monitored, appropriate bioprocess inputs and outputs can be selected to measure with the means for collecting and storing real-time information on bioprocess inputs and outputs. According to one specific embodiment, a system is provided for monitoring and controlling the status of an individual human, wherein the metabolism related variable is selected from the group consisting of training activity, body movement or body part movement, and power production; and the index of arousal is heart rate or muscle activity.

According to another aspect of the invention, systems that have means for on-line modelling and generating the value of an unknown, e.g. control variable from a set of equations further comprise means for on-line modelling and predicting a bioresponse or bioprocess output based on the input of at least the value of the unknown, e.g. control variable. In practice, this means that the value of the unknown, e.g. control variable can be used as input in a second model or algorithm. This second model or algorithm typically will also describe a bioprocess, and the model output is a bioresponse. According to a further specific embodiment, the bioresponse that is predicted using such systems is Normal to Excessive Sleepiness in an Active Subject (NESAS).

Any one of the systems described in this application may further comprise means for outputting information on the bioprocess. According to a specific embodiment, the system further comprises means for outputting information on the bioprocess, wherein these outputting means are display means. The outputting means may be used to output any type of information obtained using the systems or methods of the invention. Thus, these means may output information obtained with any of means (a) to (f), with the means for on-line modelling and predicting a bioresponse based on the input of at least the value of the unknown variable, or information that is entered in the system via another way (e.g. a reference trajectory for a variable that is inputted by the user). The output may be displayed or outputted directly (e.g. the value of a variable) or indirectly (e.g. a text message with instructions of how a bioprocess input should be modulated).

According to another particular embodiment, the systems described in this application may further comprise alarm or signalling means. Typically, these alarm or signalling means will produce an alarm or signal when a monitored bioprocess input or output or a predicted model output exceeds a certain threshold. For instance, an alarm may be started when the measured value of the bioprocess output is significantly different from the estimated value of the bioprocess output (e.g. an index of arousal). Or a signal may be given to alter the training activity (as example of a bioprocess input) of an individual human or animal in order to follow a reference heart rate trajectory (as an example of a desired bioprocess output). Typically, the alarm or signalling means will make use of visual or sound signals, although other possibilities are also envisaged (e.g. radio waves). The systems may also comprise controlling means.

According to a particular embodiment, two or more means of the systems may be integrated. For instance, more than one of the modelling means may be integrated in one computational module. According to another embodiment, the alarm or signalling means of the system are integrated with the outputting means. According to one specific embodiment, the system is contained in one physical entity. According to another specific embodiment, the system is provided as at least two physical entities or devices, wherein at least one physical entity (or device) is fixed on or in the individual human or animal when in operation, and at least one other physical entity (or device) is in another location (i.e. not fixed on or in the human or animal).

The present invention also provides a computer program product, e.g. software code which when executed on a processing engine having a processor and memory provides any of the methods or systems of the present invention.

FIGURE LEGENDS

In the different Figures, the same reference signs refer to the same or analogous elements.

FIG. 1 depicts a general method of how processes can be controlled using feedback control, here exemplified for the process of driving a car. Control is achieved by using continuous feedback (1) from process outputs. Based on monitored process inputs and outputs, the model can make a prediction (2). Control based on the model output (3) can be achieved by adapting process inputs.

Figure 3A:
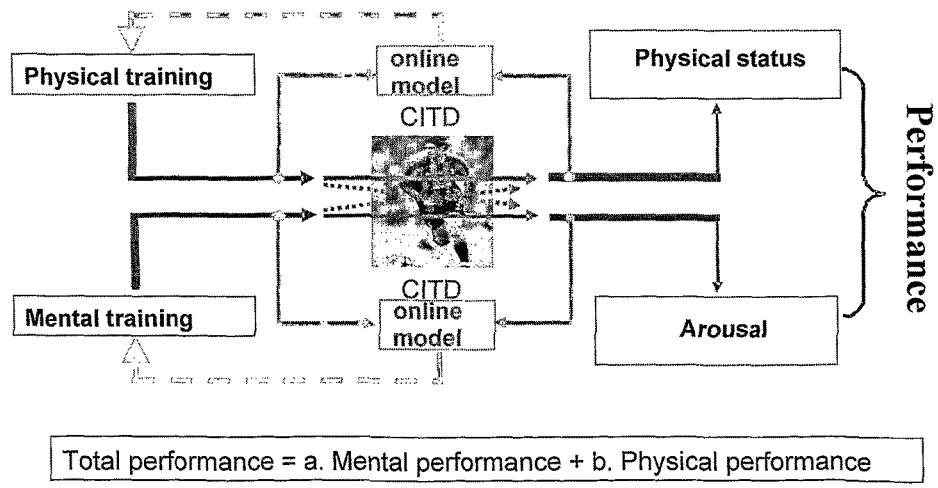
FIG. 3A is a general scheme of how physical and mental processes and performances influence each other: the total performance capacity of an athlete can be divided in a physical and mental (or arousal) component. The mental/arousal status of the individual will influence physical performance and vice versa.
Figure 3B:
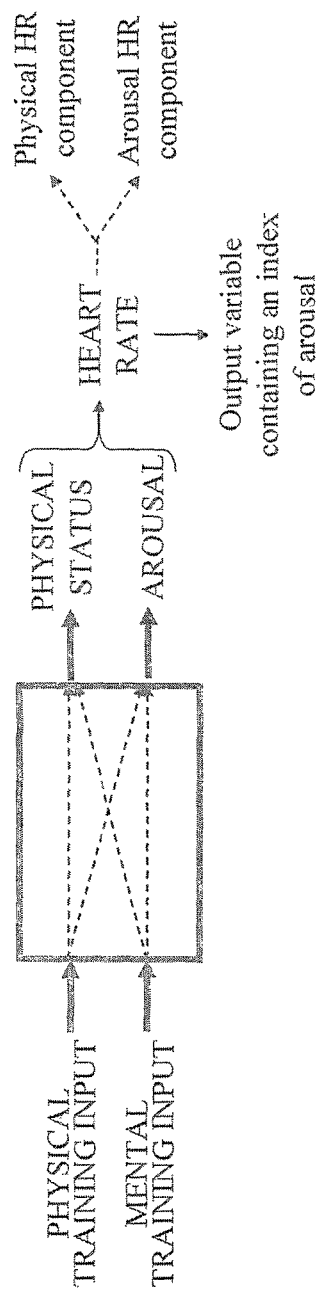

FIG. 3B. Upper plot: General scheme of how physical and mental processes and performance influence each other. The lower plot details how the physical processes can be influenced by a feedback of the arousal process.

Figure 4:
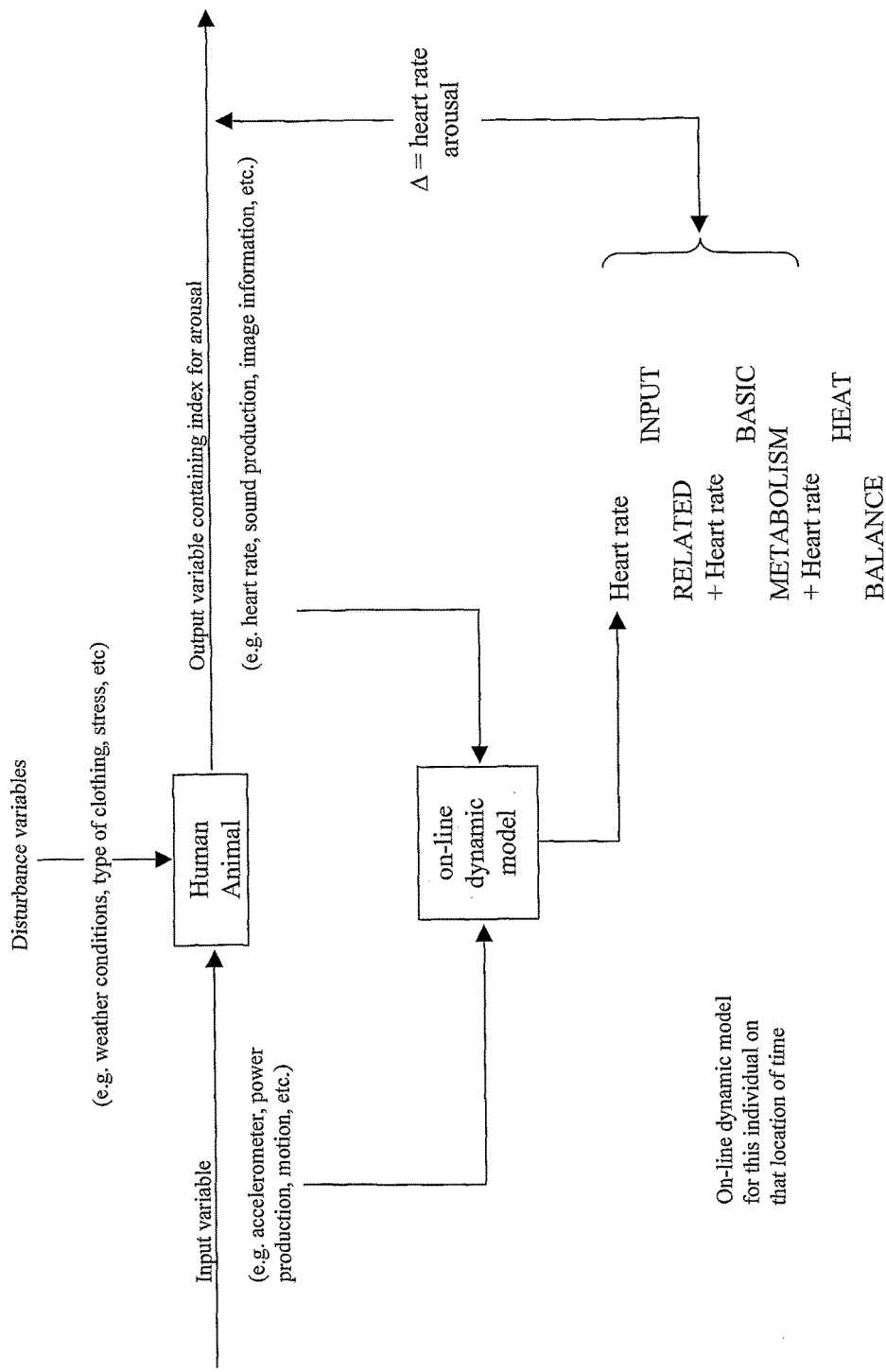

FIG. 4 shows a method according to one specific embodiment. Bioprocess input and output variables are continuously monitored. Based on the inputs, the on-line dynamic model can estimate a value for an index of arousal (output variable). The difference between the measured bioprocess output and the estimated value (taking into account components due to mechanical activity, basal metabolism and heat balance) is indicative of actual arousal (i.e. the arousal component of the index of arousal). This value can further be controlled (not shown in figure).

Figure 5:
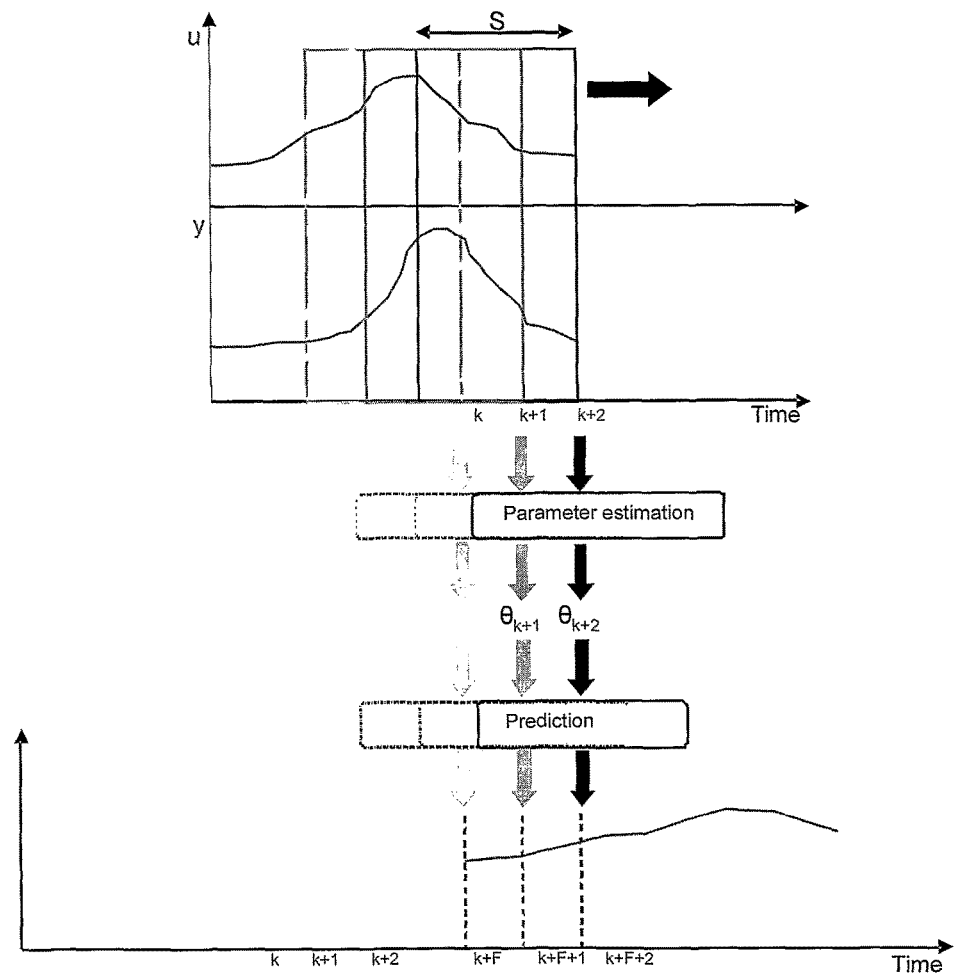

FIG. 5 represents a schematic visualization of adaptive on-line model predictions. At every moment k, the process input u and output y and the model parameters $\theta_k$ of a compact model are estimated based on a limited time-window of historical measurement data. Based on this model, the process output $\hat{y}$ can be predicted at every moment k for a future horizon k+F.

Figure 6A:
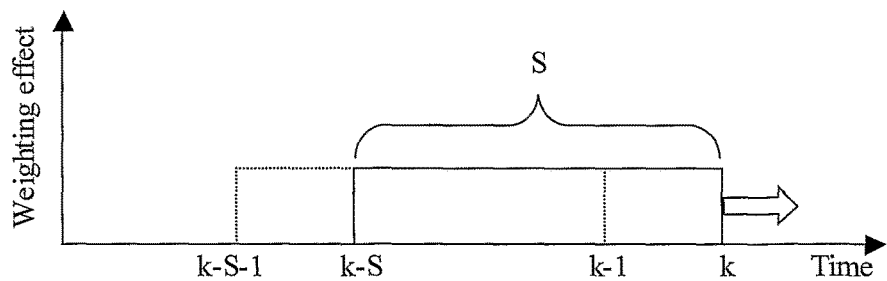

FIG. 6A: shows the principle of a moving rectangular window for estimation of time-variant model parameters. k is the discrete time instant; S is the size of the time window.

Figure 6B:
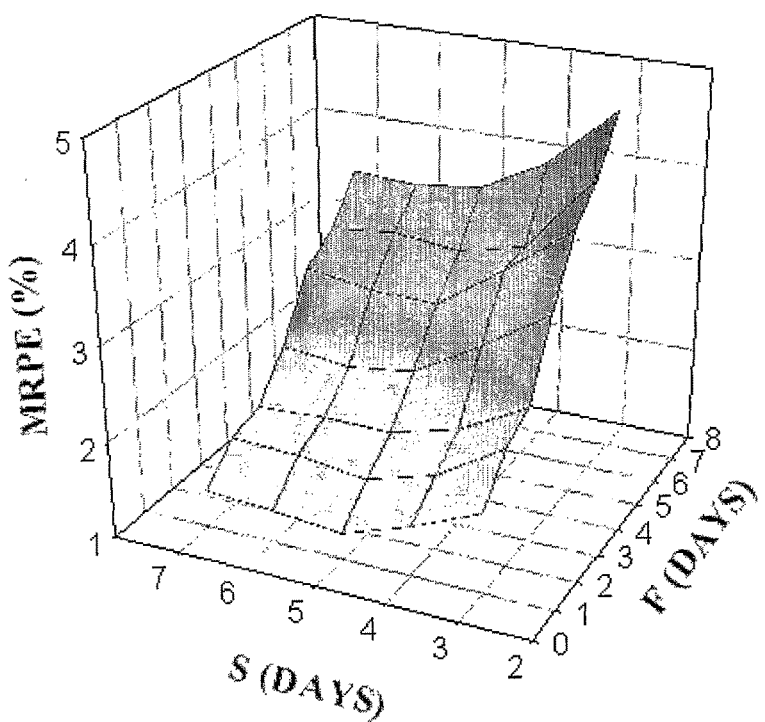

FIG. 6B. A typical example of the mean relative prediction error (MRPE) as a function of window size S and prediction horizon F.

Figure 7A:

FIG. 7A represents a block scheme with an input signal (training input) and output signal (heart rate response).

Figure 7B:
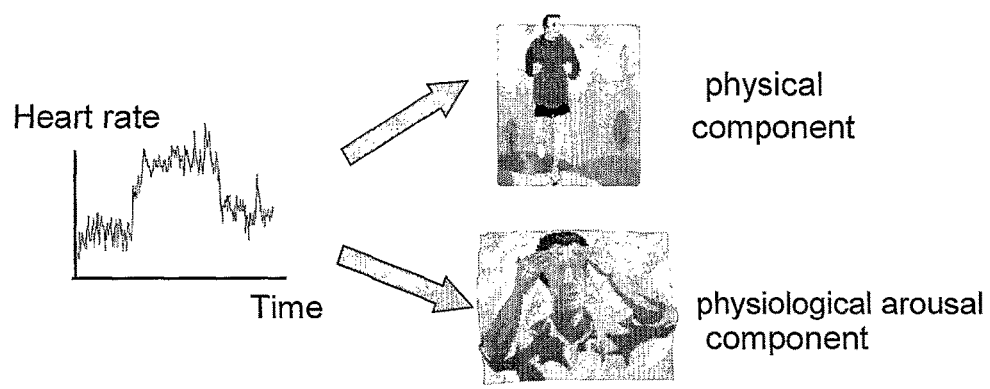

FIG. 7B shows how both the physical and arousal component of heart rate determine the individual and time-varying total heart rate response.

Figure 7C:
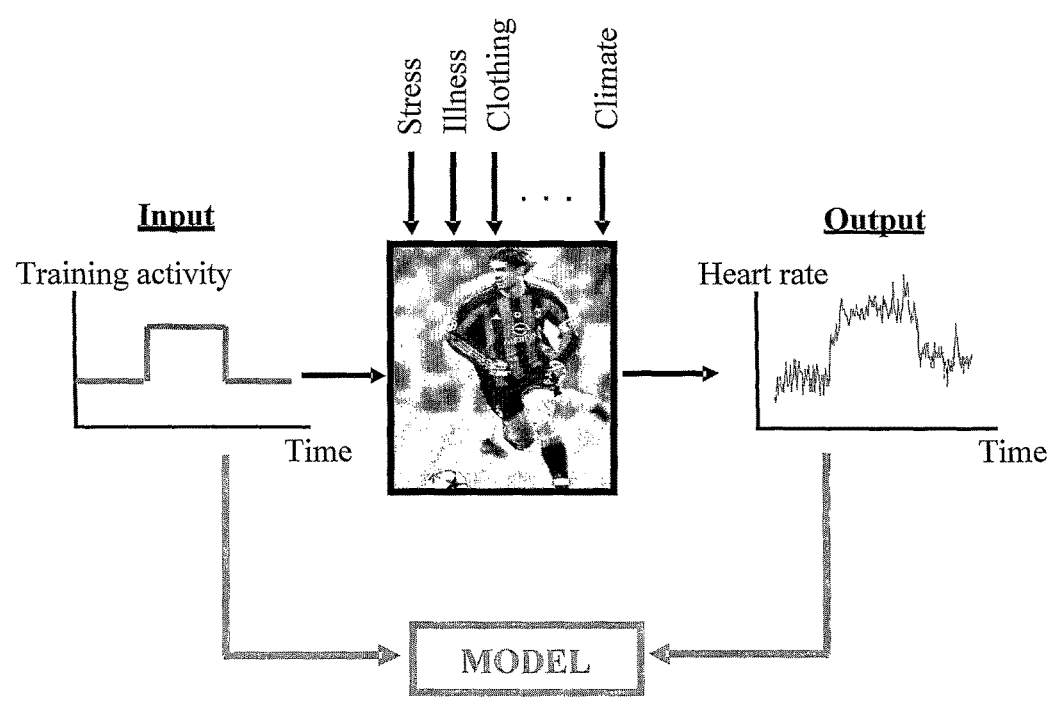

FIG. 7C is a schematic representation of the identification of a continuous and online model between input (here training activity) and output (here heart rate) for a sports athlete.

Figure 8A:
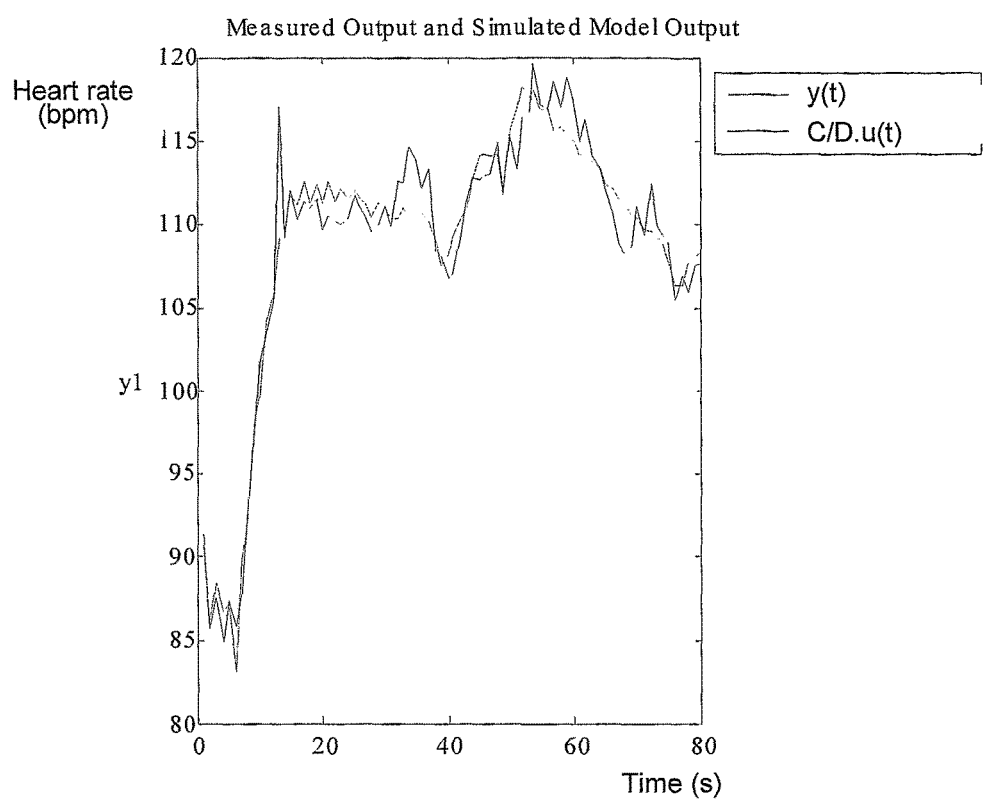

FIG. 8A shows the measured total heart rate y(t) and the physical component of heart rate calculated from the identified transfer function model for a training exercise of 80 seconds.

Figure 8B:
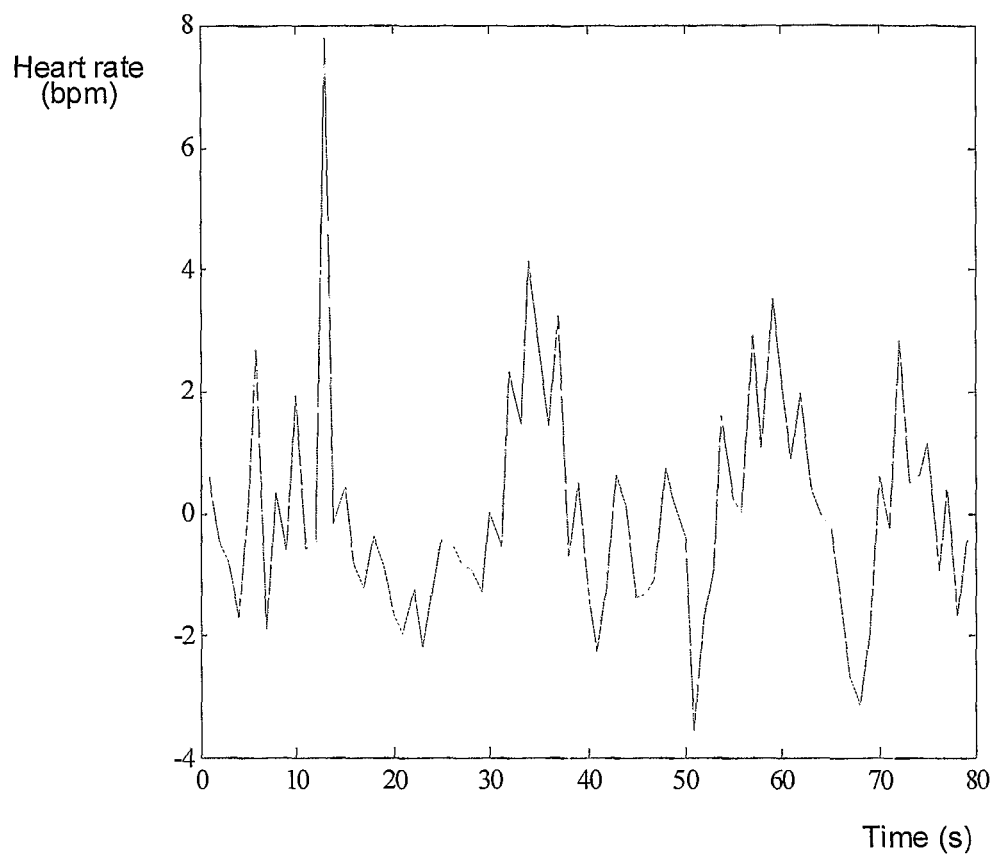

FIG. 8B shows the arousal component of heart rate calculated from the identified transfer function model for the same training exercise of 80 seconds, by subtracting the physical component of heart rate from the total heart rate.

Figure 8C:
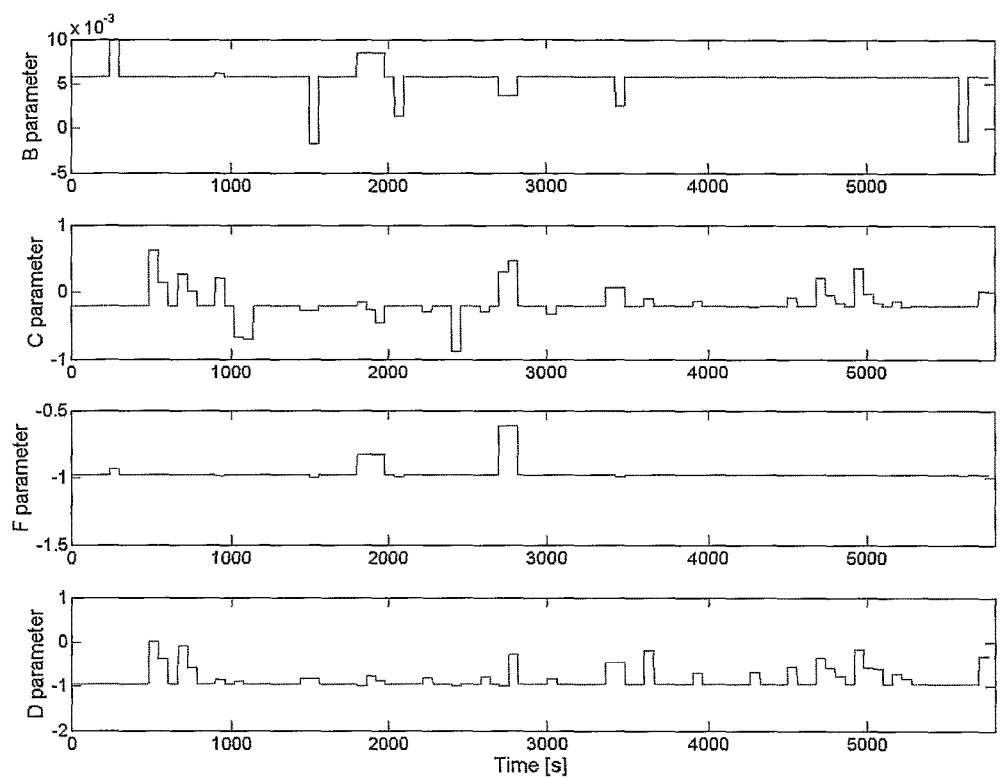

FIG. 8C: Variation of model parameters of the physical and arousal component of heart rate over time for a professional soccer training session.

Figure 8D:
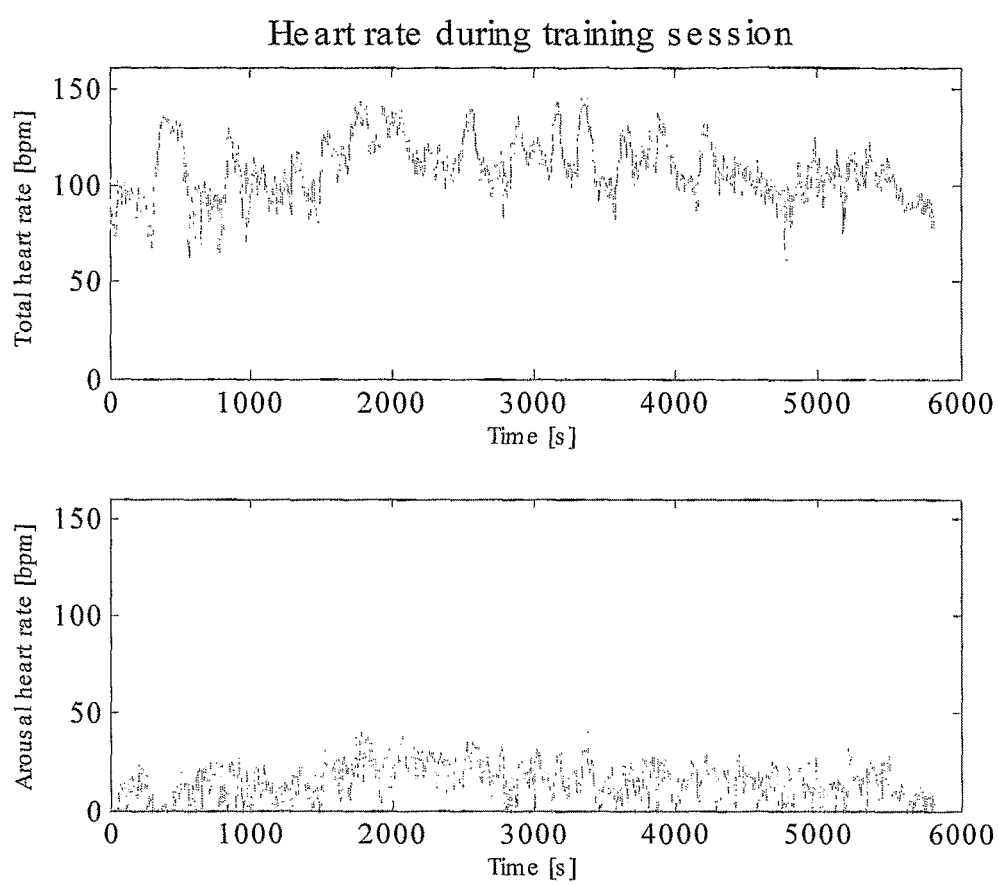

FIG. 8D: Total heart rate and on-line calculated arousal component of heart rate during a professional soccer training session.

Figure 9:
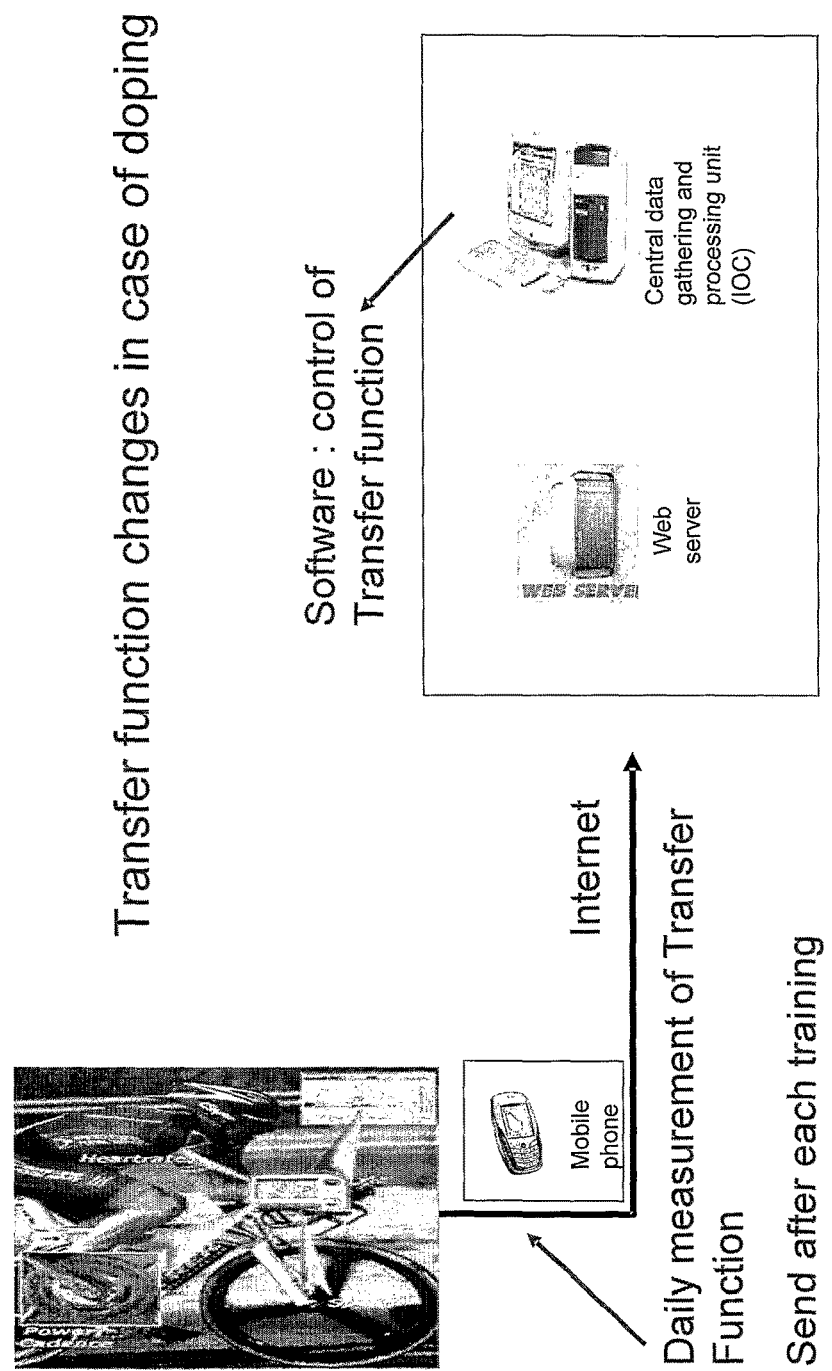

FIG. 9 shows the general concept of early warning doping detection. The metabolic input variable delivered effort and the output variable heart rate are continuously and on-line measured. The model characteristics are sent telemetrically (by e.g. wirelessly by a cell phone) to a central web server and data processing unit. The software on the data processing unit detects unrealistic changes over time in the model characteristics that might indicate unnatural performance (e.g. doping).

Figure 10:
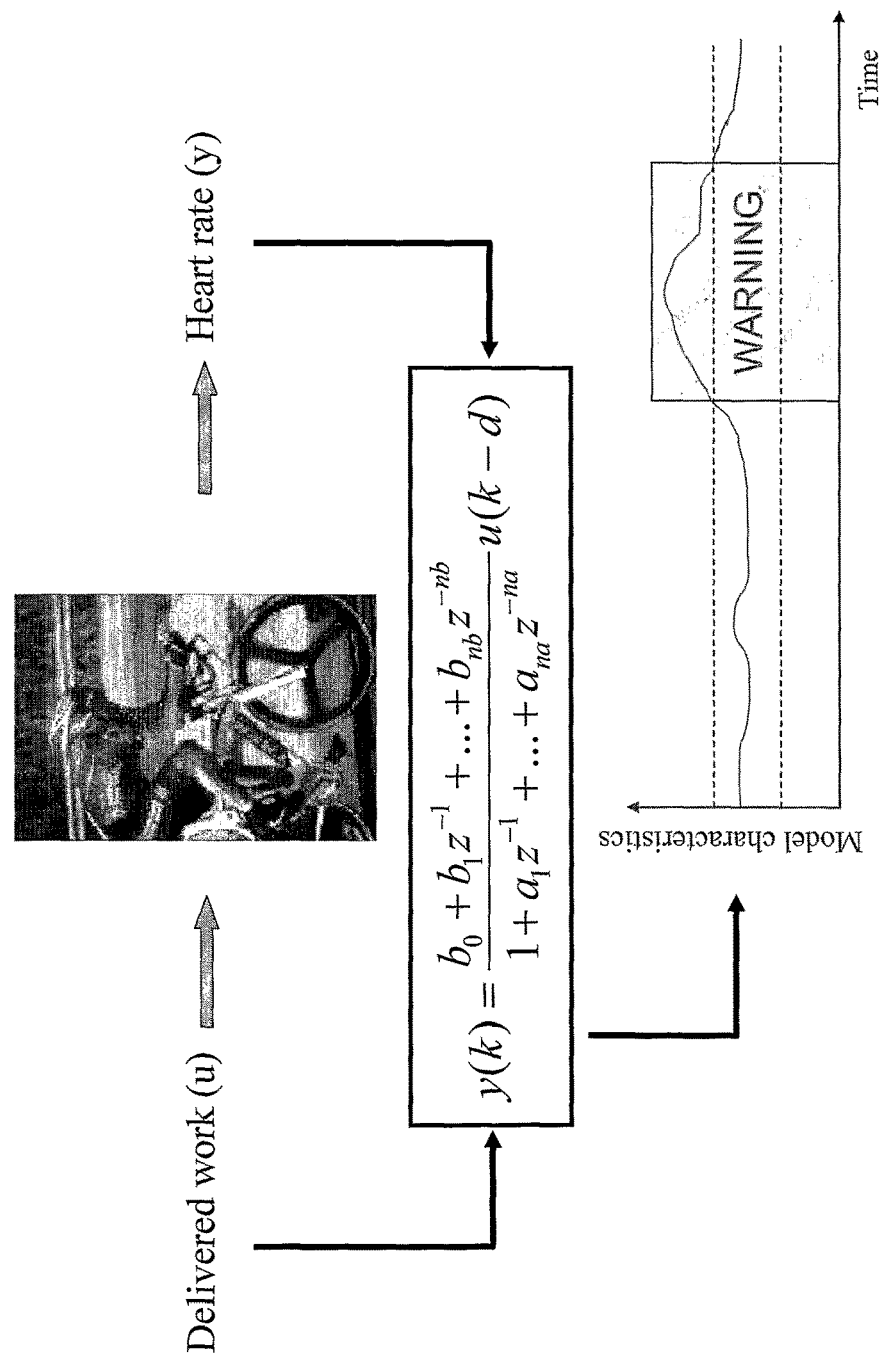

FIG. 10 shows a schematic overview of the model used for monitoring doping usage. A model is identified as the relation between the process input u (delivered work) and the process output y (heart rate). This model generates an output $\hat{y}$ which approximates the part of y directly related to the process input u. This corresponds to the physical component of delivered work, while the difference between the model output and the process output is representative of movement due to arousal. The physical component of delivered work as an output is modelled to input variable delivered work by a transfer function model. This transfer function model is than checked for unnatural changes in the model characteristics that can indicate doping use and set of a warning.

Figure 11:
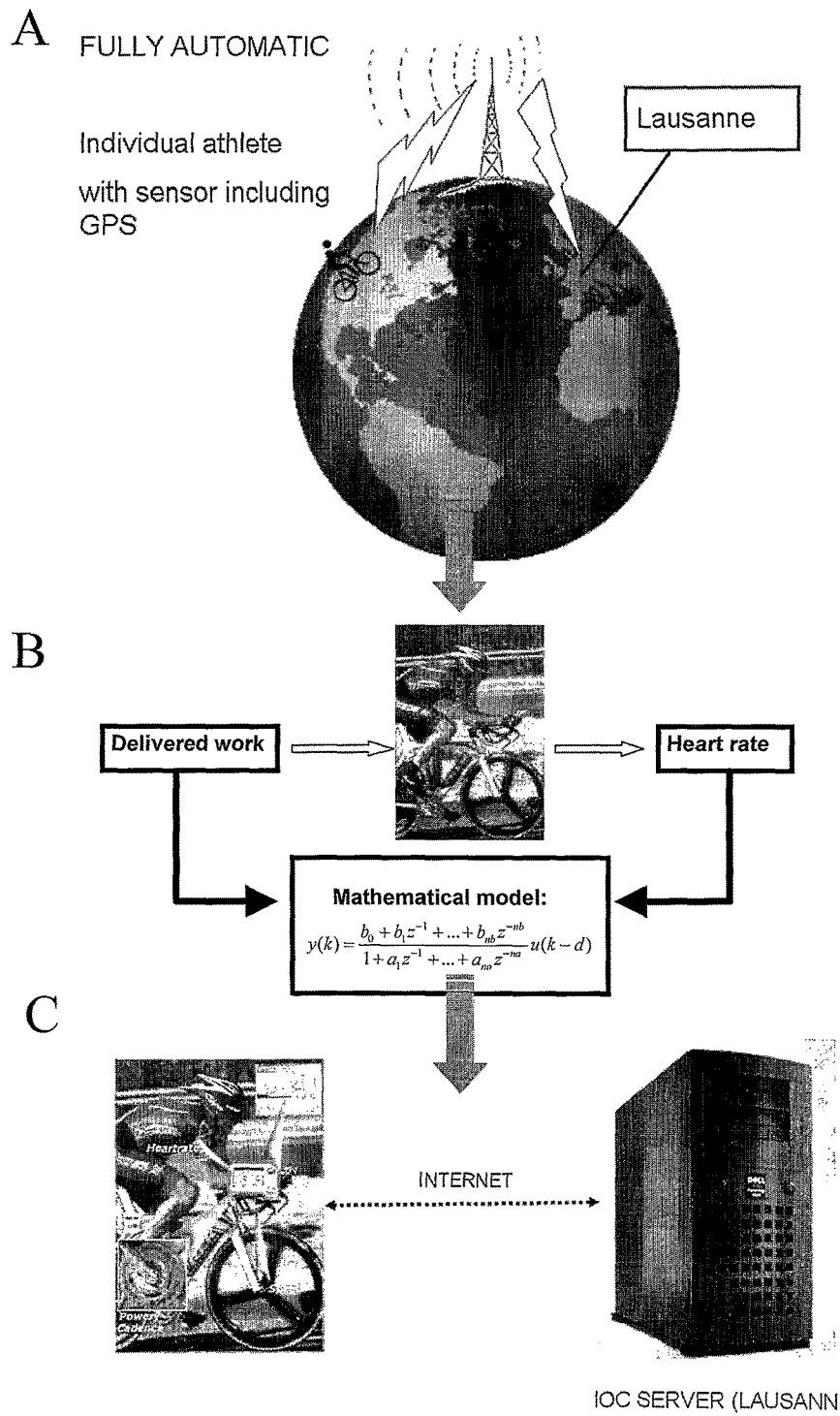

FIG. 11 shows the general concept of early warning doping detection. The individual athlete is monitored during training and his/her training data are send to a central web server and data processing unit (e.g. at a central sports organization). The software on the data processing unit detects unrealistic changes over time in the model characteristics that might indicate unnatural performance (doping).

Figure 12:
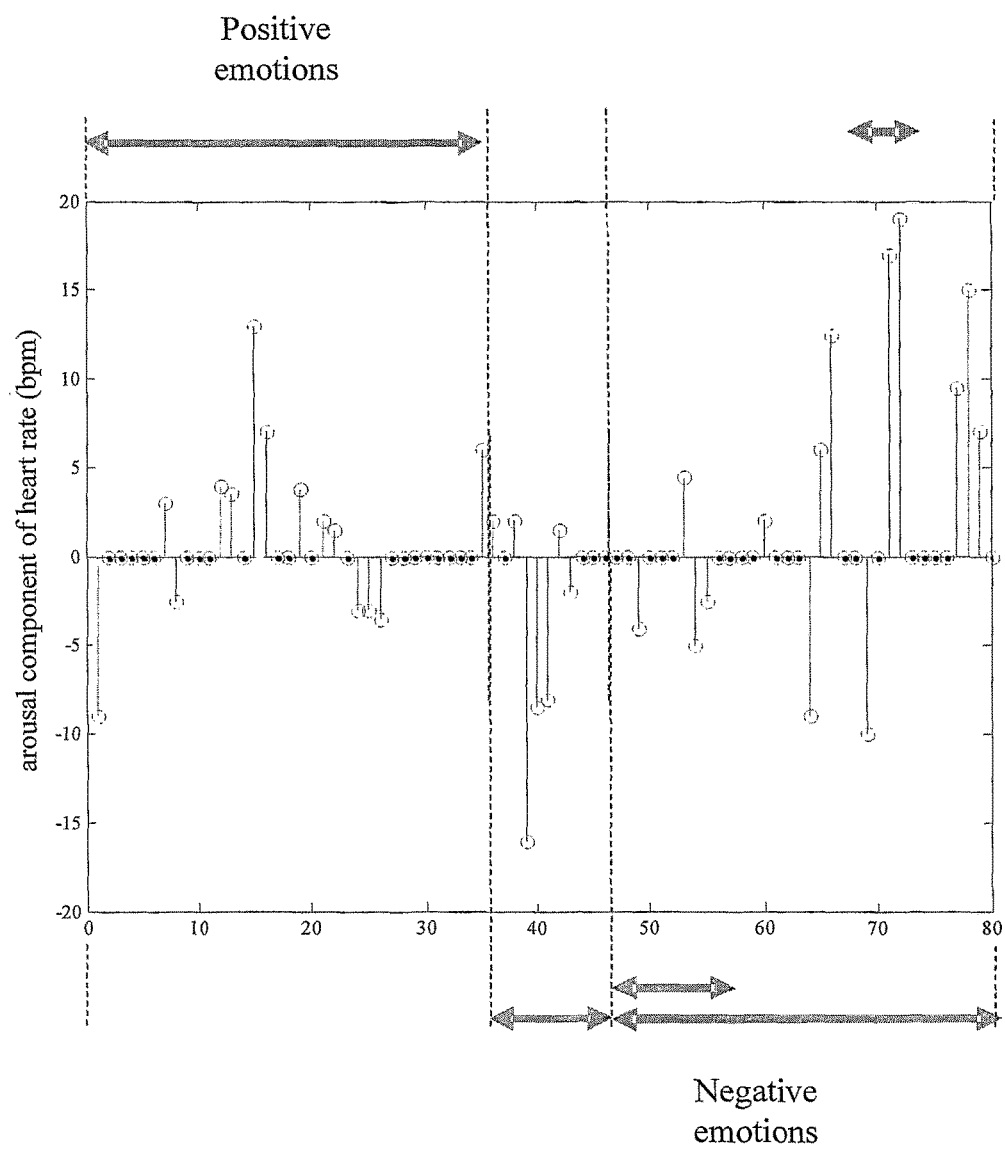

FIG. 12: Scoring of (physiological) arousal and linking to the quality of arousal during a soccer game. All actual values of heart rate (in beats per minute) shown are in reality positive values. However, to discriminate between arousal events classified as positive arousal events and those classified as negative arousal events, the negative arousal events are depicted as negative values. Thus, the stems with positive values represent a minute with mainly positive emotions, while a stem with negative values represents a minute with mainly negative emotions. The double arrows at the bottom (for negative emotion/arousal) and top (for positive emotion/arousal) of the figure show the reference scoring of the arousal for this game (i.e. using traditional techniques).

Figure 13A:
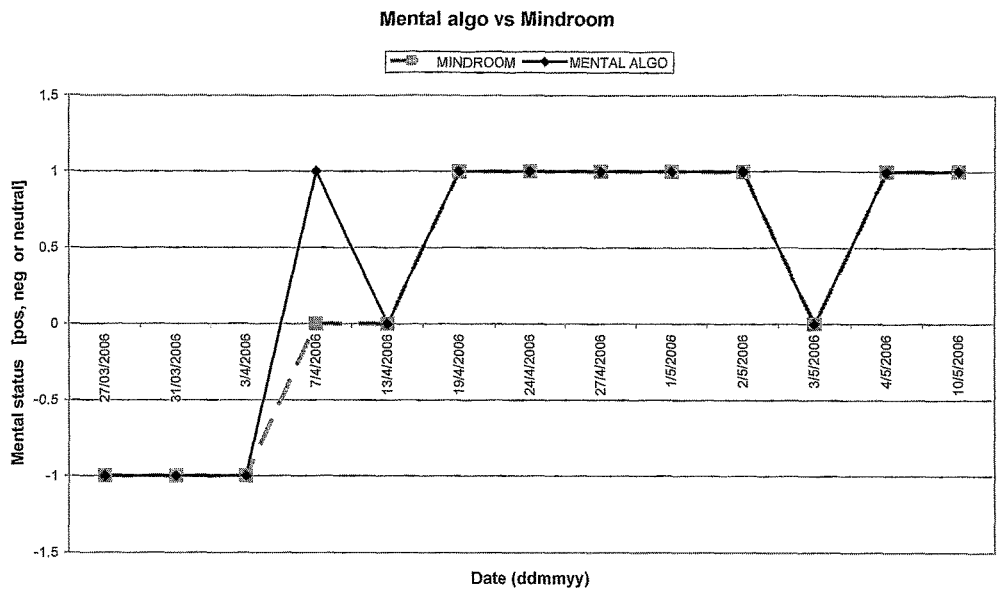

FIG. 13A shows the results of the validation of the method for decomposition of heart rate against reference scoring using traditional parameters not measured continuously on-line. In total, an overall agreement of 94% with traditional parameters is achieved.

Figure 13B:
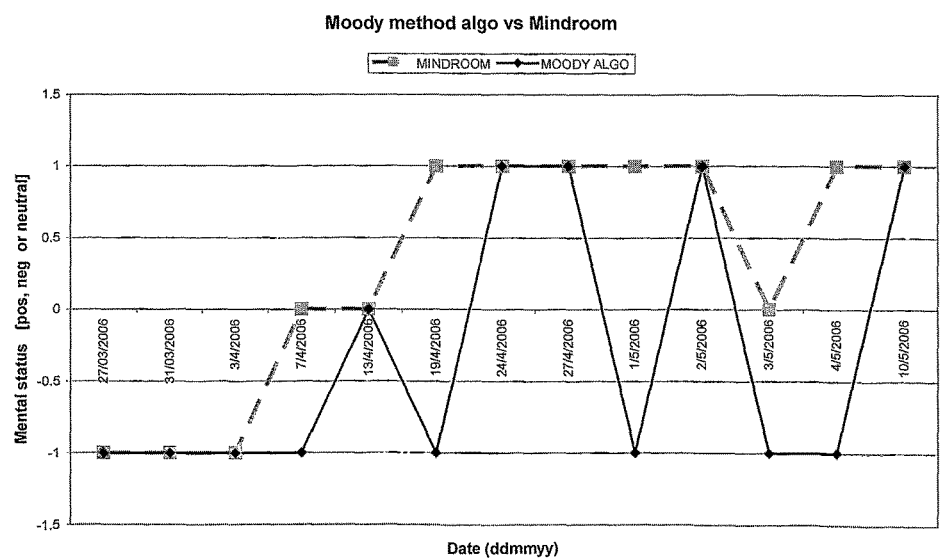

FIG. 13B shows the results of the validation of an existing method for decomposition of heart rate (Moody, 1992) against reference scoring using traditional parameters not measured continuously on-line. In total, an overall agreement of 62% with the Mindroom reference is achieved.

Figure 1:
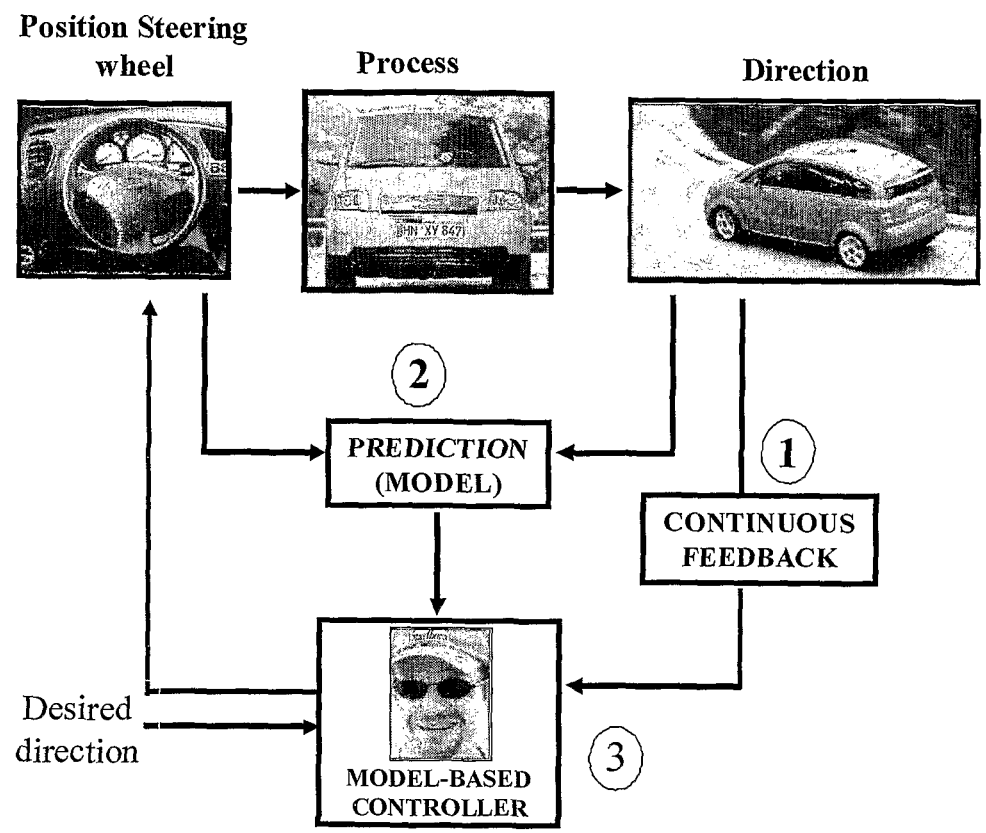
Figure 2:
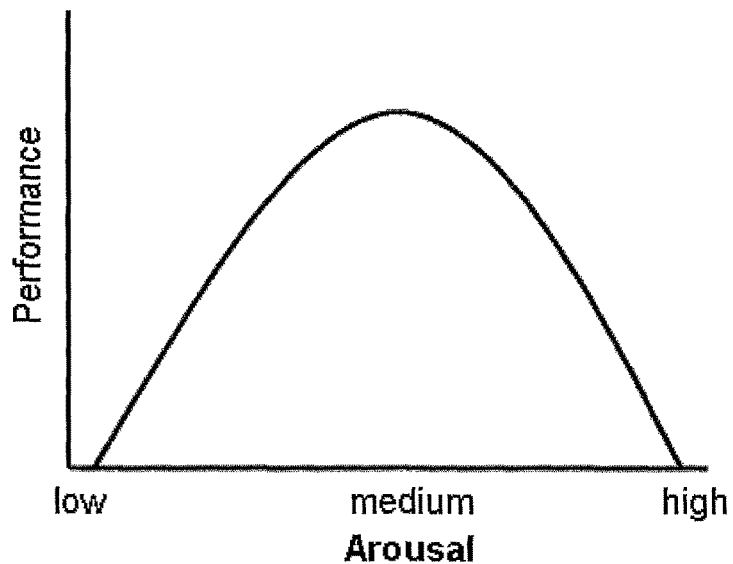
FIG. 2 is a graphical representation of the Yerkes-Dodson law, demonstrating that arousal and performance are linked and that there exists an optimal arousal level to achieve optimal performance for a given task.
Figure 14A:
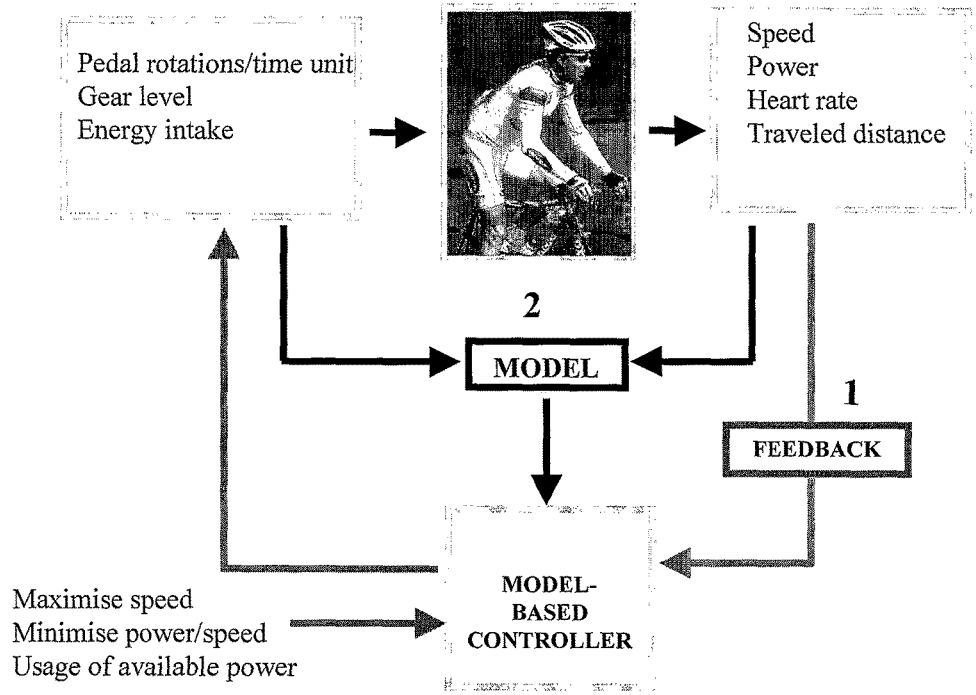

FIG. 14A is a general representation of how bioprocess control can be achieved for the example of a cyclist. The figure does not explicitly show the splitting up of the index of arousal which may be done prior to control (see FIG. 1B), to control the arousal and physical component separately.

Figure 14B:
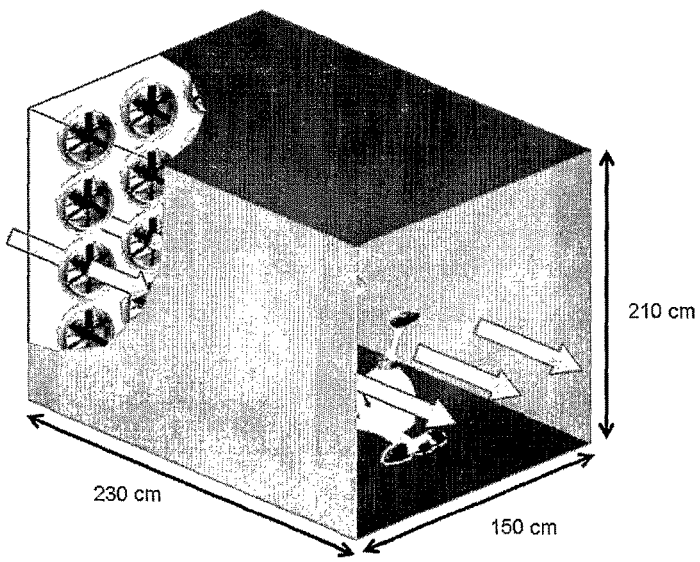

FIG. 14B is a schematic illustration of the wind tunnel and ergometer used in the Examples.

Figure 15:
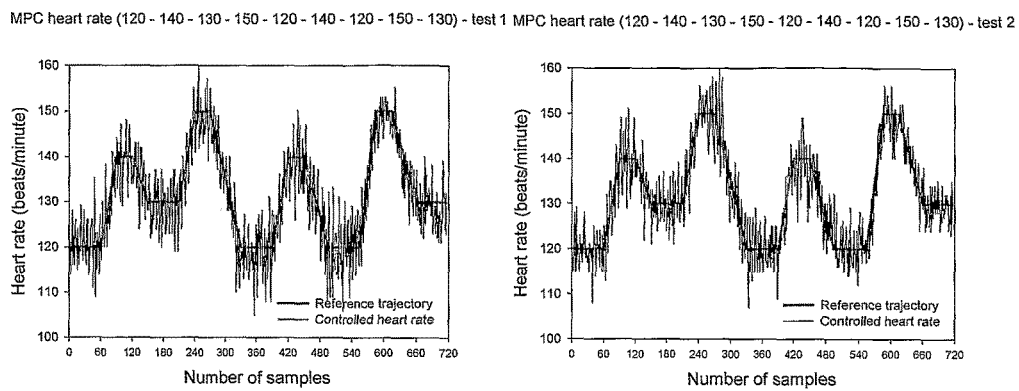

FIG. 15 shows an example of the control of the physical component of heart rate (shown as controlled physical component of heart rate along a reference trajectory).

Figure 16:
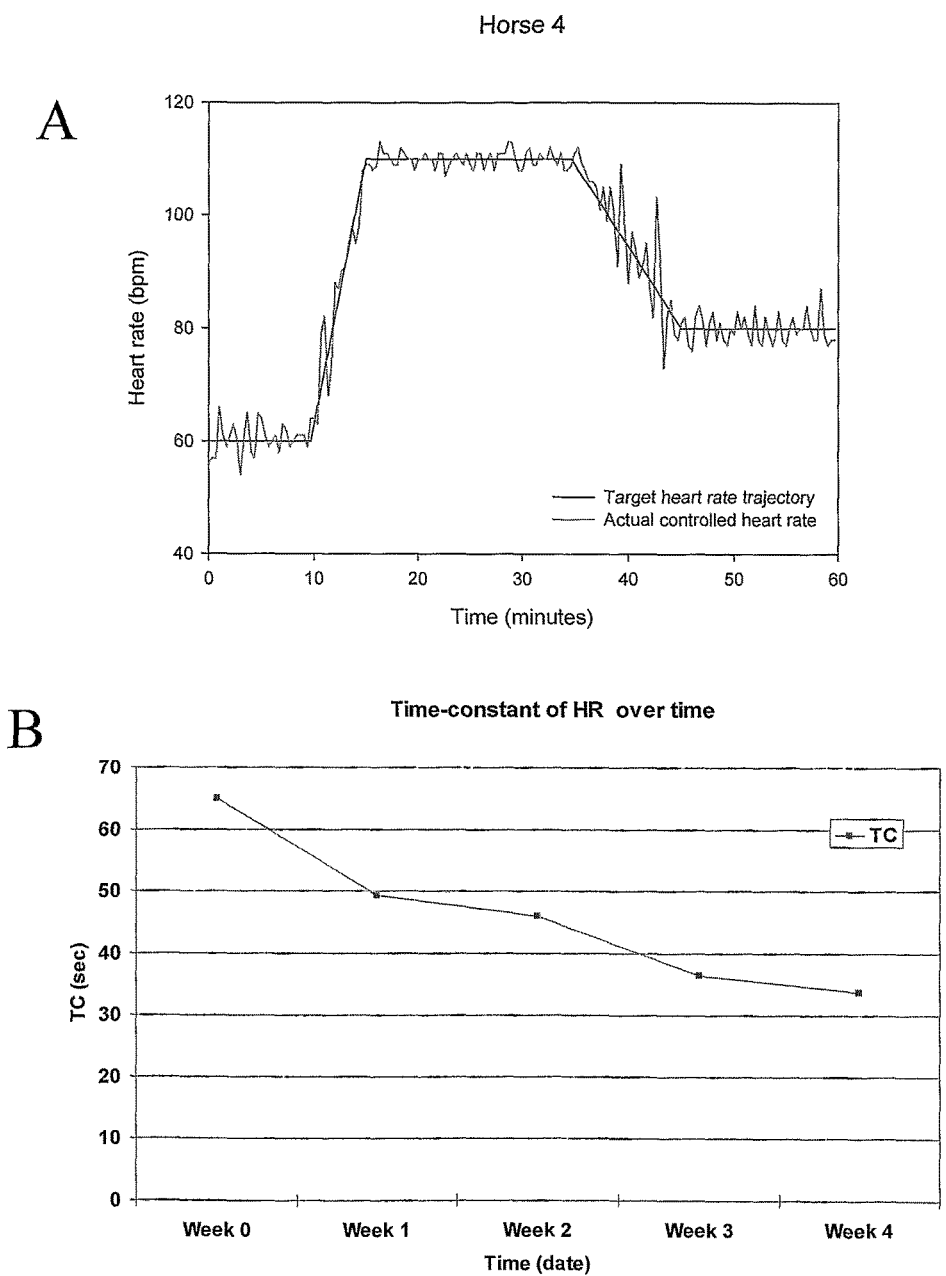

FIG. 16: Panel A shows the target heart rate trajectory for horse 4, together with the heart rate control of the physical heart rate component. Panel B shows that the time constant of heart rate decreases over the weeks training is performed, showing the efficiency of the training method.

Figure 17:
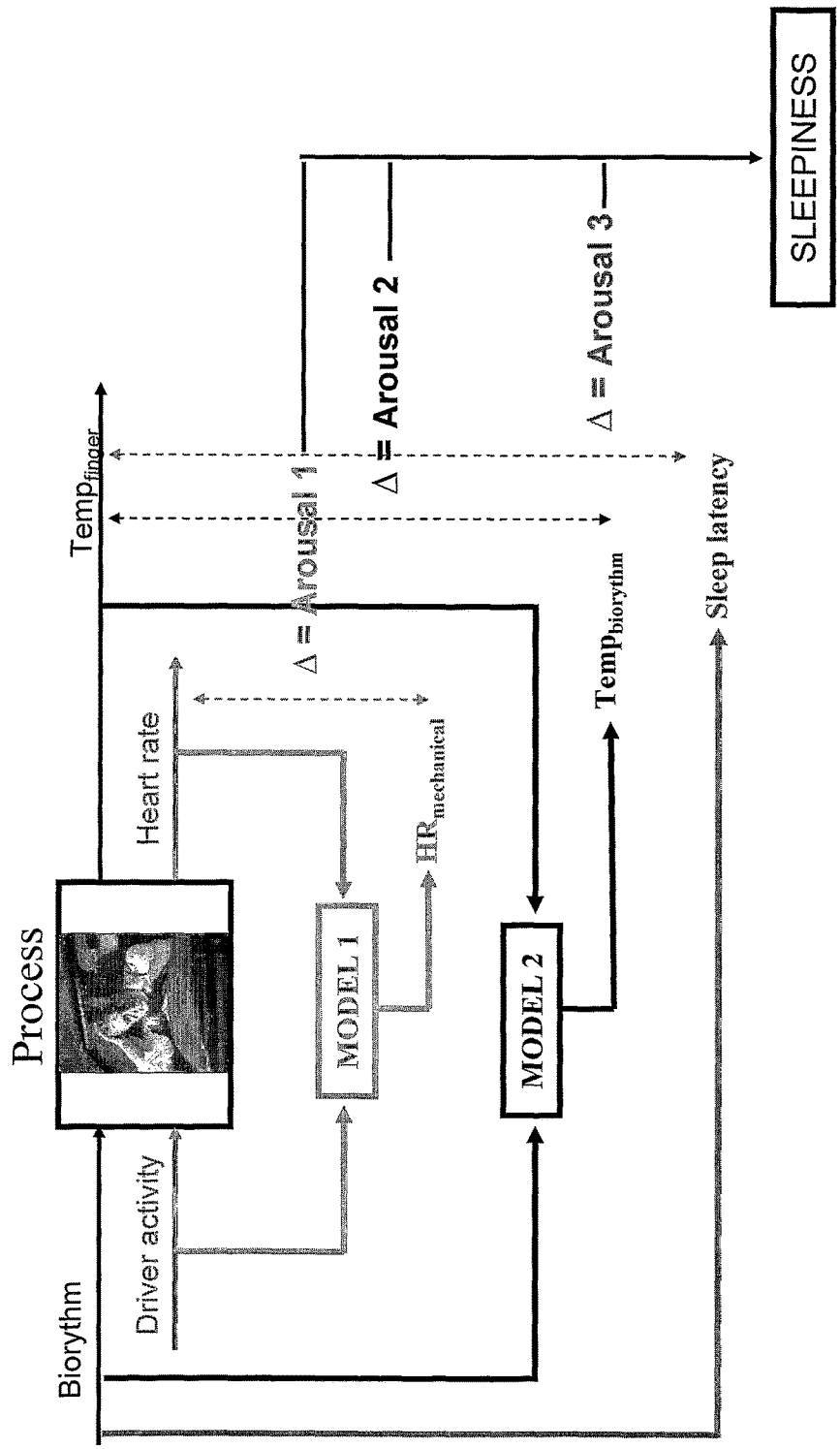

FIG. 17 is a scheme of the global methodology behind the predictive Normal to Excessive Sleepiness in an Active Subject (NESAS) monitor. On the left, in black is the model used for singling out the physical and arousal component of heart rate. The right part of the figure shows how the arousal component of heart rate can be used as input for a second model (here combined with other inputs biorhythm, heat balance and driving performance).

Figure 18:
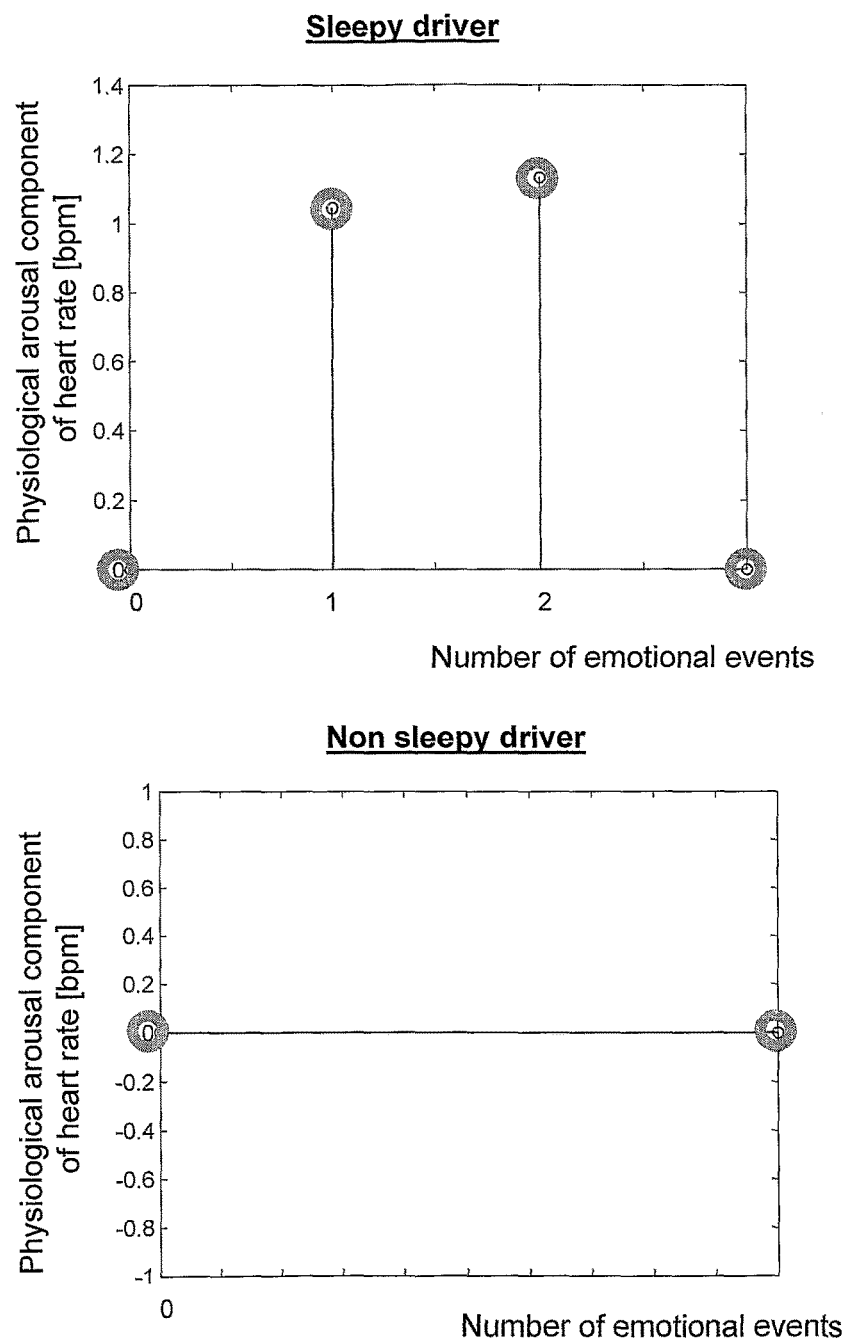

FIG. 18 shows the emotional (arousal) events in the arousal component of heart rate for a sleepy driver (left) and a non sleepy driver (right). The sleepy driver clearly experiences emotional events while driving, indicating a loss of concentration and of alertness. The non sleepy driver experiences not one emotional event during driving a vehicle, indicating high arousal and concentration during his task.

Figure 19:
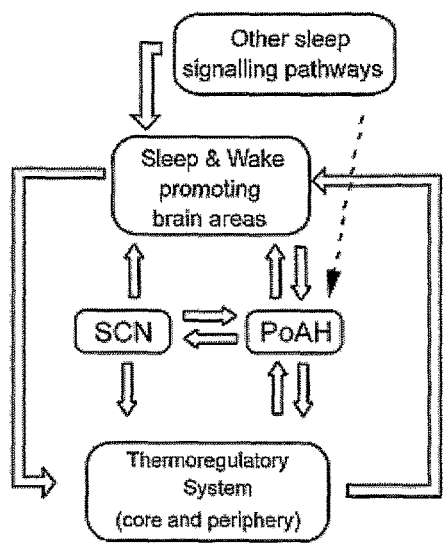

FIG. 19 depicts a scheme on the positive feedback connection between thermoregulation and sleep onset (Gilbert et al., 2004, after Van Someren, 2000) with the internal circadian pacemaker SCN (suprachiasmatic nuclei) and control site for thermoregulation PoAH (Pre-optic Anterior Hypothalamus).

Figure 20:
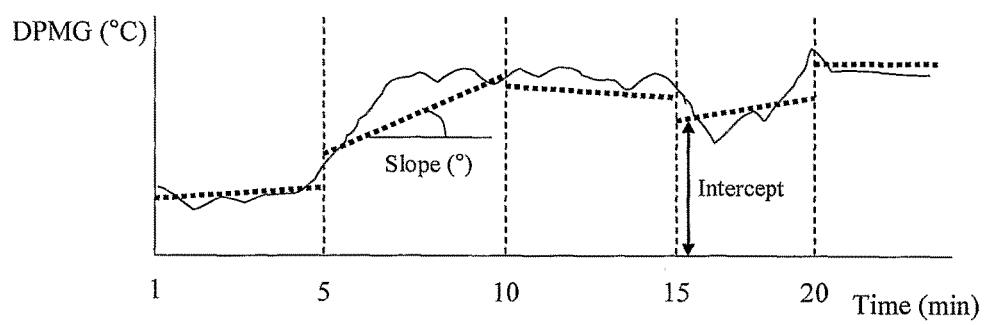

FIG. 20 is a graph exemplifying a dynamic auto regression technique for detecting signs of sleepiness in the Distal-to-Proximal-to-Microenvironmental Gradient (DPMG). The full line represents the measured DPMG and the dotted line represents the dynamic auto regression model for 5 minute time window. Both the intercept and the slope per 5 minute time window are indicative of the dynamic course of DPMG.

Figure 21:
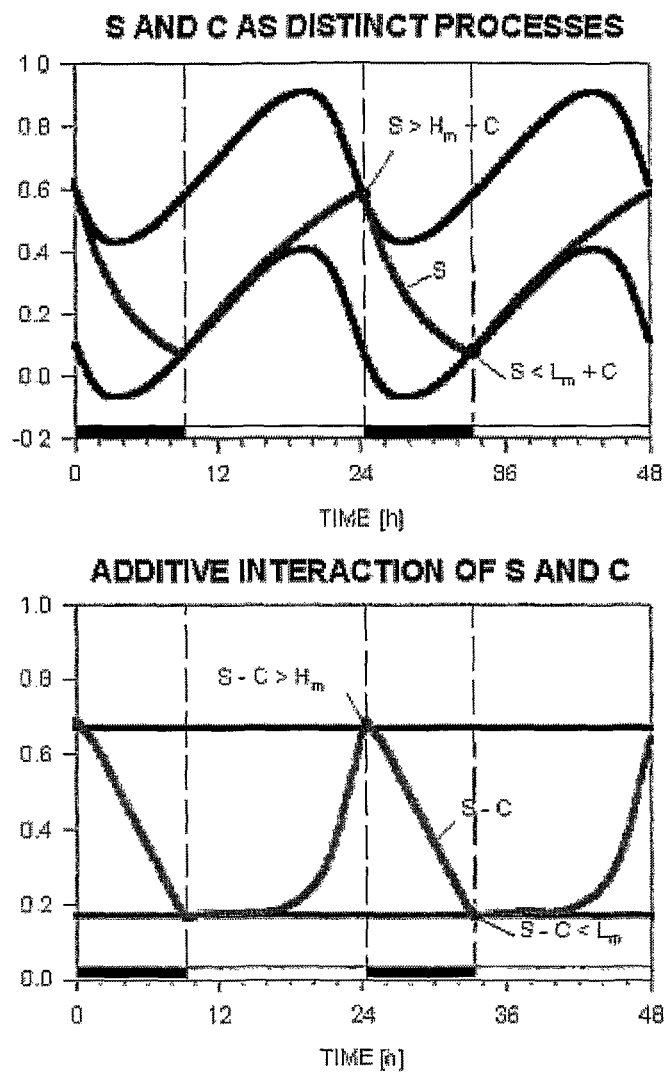

FIG. 21: Simulation of the timing of sleep and wake by the two process model of sleep regulation. Top: Representation of S and C as two distinct processes. The homeostatic process S oscillates between two thresholds (H and L; mean level $H_m$ and $L_m$) modulated by a circadian process. Bottom: Representation of S and C as a single process after additive interaction. From Achermann & Borbely (1992).

Figure 22:
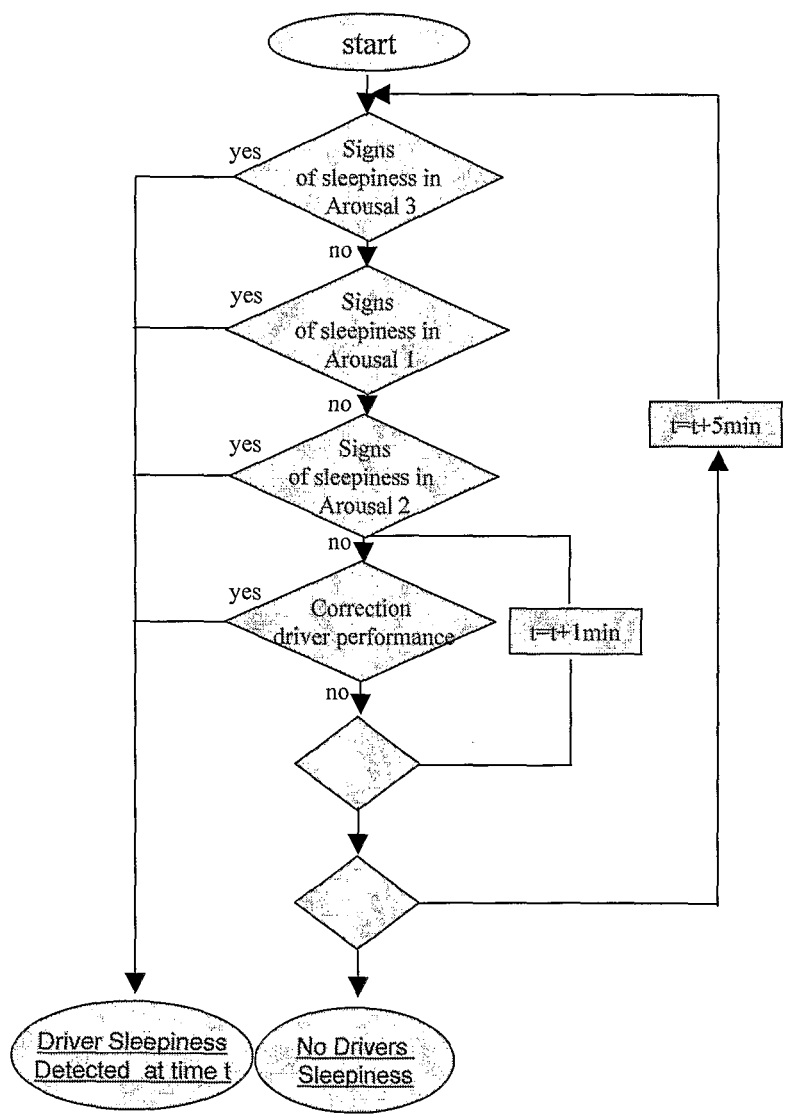

FIG. 22 shows a flowchart of the driver sleepiness/NESAS detection algorithm. The basis is detection of signs of sleepiness in the 3 indices of arousal (FIG. 15) being individual and time-variant arousal component of heart rate (Arousal 1), Distal to-Proximal-to-Microenvironmental Gradient DPMG (Arousal 2) and Bio-rhythm (Arousal 3). A correction term based on driving performance in also included.

Figure 23:
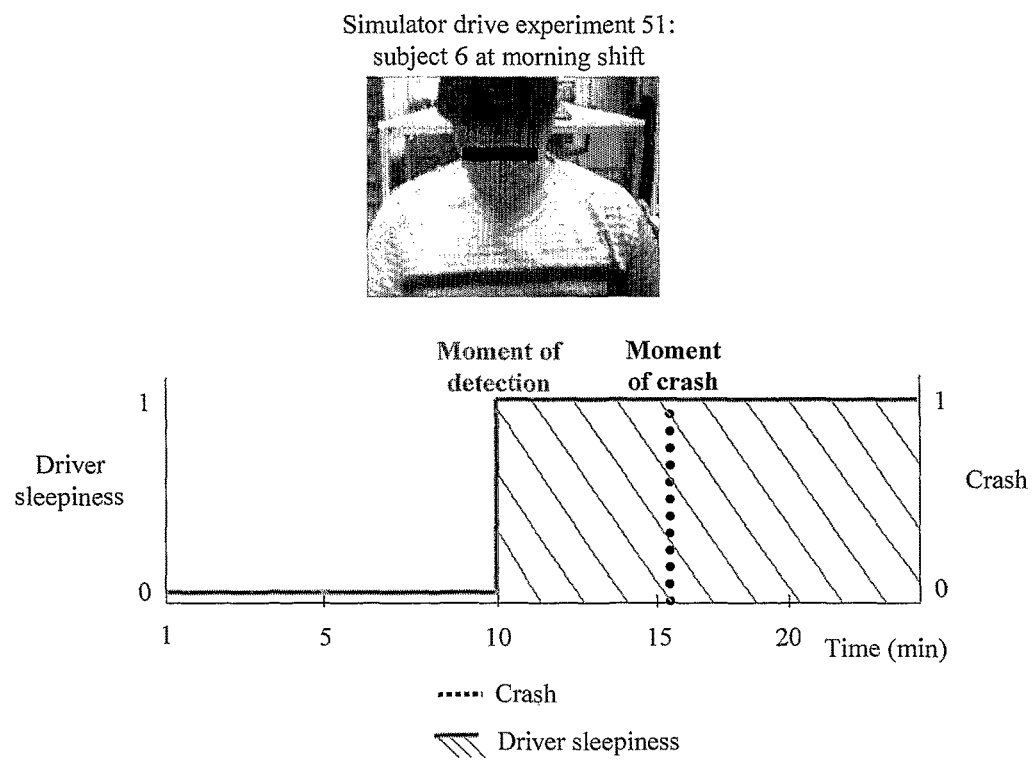

FIG. 23: Predictive power of the algorithm for one specific simulator driver. During the 25 minute simulator drive (x-axis), the sleepy subject crashes at 15 min 20 s (dotted line, right y-axis) and driver sleepiness is detected at 10 min (grey line, left y-axis) resulting in a predictive window of a crash for over 5 minutes.

Figure 24A:
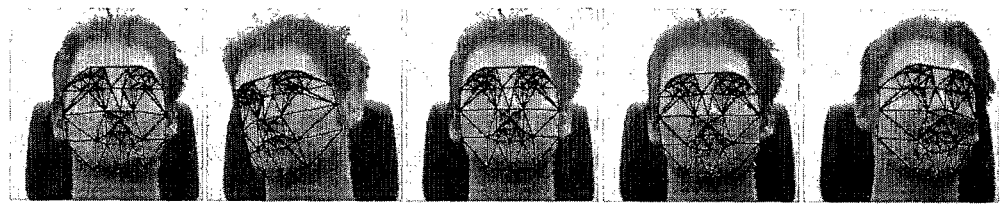

FIG. 24A shows an example of frames from the driving simulator footage with an overlay of the automatically detected facial features.

Figure 24B:
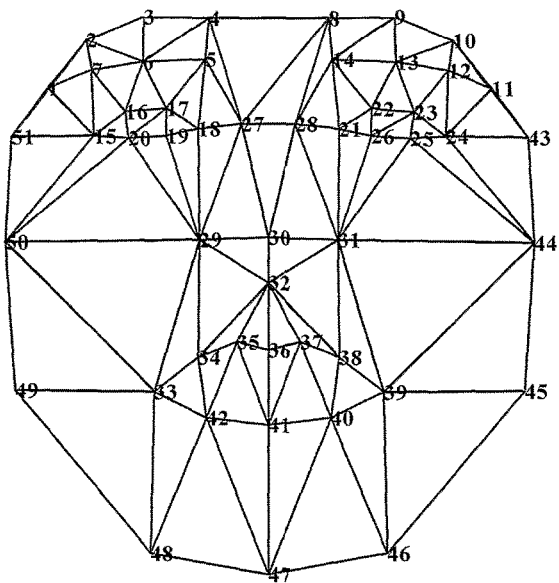

FIG. 24B represents the face mask of automatically detected facial features with an indication of 51 feature points.

Figure 25:
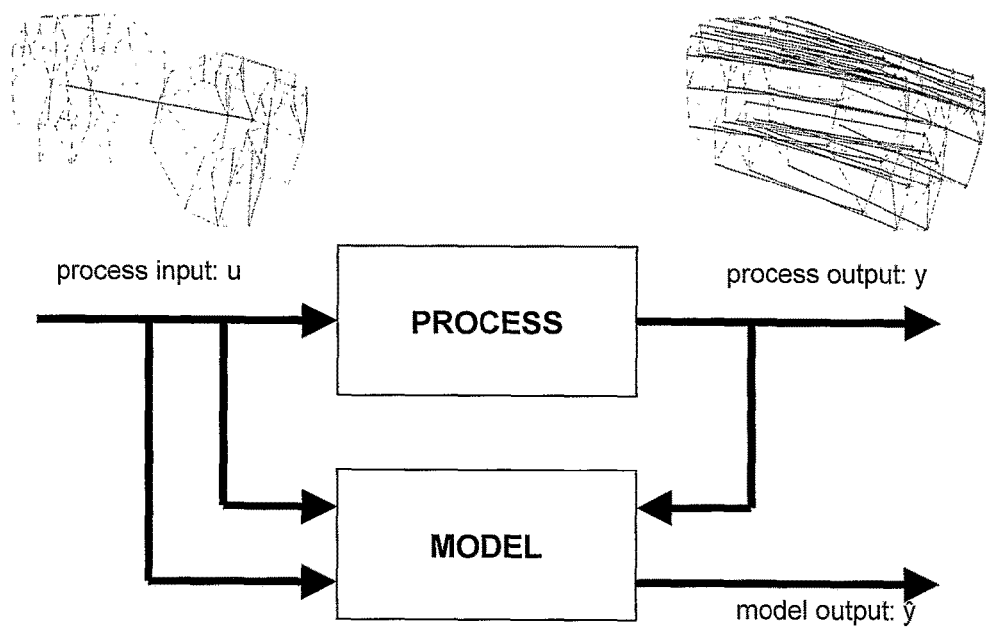

FIG. 25 shows a schematic overview of the model used for automatic image analysis of facial movement. A model was identified as the relation between the process input u and the process output y. This model generates an output ŷ which approximates the part of y directly related to the process input u.

Figure 26:
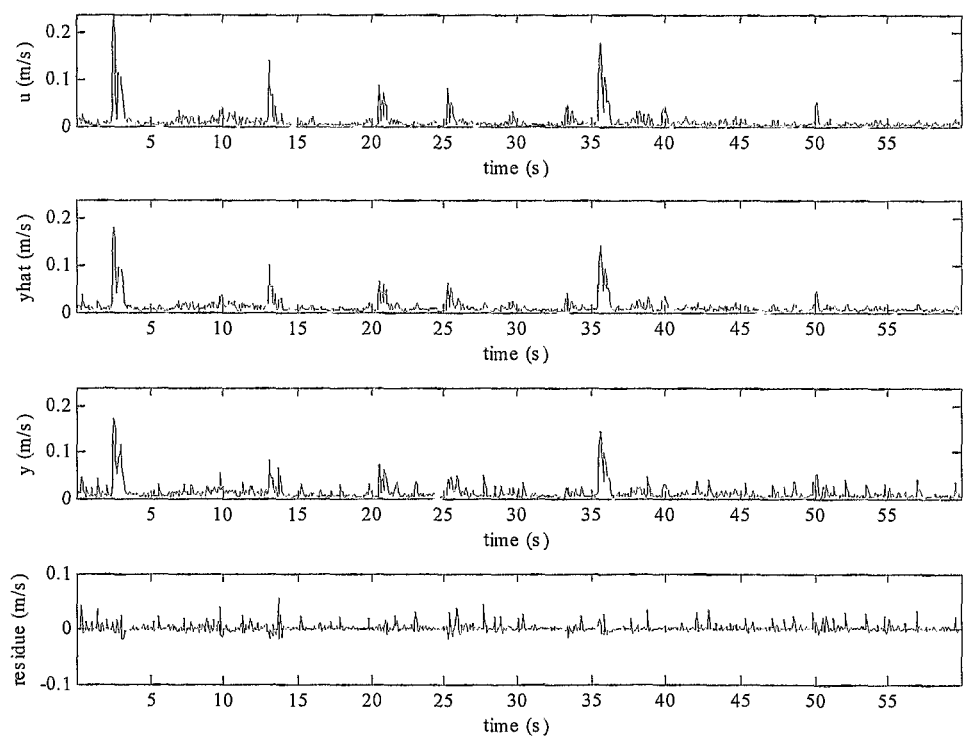

FIG. 26 displays the values of process input u, process output y, model output ŷ and the difference between the latter two over time. Top panel: the process input u; second panel: the model output ŷ; third panel: the process output y; and bottom panel: the residue as the difference between y and ŷ.

Figure 27:
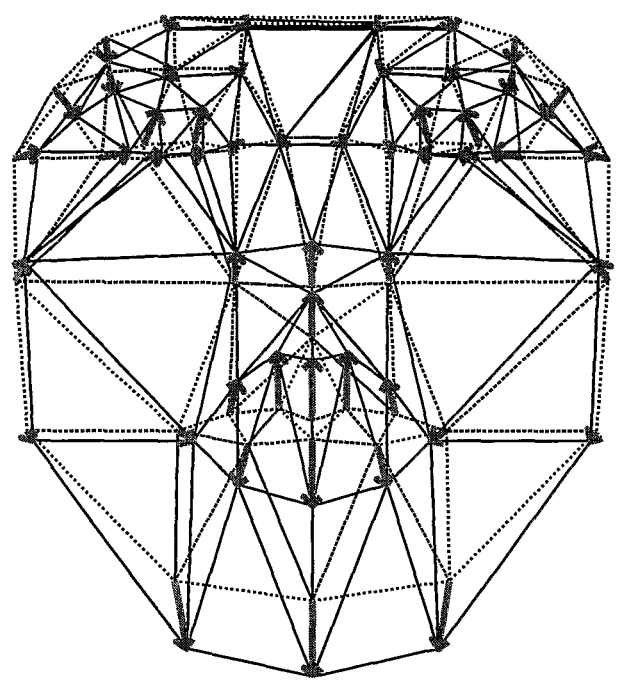

FIG. 27 illustrates the movement of the facial features, after the rigid head movement is eliminated. This remaining movement is caused by facial expression (the mental/arousal component of face movement).

Figure 28:
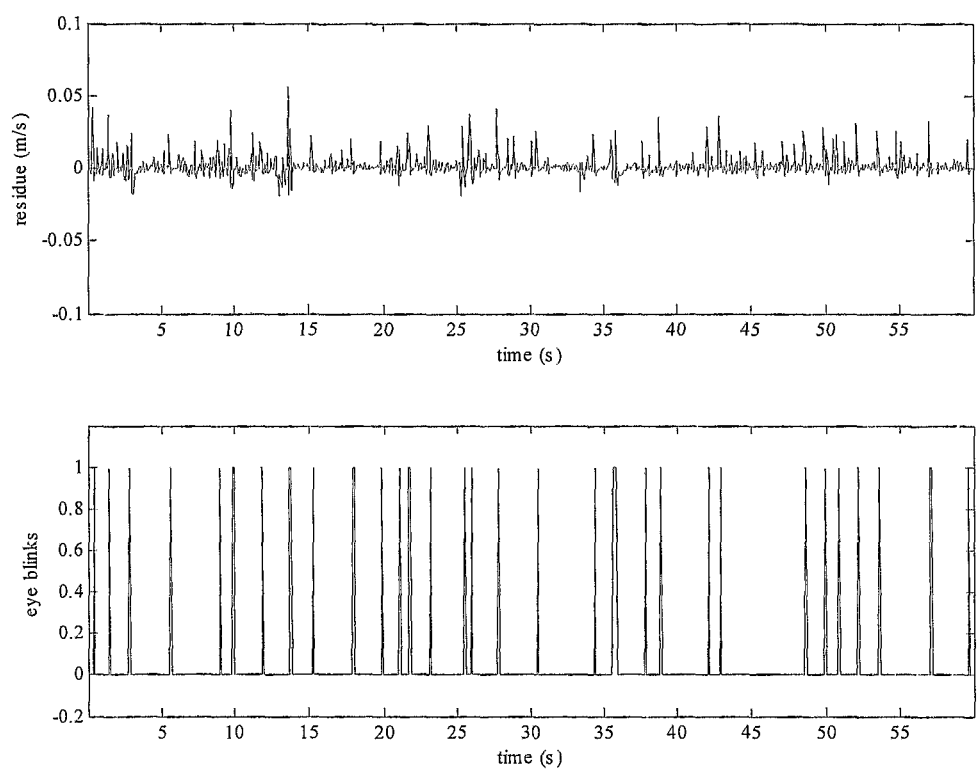

FIG. 28 shows the feasibility of detecting facial expression changes by image analysis, by automatic detection of eye blinks. Top panel: the model residue (i.e. the arousal component of head movement). Bottom panel: detected eye blinks as function of time.

Figure 29:
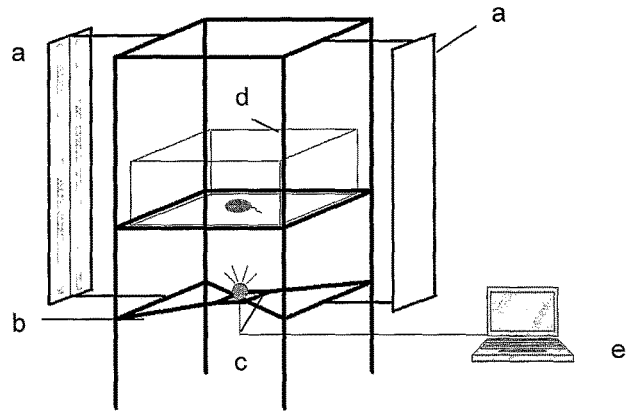

FIG. 29 is a schematic overview of the measurement installation for analyzing body movement of a mouse using image analysis. The mouse was placed in a transparent cage with a camera below. a: light-box; b: metal framework; c: camera; d: cage and mouse; e: laptop.

Figure 30:
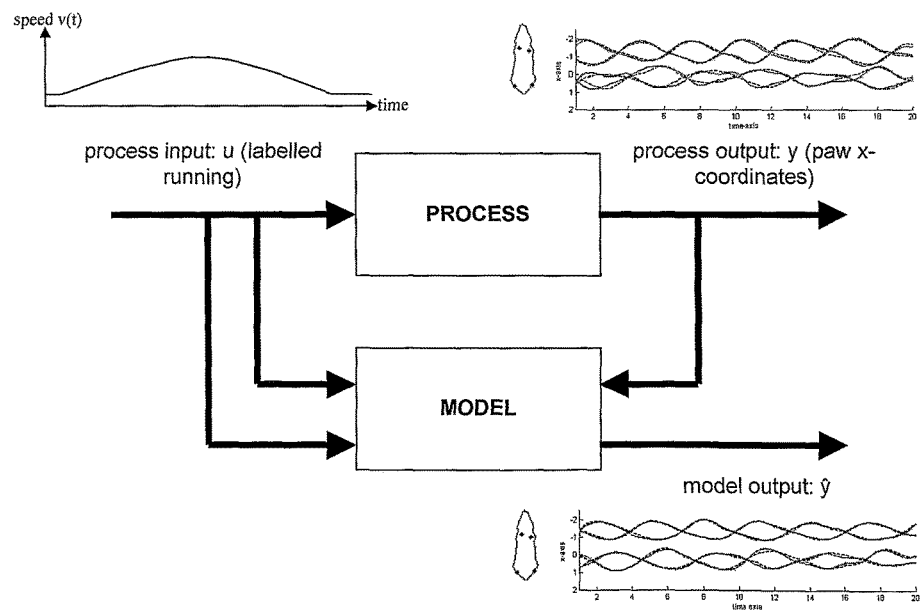

FIG. 30 shows a schematic overview of the model used for monitoring body movement of a mouse using image analysis. A model was identified as the relation between the process input u (labelled running) and the process output y (paw x coordinates). This model generates an output ŷ which approximates the part of y directly related to the process input u. This corresponds to the physical component of running, while the difference between the model output and the process output is representative of movement due to arousal.

Figure 31:
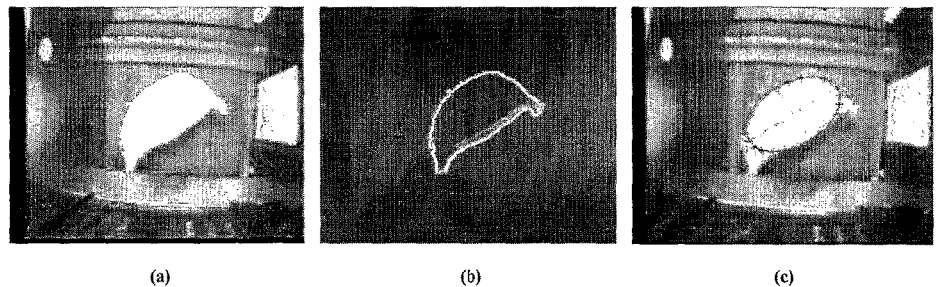

FIG. 31 shows an example of frames from the chicken footage with an overlay of the automatically detected facial features.

Figure 32:
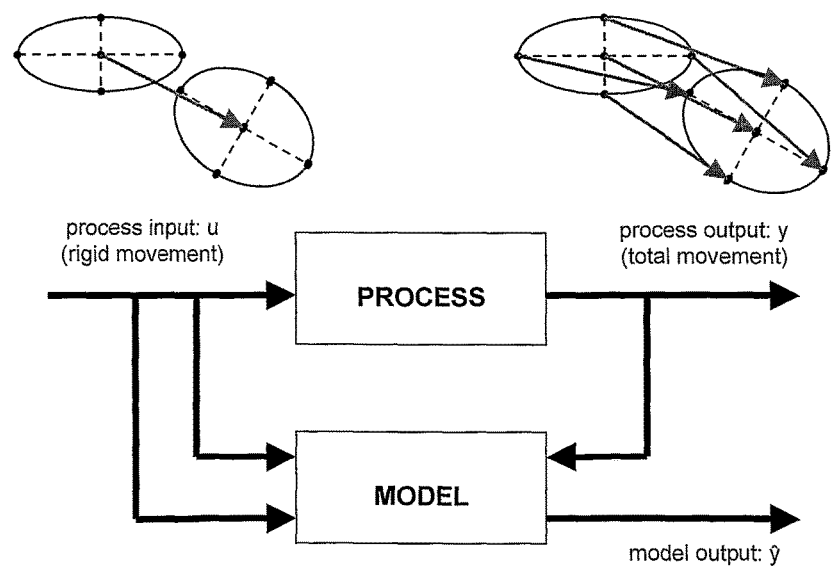

FIG. 32 shows a schematic overview of the model used for automatic image analysis of chicken movement. A model was identified as the relation between the process input u and the process output y. This model generates an output ŷ which approximates the part of y directly related to the process input u.

Figure 33:
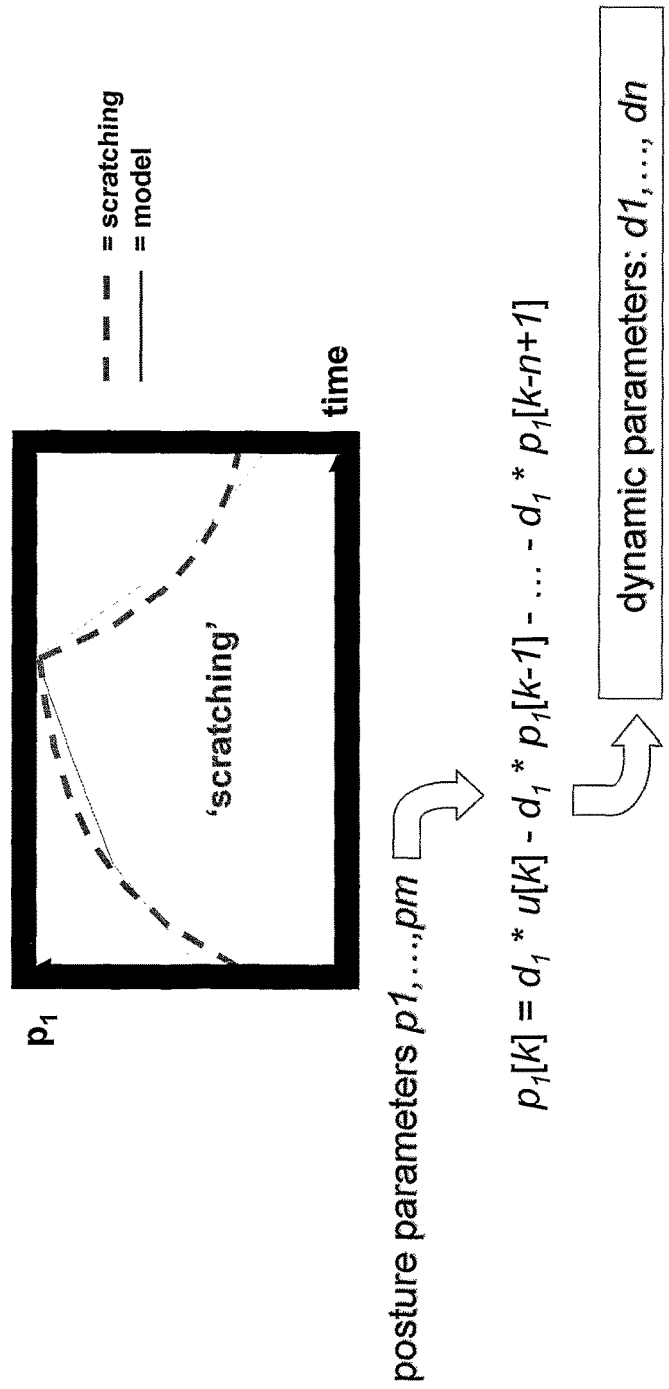

FIG. 33 shows the second model for the dynamic behaviour of the posture parameters.

Figure 34:
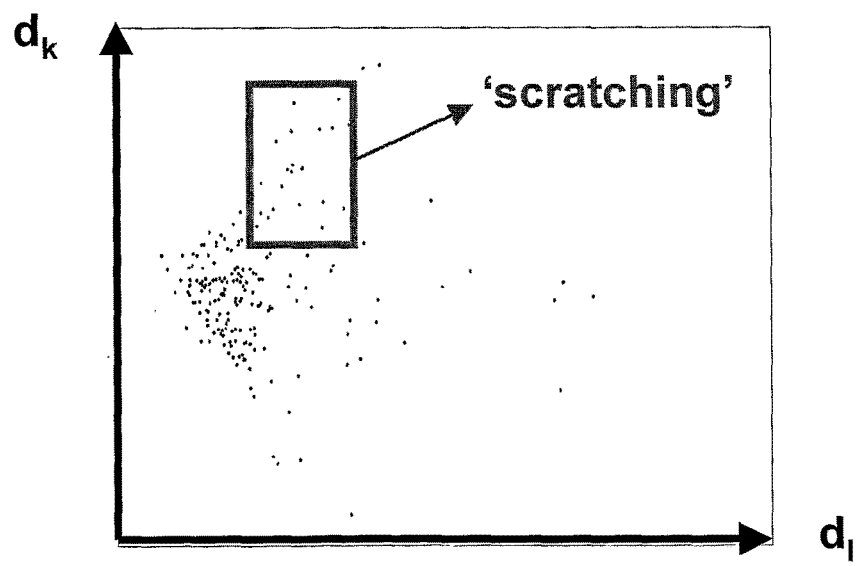

FIG. 34 shows the automatic classification of individual training behaviour.

Figure 35:
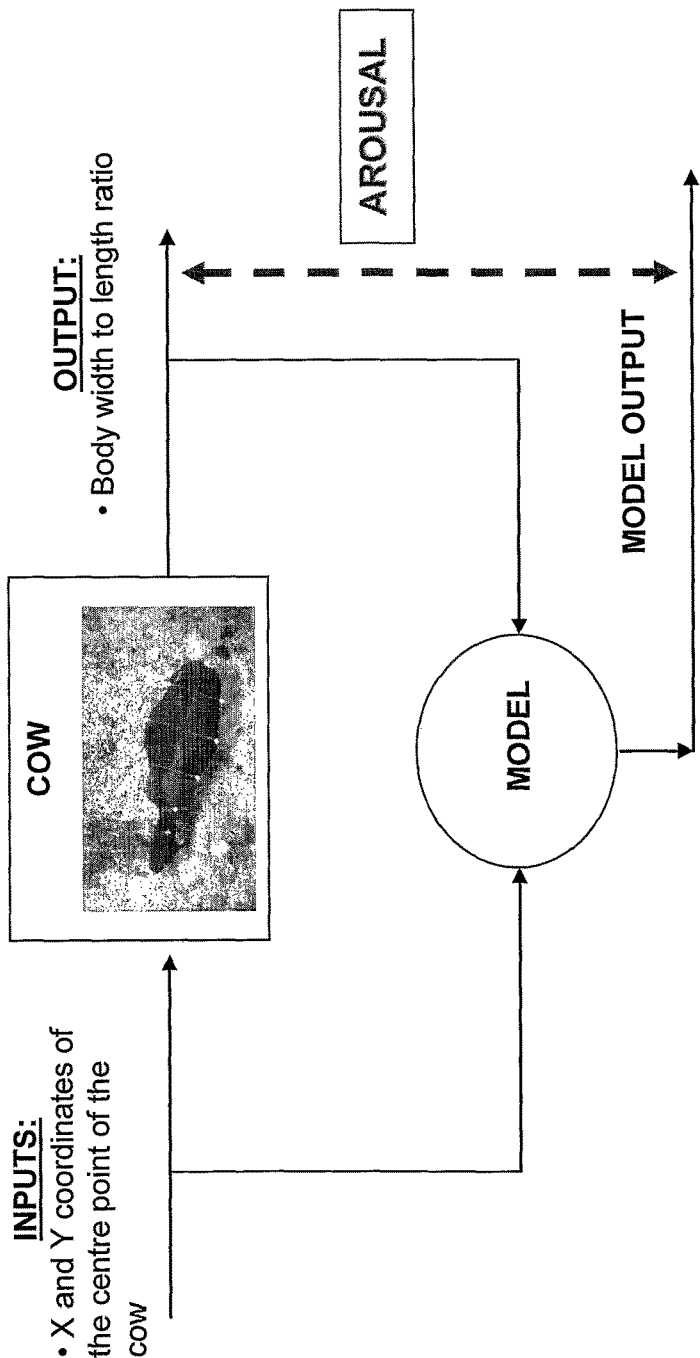

FIG. 35 shows a schematic overview of the model used for monitoring calving of cows using image analysis. A model was identified as the relation between the process input u (general movement: x and y coordinates of the centre point of the cow) and the process output y (body width to length ratio). This model generates an output ŷ which approximates the part of y directly related to the process input u. This corresponds to the physical component of general movement, while the difference between the model output and the process output is representative of movement due to arousal.

Figure 36:
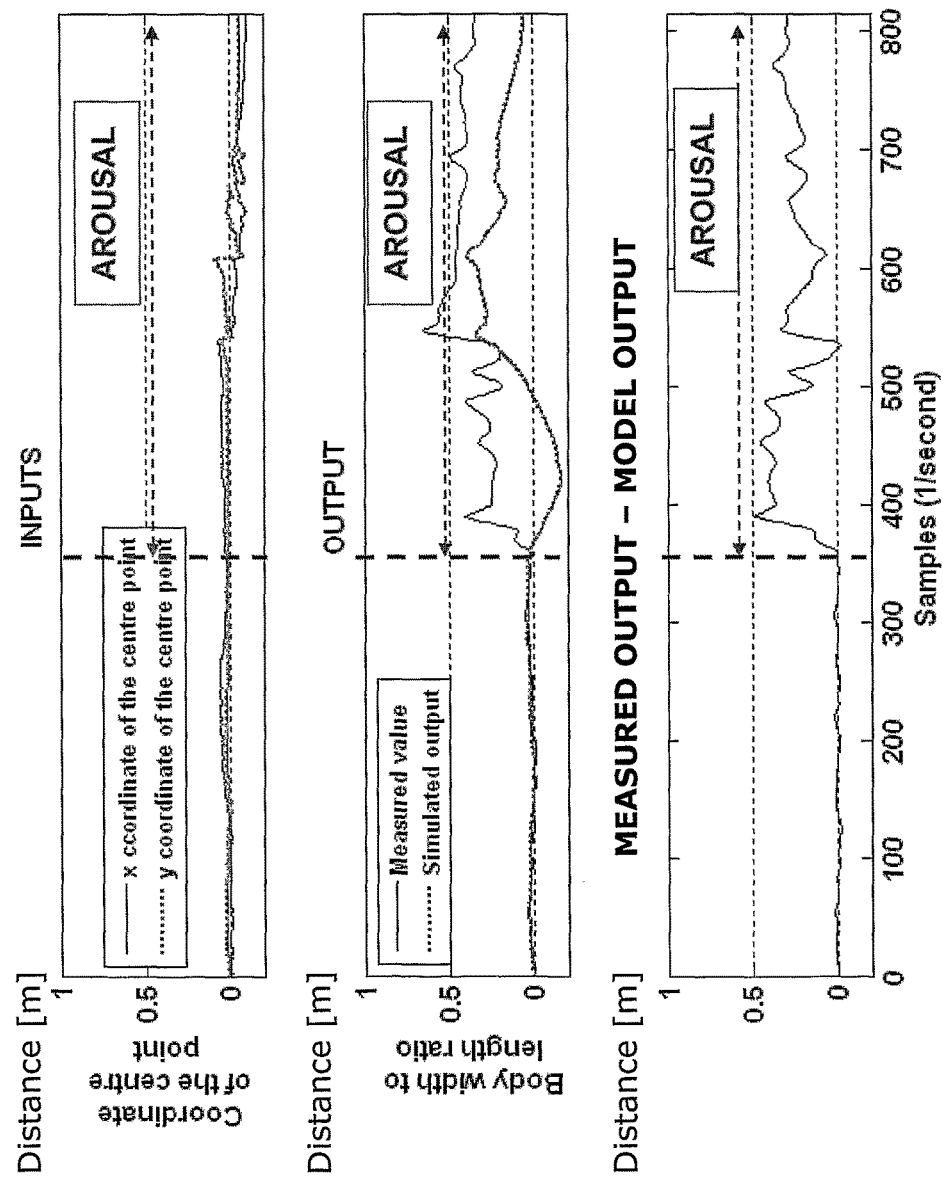

FIG. 36 shows the results of the calving monitor on a cow giving birth. The upper plots shows the dynamic course in the input variable general movement (x and y coordinates of the centre point of the cow). The middle plot shows the output variable containing and index of arousal (body width to length).

Figure 37:
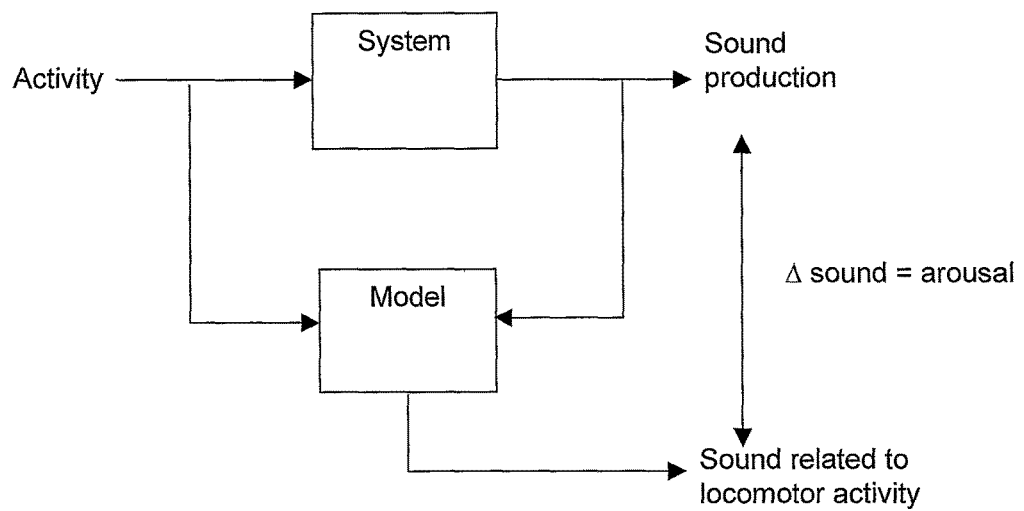

FIG. 37. Principle of model-based detection of arousal in sound signals.

Figure 38:
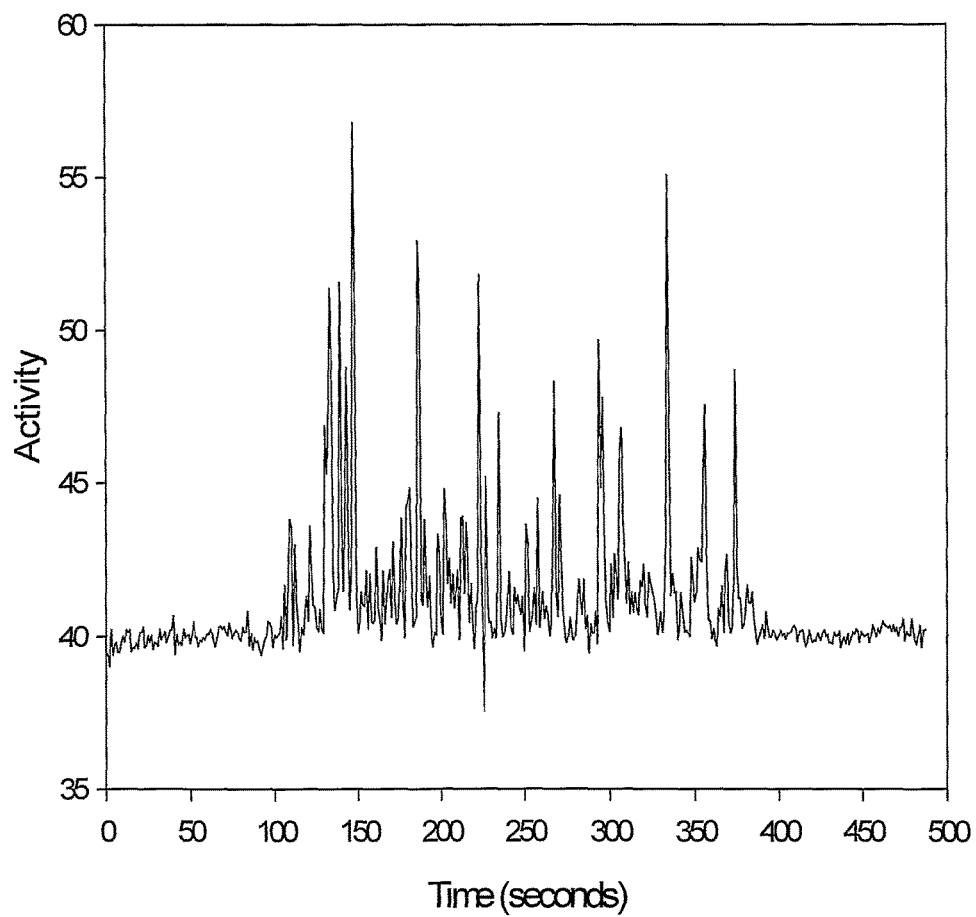

FIG. 38. Time series of calculated activity of the stallion based on the 3D accelerometer measurements.

Figure 39:
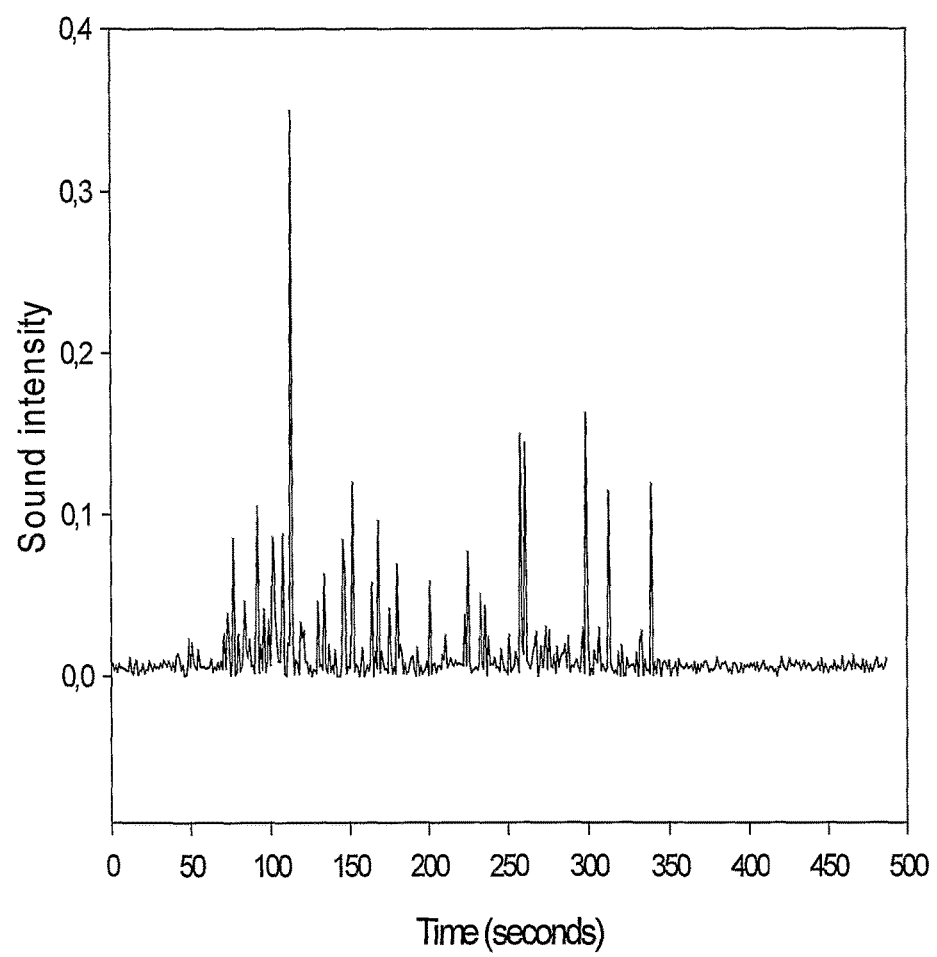

FIG. 39. Time series of measured sound intensity of the stallion.

Figure 40:
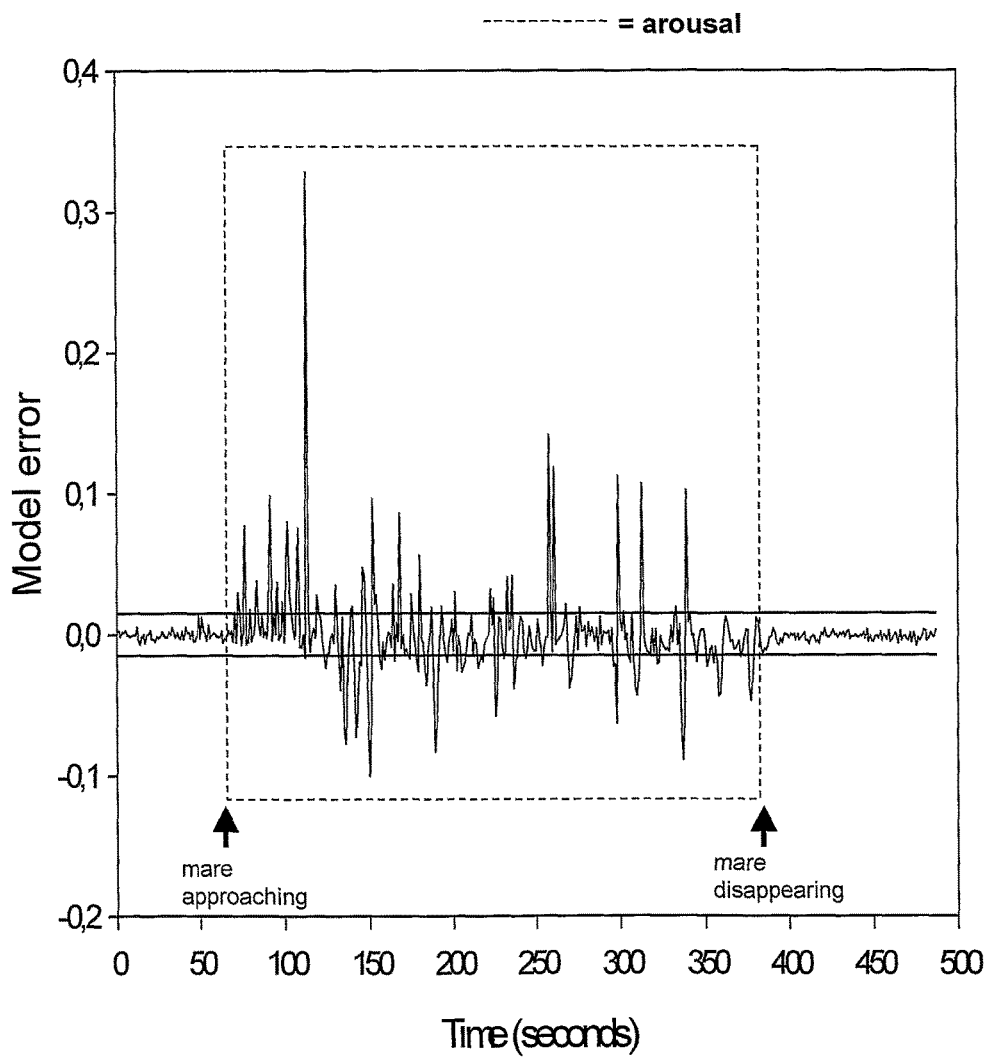

FIG. 40. Time series of the model errors. The stallion was in contact with the mare from seconds 53 until 355 (indicated by the arrows). The episodes of arousal are defined as the periods in the error signal when passing the thresholds.

DETAILED DESCRIPTION OF THE INVENTION

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. These definitions should not be construed to have a scope less than understood by a person of ordinary skill in the art.

Definitions

The term "status" of an individual human or animal is an indication of how an individual living organism acts, behaves, and/or feels at a given moment and is used herein to refer to the health status, behavioural status, mental status, emotional status, physiological status, psychological status, psychophysiological status, cognitive status or physical status of individual human beings or individual animals. It relates to the monitoring of bioprocesses of the individual and linking the values of bioprocesses inputs and/or outputs to the status of the individual. The term "animal" as used throughout the application includes all multicellular organisms from the kingdom Animalia (or Metazoa). Unless explicitly mentioned otherwise, it thus also includes humans. However, to comply with more conventional language, the application often refers to an individual human or animal. This should not be interpreted as limiting the scope of the word animal. The same consideration applies to "vertebrate animal" or "mammal".

"Bioprocess inputs" as used throughout the application refers to factors which can affect the dynamical behaviour or the course of a bioprocess or the dynamic behaviour of the status of the individual and can be used as input into the model. These bioprocess inputs may be properties of the individual itself (e.g. ECG, biorhythm, heat balance, . . . ) as well as external variables (e.g. food intake, training activity, . . . ). In order to be able to use them as an input to a real-time model of a CITD living organism, it is necessary that these factors are measurable, i.e. can be quantified and/or described in a way suitable for input in the model. A non-limiting list of examples of bioprocess inputs is included in the specification.

"Bioprocess outputs" or "bioresponses" as used throughout the application refers to factors which are the result of a bioprocess of the individual and can be measured, or estimated by the model on the basis of one or more bioprocess inputs. These bioprocess outputs may be properties of the individual itself (e.g. heart rate, body temperature, sleepiness, . . . ) as well as external variables (e.g. travelled distance, speed, . . . ). A non-limiting list of examples of bioprocess outputs or "bioresponses" envisaged for use in the methods according to particular embodiments is provided in the description. Like the bioprocess inputs, these factors are measurable, i.e. can be quantified and/or described by the model. As the mathematical model identifies and quantifies the relation between bioprocess inputs and bioprocess outputs, control of the bioprocess outputs (e.g. towards a predefined, desired value or along a predefined trajectory) can be achieved by adapting the bioprocess inputs. Alternatively, this control can be achieved by adapting one or more environmental variables, which will change the relationship between bioprocess input and output. Depending on the bioprocess that is monitored and the variables that are measured, a variable may sometimes be considered as bioprocess input, sometimes as bioprocess output, the terms are not mutually exclusive.

A "model input" as used in the application can be any variable that is used as input into the model, e.g. a bioprocess input or bioprocess output.

A "model output" is the expected process output as a relation to the model input, described by the model. Typically, when the model describes a bioprocess and the model input is a bioprocess input, the model output will be an estimation of the bioprocess output, based on the model input.

The term "environment" or "environmental variable" refers to all variables that are not considered as bioprocess inputs or outputs of a living organism for a given bioprocess, but that can influence the status of a living organism. Depending on how the bioprocess (and its in- and outputs) is defined, metabolism related variables that may be used as bioprocess input or output for a given bioprocess may be regarded as environmental variables for another bioprocess (or the same bioprocess, but with differently defined inputs and/or outputs). Environmental variables are for example temperature, humidity, physical variables not used as bioprocess in- or output, illness, food, medication, social variables, stressors etc.

The term "disturbing variable" as used in the application refers to a subset of environmental variables. Disturbing variables are all variables that can have an effect on the considered bioprocess or that can influence the status of a living organism and that cannot be adapted or controlled in a controllable manner, such as (but not limited to) outside temperature, weather conditions, and pollution. Thus, disturbing variables can not be changed to control the bioprocess output, while environmental variables that are not disturbing variables in principle can be used for control purposes. However, effective control using environmental variables requires that these variables are measured, in order to change the bioprocess in a controlled way.

Depending on what variables one monitors as an input or output of the bioprocess, one considers all other variables that are not measured but that can influence the bioprocess as environmental variables. If controllable environmental variables are not measured on-line, they will typically not be used for control purposes. In this specific case, there is only a theoretical difference between environmental and disturbing variables, as in practice neither variable will be used for control purposes. Environmental variables that are not measured are referred to as 'external disturbances' throughout the application, irrespective of their potential use for control purposes (i.e. 'external disturbances' include both disturbing and non-disturbing variables). External only refers to the fact that these variables are not directly used as model input or output, as variables of the monitored individual human or animal may be external disturbances (e.g. illness, food intake, effect of medication). When measuring for example the speed of a cyclist as an input and the heart rate as an output, all other variables like temperature, pressure of the tires, used gear on the bike, food intake, etc can be considered external disturbances in the real time model if they are not measured.

The term "metabolism related variable of the human or animal" as used throughout the application refers to variables relating to the metabolic energy used or mobilized by the individual human or animal. These variables may be properties of the individual animal (e.g. hormone or neurotransmitter concentration, ECG, power production), but can also be external variables, e.g. training activity, cycling speed. Thus, the term includes variables that will influence metabolic energy (e.g. training activity) as well as variables that reflect or are influenced by the mobilization of metabolic energy (e.g. hormone or neurotransmitter concentration, ECG, power production).

The term "performance related variable of the human or animal" as used in the application refers to variables directly relating to physical or cognitive performance, i.e. variables linked to a cognitive or motor task or the execution thereof. Performance can be defined as the capacity to achieve a desired result. These variables may be properties of the individual animal (e.g. ECG, power production), but can also be external variables, e.g. training activity, cycling speed. The term thus includes variables that will influence performance of the individual (e.g. training activity), as well as variables that reflect or are influenced by performance of the individual (e.g. power production, ECG).

As the execution of a task always requires metabolic energy of the individual human or animal, all performance related variables will necessarily also be metabolism related variables.

An "arousal variable" or "variable relating to an index of arousal", as used in the application, refers to a variable that is indicative of the state of arousal of the individual. A "variable relating to an index of arousal" can also be described as "variable containing an index of arousal". The "index of arousal" that is contained in this arousal variable is the 'arousal component' of the variable, i.e. the component that is due to arousal and not to e.g. physical activity. "Arousal" can be defined as the ability to mobilize metabolic energy to meet environmental or internal demands on behaviour (see "Encyclopedia of the human brain", Academic Press, 2002). Arousal is a well understood term. A variable containing an index of arousal thus is necessarily a variable of the individual self and not an external variable. Consequently, the component of the arousal variable that is estimated by the model is a physical component, typically (but not necessarily) a mechanical component. Arousal variables are well known in the art and include e.g. cortical EEG, heart rate, electrodermal responses, changes in blood chemistry, changes in early gene expression, facial expression, behaviour, sound production by the living organism. A non-limiting list of suitable examples of variables relating to or containing an index of arousal is included in the specification.

It should be noted that arousal is often further divided into two components, but the way it is divided differs. A first distinction is made between 'cognitive (or cortical) arousal' and 'physiological arousal', which can be defined as the arousal required for an intellectually demanding task or a physically demanding task, respectively. When referring to 'arousal' in the application, it is intended to include both these categories, unless explicitly stated otherwise.

Sometimes, however, a distinction is made between 'physiological arousal' and 'psychological (or emotional) arousal', wherein the former refers to all physiological manifestations of arousal (e.g. skin conductivity, EEG), while the latter relates to psychological manifestations, i.e. all subjective, non-measurable feelings of arousal, typically assessed by subjective questionnaires. As only the physiological manifestations of arousal are measurable (e.g. by monitoring an index of arousal), 'arousal', as used throughout the application, in this case corresponds to 'physiological arousal'. However, this should not be interpreted restrictively, as most psychological manifestations also are reflected in physiology (e.g. heart rate, sweating, EEG activity). It merely means that arousal should be interpreted as a state that is physiologically measurable in an objective way, not as a term that can only be interpreted subjectively. Thus, "physiological arousal" as used in the application refers to all physiological and measurable manifestations of arousal (e.g. increased heart rate, change in skin conductance, difference in brain activity as measurable by EEG, . . . ), and (physiological) arousal is meant to include the physiological manifestations of psychological or emotional arousal. In practice, this means that physiological variables (such as heart rate, skin conductance, blood pressure, . . . ) can be used to monitor arousal in the methods of the application, but subjective questionnaires will not be considered as reliable indicators of arousal. The present invention is based on measurements that are technical and scientifically verifiable and reproducible and not upon subjective questioning.

The term "equivalent temperature ($t_{eq}$)", as used in this application, refers to the uniform temperature of an imaginary enclosure with air velocity equal to zero in which a person will exchange the same dry heat, by radiation and convection, as in the actual environment (ISO 7730, 1993).

$$t_{eq} = 0.55 t_a + 0.45 t_r + \frac{0.24 - 0.75\sqrt{v_a}}{1 + I_{cl}}(36.5 - t_a) \qquad (3$$

with
$t_a$ the ambient air temperature (° C.)
$t_{mrt}$ the mean radiant temperature (° C.)
$V_a$ the air velocity (m.s−1)
$I_{cl}$ the clothing insulation index (1clo=0.155 m$^2$·° C.W−1).

Next to this equivalent temperature relating to the whole human body comfort sensation at once, the equivalent temperature is often calculated for different local body sites separately.

The term "subject", as used in this application, for purposes of treatment or prevention includes any human or vertebrate animal. The subject can be a domestic livestock species, a laboratory animal species, a zoo animal or a companion animal. In one embodiment, the subject is a mammal. In an alternative embodiment, the mammal is a human being.

A "non-active subject", as used in this application, is defined as one who is making an effort to actually fall asleep. An "active subject", for the purpose of present, is defined as a subject who is performing an activity, whereby the mentioned activity can be active (working, running, . . . ), or passive (sitting, reading, . . . ). The principal criterion is the intention to remain awake and perform, or to be 'active'. An active subject who experiences sleepiness will fight the inset of sleep and strives for remaining mentally alert. Not only are the processes of sleepiness in non-active subjects (attempted sleep) and sleepiness in active subjects (struggle against sleep) characterised by distinct circumstances (cognitive effort to sleep/stay awake, posture, lighting conditions, . . . ), their very nature is substantial different which is expressed through discrepancies in sleep propensity scoring methods (e.g. Sangal et al., 1992) and cognitive responses to arousal (e.g. De Valck et al., 2004). The present invention only applies to normal to excessive sleepiness in active subjects.

"Normal sleepiness", as used in this application, is defined as all forms of sleep not comprised by the process of attempted sleep, while "excessive sleepiness", as used in this application, is defined as the overwhelming and recurring need to sleep at times when a person really wants to be awake. It translates itself into having difficulty in maintaining wakefulness and an increased likelihood of falling asleep in inappropriate situations. Excessive sleepiness refers to a propensity to fall asleep, nod or doze easily in relaxed or sedentary situations, or a need to exert extra effort to avoid sleeping in these situations. In addition to just normal or mild sleepiness, the excessive sleepiness can cause related symptoms, including poor memory, reduced concentration or attention, and irritability. A person experiencing excessive sleepiness can suddenly fall into a sleep state with almost no warning whatsoever. Sleep attacks can occur at any time, even in mid-conversation, and many times a day.

This present invention provides methods of monitoring and/or controlling bioprocesses of an individual human or animal using a dynamic and adaptive data-based on-line modelling technique capable of integrating measured, real-time information on one or more bioprocess inputs and one or more bioprocess outputs and linking this model or its outputs to the status of the individual human or animal. With data-based, it is meant that a model is used with real time data to estimate the parameters in the model. According to a specific embodiment, the models are both data-based and mechanistic, meaning that physical or biological meaning can be attributed to the model parameters.

More particularly, methods are provided wherein at least one of the bioprocess inputs is a metabolism related variable of the human or animal and at least one of the bioprocess outputs is a an estimation of a component of an arousal variable relating to or containing an index of arousal of the human or animal based—at least in part—on the at least one metabolism related variable, thereby allowing monitoring in conditions involving changing metabolic energy demands of the individual. According to a further particular embodiment, methods are provided wherein at least one of the bioprocess inputs is a performance related variable of the human or animal and at least one of the bioprocess outputs is an estimation of an index of arousal of the human or animal based—at least in part—on the at least one performance related variable, thereby allowing monitoring in conditions involving performance of the individual.

According to a particular embodiment, the arousal variable of which a (physical) component is estimated by the model is also measured as an additional bioprocess input or output.

The methods according to this aspect of the invention are extremely well suited to monitor and control the value of indices of arousal, due to the properties of an on-line dynamic model that takes into account the time-varying characteristics of the monitored individual. More particularly, the methods according to this aspect are useful in the monitoring and controlling of bioprocesses involving performance of the individual human or animal, e.g. in the training of animals or athletes.

Furthermore, for the first time it is possible to monitor and control the arousal component influencing the performance of the individual in an accurate way: using physiological variables, in real time.

According to this aspect of the invention, the methods further involve a step of subtracting the estimated physical component (or total physical component) of the arousal variable from the measured arousal variable and using the difference to monitor and/or control the arousal component (i.e. the index of arousal) of the arousal variable.

This can be done due to the properties of the arousal variables. These variables are traditionally monitored to study the effect of arousal (e.g. variation in EEG frequency (increases with increasing arousal), variation in EEG voltage (decreases with increasing arousal), varying heart rate, change in skin conductance, . . . ) but are studied as the change between aroused and non-aroused state. I.e., for reasons of convenience, they are regarded as varying only with arousal. However, indices of arousal also vary due to other factors, such as normal physical activity. In fact, the hallmark of all these (physiological) variables is that they can be divided in at least two components: the total physical component (covering the component of the variable required for basal metabolism, the mechanical component resulting from physical activity, as well as possible other components directly related to physical events, such as the component for the heat balance) and a component related to arousal. Unless explicitly stated otherwise, "total physical" (as in e.g. total physical activity, total physical component) is meant to include mechanical components (e.g. mechanical activity of the individual, such as movement) as well as components required for basal metabolism and for the heat balance of the individual.

What is referred to as the "total physical component" of the variable relating to or containing an index of arousal thus is constituted of several other components, but these can be modelled—and thus quantified—using bioprocess input variables. For instance heart rate, a typical arousal variable, can be decomposed in heart rate required for mechanical activity, heart rate required for basal metabolism, heart rate required for heat balance and heart rate required for arousal. The three first components can all be grouped under the "total physical component" of the arousal variable (here heart rate), and these components can be modelled using input and output variables, be measured, or both. Only the last, "arousal" component (or 'physiological manifestation of arousal' component, 'physiological arousal' component in short) can not be modelled directly based on input variables.

This arousal component, which is thus not directly relating to physical activity or basal metabolism, may for instance be reflective of mental or emotional processes, stress, anxiety, excitement or the like. However, the physiological manifestations of these processes are physiologically detectable. Moreover, the component of an arousal variable that is attributable to actual arousal and not to aforementioned physical processes can be measured in real time by subtracting the real-time estimation of the (physical or total physical) component of the variable relating to or containing an index of arousal from the real-time measured variable relating to or containing an index of arousal.

Typical examples of arousal variables include, but are not limited to, measures of brain activity such as ERP (event related potentials), brain waves (e.g. monitored by electroencephalography, EEG), fMRI (functional magnetic resonance imaging), measures of skin conductance (such as skin conductance response, SCR; galvanic skin response, GSR; phasic electrodermal reaction), cardiovascular measures (such as heart rate, HR; beats per minute, BPM; heart rate variability, HRV; vasomotor activity), muscle activity (e.g. measured by electromyography, EMG; but muscle tension or movement may also be assessed by videographic means, using image analysis/processing (e.g. for assessing facial expression or total facial movement)), changes in pupil diameter with thought and emotion (pupillometrics) and eye movements (e.g. recorded via the electro-oculogram (EOG)), breathing patterns, respiration rate, blood pressure (e.g. systolic blood pressure, diastolic blood pressure, mean arterial blood pressure), vagal tone, blood, plasma, saliva or urinary protein or neuroactive substance concentration (e.g. adrenaline, noradrenalin, cortisol, serotonin, IgA, dopamine, acetylcholine, histamine, adenosine, glutamate, adrenocorticotropic hormone (ACTH), prolactin, glucocorticoids, or metabolites of any of these, . . . ), peripheral skin temperature, piloerection (e.g. tail piloerection), tail flagging activity, sound (e.g. variation in squeaks, or other sound produced by the living organism), postural profile (as e.g. measured by centre of pressure profile, centre of mass profile, or using image information/analysis), behaviour, displacement activities (e.g. self-directed behaviours such as self-touching, scratching, and self-grooming, scent marking such as foot rubbing, chest rubbing, urine washing, flank rubbing, and ano-genital marking), metabolic rate (e.g. measured by overall oxygen use), sympathovagal balance, sexual arousal variables (e.g. vaginal erythema, vaginal transudate volume, penile rigidity, thalamic activity), changes in blood chemistry, startle reflexes (e.g. in response to unexpected stimuli such as noise bursts), blushing, trembling, and early gene expression. Considering the definition of arousal as the ability to mobilize metabolic energy to meet environmental or internal demands on behaviour, all variables containing an index of arousal will also be metabolism related variables, and can thus, depending on how the modelled bioprocess is defined, be used as bioprocess input.

Thus, according to these embodiments of the invention, the methods can be performed as follows. One or more biological response variables or output variables (e.g. heart rate, brain activity, sound production, activity, posture, . . . ) of an individual human or animal are measured. These contain, possibly among others, a variable relating to or containing an index (or measure) for arousal (e.g. heart rate, brain activity, skin conductance . . . ). These measured output variables show how the body is responding to input variables.

One or more input variables (such as power, speed, heat losses, food intake, etc.) that can influence the output variable or response of the individual are measured. At least one of the input variables is a metabolism related variable (e.g. power production, training activity, body motions, . . . ).

Typical examples of bioprocess inputs and outputs include, but are not limited to, heart rate, training input, power production, EEG, ECG, food intake, weight gain, weight loss, skin conductance, movement, speed, travelled distance, light intensity, 3D position (e.g. of fish), temperature of environment, body temperature, behaviour variables, environmental sound, posture, body language, environmental stressors, heat production, medication or drug intake, concentration of proteins, hormones, peptides or (neuro) active substances in blood, plasma or saliva, biorhythm, training activity or performance, and so on. In principle, all variables that may influence the monitored bioprocess and can be quantified, measured or modelled in any way can be considered as bioprocess inputs. Specifically, metabolism related variables are envisaged as at least one bioprocess input.

Likewise, all variables that may be influenced by the monitored bioprocess and can be quantified, measured or modelled in any way can be considered as bioprocess outputs. Specifically, at least one arousal variable is envisaged as a bioprocess output.

Typical examples of metabolism related variables that can be used as bioprocess input include, but are not limited to power production (i.e. the power generated by muscle activity), training input or activity (e.g. the effort level or the amount of power that should be generated), body motions, body movements, speed (e.g. running speed, cycling speed), speed of movement or motions, and acceleration.

Examples of performance related variables that can be used as bioprocess input include, but are not limited to power production (i.e. the power generated by muscle activity), training input or activity (e.g. the effort level or the amount of power that should be generated), body motions, speed (e.g. running speed, cycling speed), speed of movement or motions, and acceleration, biorhythm, time of day, circadian rhythm inside living organism, behaviour, way of walking, etc.

When using a metabolism or performance related variable as model input, one may choose a variable that is as little influenced by arousal as possible. Variables that are clearly influenced by the arousal state of the individual human or animal (e.g. heart rate) can however also be used. This can for instance be done by breaking down the variable in an arousal component and an arousal-independent or physical component and only using the latter as model input.

Moreover, it should be realized that depending on how the model is defined and on which variable(s) are measured, model input and output can be switched, i.e. the model output will be an estimation of a metabolism related variable based on the bioprocess input that is an arousal variable. This is also envisaged within the scope of the invention as an equivalent to the described models, as it merely reverses the relation between input and output, but does not essentially change the way the methods are performed.

It should be realized that all actions of a human or animal can to a greater or lesser extent be influenced by the arousal of that individual human or animal. As will be explained further, the bioprocess input and output influence each other. When looking to the training of athletes for example (see FIG. 3A) it can be noticed that the resulting total performance of the training inputs is depending on a physical status and the arousal of the individual. The physical training input can influence the physical status and as usual a mental training input can influence the status of arousal. However the arousal of the individual will influence the physical activity during training as well. Indeed when the athlete is stressed, his or her behaviour, movement and training action will be different from when he or she is relaxed. This means that there is a feedback from the status of arousal to the physical inputs during training (see FIG. 3B). It is however also known that all physical performance needs metabolic energy and consequently needs a corresponding heart rate. Consequently a part of the total heart rate is corresponding to the physical action resulting from a feedback of arousal on training input. In technique according to the present invention this part of Heart Rate is part of the Physical component of heart rate since it is the result of a physical performance of the body. Beside this part there still will be a component of arousal in the total heart rate. Thus, the fact that bioprocess inputs also may be influenced by arousal does not mean that the bioprocess outputs do not possess an arousal component anymore.

By modelling the physical component continuously in an on-line way as a response to physical training input and this for varying status of arousal makes that at every moment there is model available to predict how the Physical status will respond to the training input. By using this model an on-line model and a so called model predictive control can be made to optimize for this individual the training for improvement of the physical status (See FIG. 3B).

By modelling the estimated arousal continuously in an on-line way as a response to mental training and this for varying physical status makes that at every moment there is a model available to predict how the arousal will respond to the mental training input. By using this model an on-line monitor and a model predictive control can be made to optimize the efficiency of the mental training for this individual athlete on a given moment. Possible examples of mental training input variables are e.g. biofeedback exercises, controlling breathing pattern, synchronizing breathing rhythm and heart rate variability (cardiac rhythm), synchronizing breathing rhythm and concentration level (EEG), concentration exercises, reaction time performance (e.g. Psychomotor Vigilance Test or PVT test), Stroop-test, visual search exercises, etc.

Thus, according to another particular embodiment, the metabolism related variable used as model input may be influenced by the feedback of the arousal state of the individual.

The model output is the expected process output as a relation to the process input, described by the model. As the model output only describes the signal in the process output that is directly related to the process input, the value or dynamics of the model output typically will not fully match those of the process output. In processes where arousal plays a role, this difference can be attributed to arousal. All the more so if the other components are accounted for by the model, either as model input (e.g. mechanical activity) or environmental variable. Thus, the difference in the prediction between bioprocess output and model output can then be attributed to an unknown variable (linked to the arousal of the monitored individual), which can be quantified and/or described by solving a set of equations with the known variables For instance, the measured heart rate will be higher than the one predicted based on model inputs as physical performance, basal metabolism and heat balance if the monitored individual is aroused. This difference can be attributed to the 'arousal' component of heart rate, which can be quantified (e.g. by subtracting the known heart rate components (due to basal metabolism, heat balance and mechanical activity) from the measured total heart rate).

In a similar manner, the dynamics of the difference (or unknown variable) can be assessed. This involves monitoring the arousal variable (or monitoring the unknown variable that is a component of the arousal variable) over time. These dynamics of the arousal variable or of the unknown variable can then be checked for the presence of arousal events. As will be demonstrated in the Examples section, dynamics of the arousal component (i.e. the unknown variable) contain information on the presence of arousal events (or 'emotional events', as described by Myrtek et al. (Myrtek et al., 1999). According to one particular embodiment, the methods of the invention further comprise the step of classifying the arousal component (unknown variable) as containing or not containing arousal events, depending on the dynamics of the arousal component.

Moreover, dynamics of indices of arousal are known to be correlated with the quality of arousal, i.e. whether the arousal can be attributed to positive (e.g. excitement, euphoria) or negative events (e.g. induction of fear, rising anger, anxiety) (Brosschot and Thayer, 2003; Anderson et al., 2005). With the methods currently provided, it is possible to monitor the dynamics of the indices of arousal as such and correlate this to the quality of arousal. However, it is particularly envisaged to study the dynamics of the arousal component alone instead of monitoring the total arousal variable (e.g. arousal heart rate versus total heart rate). By making this possible, the methods according to this embodiment allow a more accurate monitoring, as changes in physical activity, heat balance or basal metabolism can be accounted for. The observed dynamics are thus truly attributable to arousal and not e.g. due to changed physical activity, as can not be ruled out when monitoring e.g. total heart rate. Thus, according to a specific embodiment, the arousal events contained in the arousal variable are further classified as contributing to positive, neutral or negative arousal depending on the dynamics of the unknown variable.

An on-line real-time model is calculated to quantify and predict the part of the total measured output variable(s) that is a response to the measured input(s). To this end, a continuous feedback of both process input and process output (FIG. 1, FIG. 4) is used and this offers an advantage to the use of only an output. According to a particular aspect, the minimal mathematical complexity to describe the whole system is identified since in that case the number of parameters to be estimated on-line is smaller. Since the responses of people are not only individually different but also time-variant, and since these responses are too complex to be modelled based on merely the classical physiological rules, specific mathematical modelling techniques are used here to identify suchlike complex processes (Young and Jakeman, 1979; Ljung, 1987).

So-called black box models can successfully be applied to model complex processes. According to one embodiment, the mathematical modelling technique that is used is a black box model.

According to another embodiment, the mathematical modelling technique that is used is a data-based model.

Another technique that may be used for modelling Complex Individual Time-varying and Dynamic (CITD) systems is the technique of Data-Based Mechanistic Modelling (DBM, Berckmans, 1992; Young and Wallis, 1993). This technique is very suitable, as it offers the advantage that it is easy to go from one application of the model to another while applying the same model since the model parameters have a physical or biological meaning. Using DBM, it will take less time to find an appropriate model that accurately describes the current application than with other modelling techniques. According to a particular embodiment, the methods use DBM as the underlying mathematical model.

Recent research has demonstrated that this "systems biology" approach delivers new insights in the functioning of complex biological systems (Pennisi, 2003). Through such more simple mathematical models (e.g. black box, DBM), it is possible to estimate (even on-line) parameters of mathematical model structures in gliding windows with a limited number of historical measurement data (FIG. 5). At every moment, the future process response is predicted based on this small amount of measurements from the recent past. The identified models are so compact that this method becomes applicable to every individual subject, and that—through the recent revolution in hardware—the possibility arises to implement these models in real-time.

Such models between the selected input and output variables are completely characterized by their model structure (the mathematical equations, number of model parameters, time delays, numeric value model parameters, etc). Since subjects are individually different, their model characteristics will be different. The model characteristic per individual will also vary over time since the condition of the subject is changing over time. In practice changes in number of model parameters, model parameters values and/or time-delays will indicate changes in physiological or biological mechanisms and hence they become a quantitative measure for a change in mental/physical condition. By continuous modelling the dynamic changes in the biological process and by adapting the mathematical model, these changes are objectively quantified.

By attributing biological meaning to the mathematical model parameters based on existing knowledge regarding the studied system, new and fundamental insights are obtained regarding the physiological process and its interaction with the environment. Recently, a specific procedure for deriving biological meaning from the model structure (Boonen, 2005) and model parameters (Quanten, 2005) was derived.

By quantifying and predicting the part of the total measured output variable(s) that is a response to the measured input(s), the dynamic part of the measured output variable that is a response of the body to the measured input variable is quantified. For instance, the component of an arousal variable due to mechanical activity can be calculated based on the input of the metabolism (or performance) related variable. Based on a limited amount of information from the recent past (history) of both input and output variable, the value of the output variable can be predicted for a certain amount of time steps in the future (prediction horizon). The relation between history, prediction horizon and accuracy of prediction need to be analyzed for each application in order to determine the most appropriate settings of both history and prediction horizon.

The principle of the moving rectangular window approach is illustrated in FIG. 6A for an overlapping interval of one sampling interval and a window size S. On every discrete time instant k, the parameters θ1k and θ2k are estimated based on information of cumulative feed intake and weight measured during a time window of S samples. In the experiments the time period between two subsequent observations lasted 24 hours.

On each time instant k (day) the parameters of equation [1] were estimated based on the measured values of weight and cumulative feed intake in a time window of S days (from Days k−S+1 until k) and subsequently the weight was predicted F steps ahead (day k+F) by using equation [1] with CFk+F. On day k+1 the procedure was repeated. So, based on the measured information in a time window ranging from k−S+2 until k+1, the model parameters (θ1k+1, θ2k+1) were estimated and weight was predicted F days ahead (day k+1+F) by applying the input CFk+1+F to the estimated model. In this way the weight was predicted at each time instant on the basis of a small window of actual and past data.

In order to investigate the accuracy of the model predictions as a function of window size S and prediction horizon F, the recursive estimation algorithm was applied to each data set with a window size ranging from three to seven days and a prediction horizon ranging from one to seven days. As a result, for each data set 35 (5×7) combinations of window size and prediction horizon were used to model the growth response.

The quality of fit of the modelling techniques can be quantified by means of the Mean Relative Prediction Error (MRPE) which can be defined as:

$$MRPE = \frac{1}{N}\sum_{k=1}^{N}\sqrt{\left(\frac{w_k - \hat{w}_k}{w_k}\right)^2} \cdot 100 \qquad [6]$$

where MRPE is the mean relative prediction error (%); N is the number of samples; wk is the weight measured with the automatic weighing systems at time k (kg); $\hat{w}_k$ is the predicted weight at time k (kg). Similar measures for quantifying the goodness of fit of growth models were used by Oltjen and Owens (1987) and Talpaz et al. (1991).

In FIG. 6B the recursive modelling technique was used to model the growth response of broilers for 35 combinations of window size and prediction horizon. For each combination, the relative prediction error (MRPE) was calculated using equation [6]. In FIG. 6B, a typical example of MRPE as a function of window size and prediction horizon is shown. As can be seen in FIG. 6B, the MRPE shows a minimum as a function of window size S and increases as a function of prediction horizon F.

This shows that depending on the considered bioprocess and the measured variables and their dynamics, an optimal size of the window size S with history of data and the size of the prediction horizon F with predictions for the future can be selected.

The course of the MRPE as function of the window size could be explained by the combination of two aspects. First, the uncertainty on the parameter estimation will decrease with increasing number of data used to estimate the model parameters. Second, as window size increased, it could be expected that the assumption of linearity between cumulative feed intake and animal weight became less acceptable, resulting in parameter estimates which were no accurate description of the true (nonlinear) relation.

In conclusion, the course of MRPE as a function of window size could be regarded as a trade off between the two higher mentioned aspects, namely on one hand increasing window size resulted in a decrease of the standard errors on the parameter estimates but on the other hand caused more bias on the parameter estimates due to the assumption of linearity.

The mean relative prediction error as a function of window size, reached for both experiments a minimum on average at a window size of five days. Therefore, in the analysis of the MRPE as a function of prediction horizon, the size of the rectangular window was set to 5 days.

Other parts of body responses variables for this individual (such as basic metabolism, heat losses, . . . ) may be added to this real time modelled response of the body to the input variable(s). This way, a total response of the body to these input variables for this individual on that moment is obtained. This total response of the body is the estimated component of the arousal variable (which thus at least consists of the calculated mechanical component of the variable containing an index of arousal), and corresponds to the above-described "physical component" of the arousal variable. According to a particular embodiment, the estimated component of the arousal variable will be composed of at least the calculated mechanical component of the arousal variable and the component due to basal metabolism. According to a further particular embodiment, the estimated component of the arousal variable is composed of at least the calculated mechanical component of the variable containing an index of arousal, the component due to basal metabolism and a component due to heat balance.

Although the performance related variable will be measured in real time to allow an accurate prediction of the mechanical activity component, not all input variables need to be measured continuously, or not even at the same time. It is possible that some of these "other parts of body responses" may not vary during the monitored process (e.g. the heart rate related to basal metabolism can be measured in the morning and remain constant during the day). Other variables may be expected to change (e.g. heat losses), in which case these may have to be measured continuously to incorporate them in the real-time estimation of the arousal variable. Continuously in this case has to be interpreted in relations to the dynamics of the considered process. The sample frequency can for example vary from very high (e.g. 40.000 samples per second) for sound signals to very low (e.g. 1 sample every week). The required sample frequency is depending on the dynamics of the monitored inputs, outputs and/or bioresponses or the dynamics of the non-measured but influencing disturbing variables.

Moreover, by making the model in real time, the influences of all other variables that are not measured are taken into account in the body response to the measured inputs. In practice, this means that variables that are not or can not be measured are treated as if they were external disturbances. The effects of these and other external disturbances will cause that the model prediction is not fitting with the new measured values and consequently this is a signal to redefine (this means to re-estimate the model parameters or the model structure) the relation between bioprocess inputs and bioprocess outputs. External disturbances can be any variable that has an effect on the considered bioprocess but is not measured for input into the model. External disturbances may both be disturbing variables and other (non-disturbing) environmental variables. Typical external disturbances include, but are not limited to illness, food intake, weather conditions, type of clothing (e.g. shoes), medication, drug use, stress, . . . (see FIG. 7C). Typically, external disturbances will be mostly disturbing variables (e.g. weather conditions), as environmental variables that can be adapted in a controllable manner (i.e. those environmental variables that are not disturbing variables) may be measured to be able to control the bioprocess output via such environmental variable. But, as mentioned, if environmental variables such as e.g. heat loss are not measured, they will still be taken into account as part of the external disturbances.

The relation between Heart Rate and Activity is always influenced by arousal or mental component since it is impossible to measure Heart Rate without the possible influence of arousal. When the individual is stressed than there will be a feedback of this stress to the way his/her activity is performed. However all activity performed by the body needs a Heart Rate to pump the blood and realise the corresponding metabolic energy. Even when part of the activity is due to arousal, than the $HR_{total}$ can be decomposed in this $HR_{mechanical}$ and the $HR_{arousal}$. Since performance is strongly influenced by arousal, the measured input variable will be influenced by arousal. (See FIG. 3B).

By subtracting the estimated component of the arousal variable (i.e. the predicted total response of the body to the measured input variables) from the total measured output variable (arousal variable) we get the actual arousal component of the arousal variable, for this individual on that given moment and place. For instance, the heart rate component that is due to arousal is the measured total heart rate minus the estimated (physical component of the) heart rate. Likewise, the skin conductance due to arousal is the measured skin conductance minus the estimated skin conductance.

Not only can the arousal component thus be quantified and monitored, it is also possible to qualify or score the arousal as positive, neutral or negative. Indeed, the dynamics of indices of arousal differ depending on whether the arousal is due to positive events (e.g. in the case of excitement) or due to negative events (e.g. in the case of anxiety, fear, anger or aggression). See for instance Brosschot and Thayer (Brosschot and Thayer, 2003) for the dynamics of heart rate after negative or positive emotions, Anderson et al. (Anderson et al., 2005) for recovery data of cardiovascular measures (e.g. blood pressure) in anger provocation research, or Burbridge et al. (Burbridge et al., 2005) for differences in heart rate and skin conductance responses when discussing affectively negative as compared to positive or neutral topics.

Using the methods according to these aspects of the invention, it is also possible to monitor the physical component of the variable relating to or containing an index of arousal, either separately or in addition to the monitoring of the arousal component.

According to a particular aspect, the provided methods can be used to control the arousal component of the arousal variable, the physical component of the arousal variable, or both. According to a specific embodiment, both the arousal and the physical component of the variable relating to or containing an index of arousal are controlled using the methods according to the embodiment. Control of the arousal variable generally implies that the arousal variable (or one or more of its components) is directed towards a desired reference value, or along a desired (reference) trajectory. As the physical component of the arousal variable is a bioprocess output, such control can be achieved by adapting one or more bioprocess inputs. For instance, to control the physical component of heart rate along a desired trajectory, the training input can be changed or varied.

Moreover, when using a data-based mechanistic model, the model parameters can be linked to physical and arousal features. It is a surprising finding that the dynamics of the model parameters modelling the physical status of the individual can be used to detect whether the individual has taken or been administered doping. Indeed, if the timescale for updating the model parameters modelling the physical status of the individual becomes significantly smaller, this is indicative of an unnatural change in the body of the individual, as the body normally only gradually adapts itself to new circumstances (hence the slower timescale of change for physical relative to arousal model parameters). Such a sudden change of how the body reacts can however be achieved using performance-enhancing drugs or doping.

Changing the arousal component can also be achieved. Typically, this is done using biofeedback. Biofeedback is a technique in which individuals are trained to adjust bioprocesses of their body by using signals from their own body. It is often used in therapy: physical therapists e.g. use biofeedback to help stroke victims regain movement in paralyzed muscles, psychologists use it to help tense and anxious clients learn to relax, specialists in many different fields use biofeedback to help their patients cope with pain. Moreover, biofeedback is also used to improve performance under arousing conditions, e.g. in the case of pilots (Cowings et al., 2001).

Biofeedback may be implemented using biofeedback machines. These machines can detect a person's internal bodily functions with far greater sensitivity and precision than a person can alone. (In fact, up to a certain extent, such machines can be compared to polygraphs, which also detect changes in physiological processes such as heartbeat, blood pressure, respiration and electrical resistance (galvanic skin response or GSR).) This information may be valuable, it can be used to gauge and direct the progress of treatment, e.g. by the individual itself, or under supervision of a trainer. One commonly used type of machine, for example, picks up electrical signals in the muscles. It translates these signals into a form that individuals can detect: it triggers a flashing light bulb, perhaps, or activates a beeper every time muscles grow tenser. If individuals want to relax tense muscles, they try to slow down the flashing or beeping. This can be applied to humans or animals. Of course, it may be that the signals will need to be adapted depending on the kind of animal that is monitored, but biofeedback for non-human animals is certainly also feasible and has e.g. been extensively demonstrated in rats.

Typical examples of biofeedback using devices include, amongst others, an electromyogram (EMG), peripheral skin temperature, galvanic skin response training and electroencephalography (EEG). An EMG uses electrodes or other types of sensors to measure muscle tension. By the EMG alerting to muscle tension, it is possible for an individual to learn to recognize the feeling early on and try to control the tension right away. EMG is mainly used as a relaxation technique to help ease tension in those muscles involved in backaches, headaches, neck pain and teeth grinding (bruxism).

Peripheral skin temperature can be measured by sensors attached to fingers or feet. Because body temperature often drops when an individual experiences stress, a low reading can prompt the individual to begin relaxation techniques. Temperature biofeedback can help treat certain circulatory disorders, such as Raynaud's disease, or reduce the frequency of migraines. The physiological process behind the temperature drop associated with the stress response is quite simply vasoconstriction (blood vessels narrowed by the smooth musculature in their walls).

With galvanic skin response training, sensors measure the activity of sweat glands and the amount of perspiration on the skin, thereby alerting to anxiety. This information can be useful in treating emotional disorders such as phobias, anxiety and stuttering. This is the method most commonly used by polygraphs (lie detector machines). Galvanic Skin Response meters are also now gaining popularity in hypnotherapy and psychotherapy practice where subtle physiological changes indicating arousal can be more easily detected than by observation alone.

An EEG monitors the activity of brain waves linked to different mental states, such as wakefulness, relaxation, calmness, light sleep and deep sleep. EEG voltage is inversely correlated with behavioural arousal, while EEG frequency varies directly with arousal. Interestingly, EEG characteristics of REM sleep are nearly identical to those of the alert state, reflecting episodes of dreaming.

Arousal is a property of the organism that is found throughout the animal kingdom, including those species with very rudimentary nervous systems (e.g. jellyfish, insects, mollusks, . . . ). Although usually termed sensitization in these organisms, it is associated with global changes in metabolism and is likely the precursor to the arousal response in higher organisms. The anatomy and physiology of arousal are similar among primitive vertebrates and highly complex mammals. There is abundant literature available on (physiological) arousal of species as diverse as squirrels, dogs, chickens, quails, horses and of course, humans. According to a particular embodiment, methods according to the embodiment are used to monitor a vertebrate animal. According to a further particular embodiment, a mammal or an avian is monitored. According to yet a further particular embodiment, the methods of the embodiment are used to monitor an individual horse or an individual human.

According to a particular embodiment, more than one model can be applied to monitor a bioprocess in an individual human or animal. Typically this is done by using a first CITD model that determines a value for an unknown variable from a set of equations, as described in this application, and then using the value of the unknown variable as a model input in an additional model or algorithm. According to a specific embodiment, this further model has a similar model structure to the CITD model (i.e. it is also a model generated on-line, inputting the real-time information on bioprocesses of the animal, generating bioprocess outputs using a dynamic and adaptive on-line modelling technique, and at least one of the model outputs is an estimation of a bioresponse of the human or animal based on the unknown variable that is used as (one of the) input(s)). According to another particular embodiment, the model structure of the second model or algorithm is of a different nature.

According to a further particular embodiment, not one, but two CITD models are used, each generating a different unknown variable (related to bioprocesses that have a different time scale), and both variables are used as input in the additional model.

The use of two models to determine the arousal component of two separate output variables containing an index of arousal as response to a metabolic related input variable, allows to study different bioprocesses or bioresponses wherein arousal (or changes in arousal) can be detected on different time scales (e.g. fast acute and slower response)). According to one particular embodiment, such combination of models, wherein in the first model an unknown variable attributed to arousal is singled out in a fast acute loop and a wherein in a second model an unknown variable attributed to arousal is singled out in a slower loop, is used to monitor normal to excessive sleepiness in an active subject (NE-SAS). This can be done by using the different unknown variables as input in an additional model that predicts or monitors NESAS.

NESAS may be dangerous for people who have to operate equipment such as transportation systems (cars, trucks, busses, planes, . . . ), monitoring devices or other machinery where responsibility and/or required alertness level is high. Since years, NESAS has been recognized as a major contributor to safety accidents in traffic as well as in the working environment worldwide. Considering traffic safety, up to 24% of all road crashes, especially in professional truck driving, can be traced back to driver sleepiness (which is in fact the most well-know form of NESAS). Also, people involved in professions with lots of responsibility over other people's lives or expensive machinery are extremely sensitive to this (excessive) sleepiness hazard. Possible reasons for NESAS on the job are abundant: sleep deficit, time of day (circadian rhythm), sleep disorders, medication, or shift work. For instance the Sleep Apnea Syndrome is a sleep disorder that can cause NESAS, and can result in falling asleep during driving. Although lots of efforts have been made throughout the years to develop an accurate and reliable sleepiness detection system, no working system is yet implemented in vehicle cabins or in the working environment. There is thus a need for a system that is reliable enough to guarantee unambiguous detection of NESAS. The major drawback that any sleepiness detection system needs to surmount is the Complex, Individual different, Time-varying and Dynamic (CITD) nature of the process of NESAS. Existing systems are either not realizable from a practical point of view; or suffer from an unreliable prediction; or are based on image analysis techniques which are not accounting for the CITD nature of NESAS; or are based upon late detection of performance decrements instead of early detection of a potentially dangerous drowsy state of the worker or driver.

According to a further specific embodiment, other variables are used as input of the second model, in addition to the index of arousal (i.e. the unknown variable) generated with the (one or two) CITD model(s). Examples of such additional variables that may be used as input include peripheral heat loss, biorhythm, driving performance, but other variables (e.g. metabolism related variables) may be used as well.

It should be appreciated that the models and methods described here have a very broad applicability; indeed, virtually any bioprocess can be monitored using the methods of the invention. In particular, processes wherein (cognitive or physical) performance is involved are envisaged. Although the monitored processes can be very diverse, the underlying models and methods all have the same principle. Exemplary applications of bioprocesses wherein the provided methods may be used for monitor and/or control purposes include, but are not limited to: physical and arousal monitoring and control in football and all other sports (cycling, Formula 1, handball, basketball, volleyball, archery, . . . ), driver monitoring, stress monitoring (e.g. in work-related situations), alertness in professional situations (e.g. for air traffic control), military applications (monitoring and controlling stress and aggression), monitoring adversaries in sports, monitoring the attention level or learning capabilities of students, improving learning difficulties, animal welfare, and birth prediction for humans and animals.

The methods according to particular embodiments can be partly or wholly automated. For instance, the automated part may be the real-time model which provides a status of the individual human or animal as output that can be linked to the need for action relating to (a) bioprocess input(s). The individual or trainer (or the like) can then undertake or start the necessary action or operation based upon this information. Alternatively, the whole method is automated and the model decides when an operation has to be modulated. For instance, the model may directly modulate the resistance of a home trainer, thereby modulating training input. This automation increases the user-friendliness of the provided methods. The concepts of computation system and computation modules will be discussed here.

The methods according to specific embodiments can be implemented in a computation system or computational system, which are used as synonymous here. A configuration of a computation system can consist of at least one programmable processor coupled to a memory subsystem that at least comprises of one form of memory, such as for example, RAM, ROM etc. The processor can be for general purposes or can serve a specific goal. The processor (or microprocessor) can also be used for inclusion in a device, for example a chip (or microchip) which has other components which fulfil other functions. As such one or more aspects of the invention can be implemented in digital electronic circuits, or in computer hardware, firmware, software, or combinations of those. Typical examples of such hardware include, but are not limited to, a personal computer, a PDA, a smart phone, or a GPS. According to a particular embodiment, the computation system can be wearable on or in the body of the individual human or animal to be monitored, with possible (wireless) connections to other parts.

The computation system can contain a storage subsystem that contains at least one disk drive and/or CD-ROM station and/or DVD station. In some implementations a display system, a keyboard and/or a pointer device can be included as part of a user interface subsystem to allow a user to input information manually. Ports for the input and output of data can also be included. Other elements which can be contained with particular embodiments are network connections; connections to several devices etc. . . . . The different elements of the computation system can be linked through several means, such as for example, via a bus subsystem that contains at least one bus. The memory of the memory subsystem can at a certain moment contain a part of the, or the entire set of instruction needed to perform the steps of the methods described herein, when executed on the computation system. Hence, although a computation system is known, a system that contains the instructions to implement aspects of the methods herein described (such as simulating one or more arousal variables, or the control of different components of an arousal variable based on the measured arousal variable and simulated component thereof) is not yet described in the state of the technical art.

Specific embodiments also include a computer program product, which contains at least one computation module or computational module, which are used as synonyms here. Different computation modules (or "algorithms") can be integrated or operate individually. The computer program product provides the functionality of the methods described in this disclosure when they are performed on a computer or comparable computation system. Such a computer program product can be stored physically on a carrier which contains machine readable code for execution by a programmable processor. Particular embodiments also relate to a carrier which contains a computer program product which, when executed on a computer or comparable computation system, provides instructions for the execution of any method described herein. The term "carrier" refers to each medium which can pass on instructions to a processor for execution. Such medium can adopt various forms such as, but not limited to, non-volatile media and transmission media. Non-volatile media include for example optic or magnetic disks, such as a storage device which is part of a mass-storage medium. Frequently used forms of computer readable media include a CD-ROM, a DVD, a flexible disk or floppy disk, a tape, a memory chip or cartridge or every other medium from which a computer can read. Different forms of computer readable media can be used for the transfer of one or more sequences of one or more instructions to a processor for execution. The computer program product can also be transmitted through a carrier wave in a network, such as a LAN, WAN or the internet. Transmission media can be in the form of acoustic or optical waves, such as, these generated during radio wave and infrared data communications. Transmission media include coaxial cable, copper wire and fibre optics including the wires which form a bus within a computer.

Further, the invention relates to systems which can be used for implementing the methods according to specific embodiments. According to one embodiment, this system for monitoring the status of an individual human or animal includes the following: means for collecting and storing real-time information on bioprocess inputs and outputs, wherein at least one of the bioprocess inputs is a metabolism related variable of the animal, and wherein a measured arousal variable of the individual human or animal is another bioprocess input or output, and means for on-line modelling and generating an estimation of a component of the arousal variable of the human or animal based on the at least one metabolism related variable.

The means for collecting and/or storing real-time information on bioprocess inputs and outputs will typically be sensors capable of real-time monitoring. Such sensors are well known in the art and include, but are not limited to: heart rate monitors, accelerometers, GPS systems, motion sensors, cameras, electrodes, thermocouples, thermometers, apparatus to measure ECG, EEG, EMG, conductivity sensors, effort level measuring devices, decibel meters, ergometers, and the like. These sensors can be used as such, or may be integrated in another device or product, for instance in intelligent gloves or textiles. Since the bioprocess input and the bioprocess output are different variables, typically the means for measuring the bioprocess input will differ from the means for measuring the bioprocess output. According to a particular embodiment, the means for measuring the bioprocess input differ from the means for measuring the bioprocess output. According to another specific embodiment, however, a bioprocess input and bioprocess output can be measured with the same device.

According to a specific embodiment, the means for collecting the real-time information on bioprocess inputs and outputs are foreseen with means to send this real-time information to a computation system. The information can be transmitted via computer readable media, but also through a carrier wave in a network, such as a LAN, WAN or the internet. Transmission media can be wireless, e.g. in the form of acoustic or optical waves, such as, these generated during radio wave and infrared data communications. Transmission media further may include coaxial cable, copper wire and fibre optics including the wires which form a bus within a computer. According to a further specific embodiment, the means for collecting and storing real-time information on bioprocess are not contained in one physical entity, e.g. the sensor for collecting data can be placed on or near the human or animal that is monitored, while the storing of the data can happen on a computational system in another location (to which the real-time data are transmitted, possibly in a wireless way).

According to a particular embodiment, the means for on-line modelling and generating an estimation of a component of the arousal variable of the human or animal based on the at least one metabolism related variable include at least one computational module. Such computational module is described above.

According to a further embodiment, the system also includes means for on-line modelling and generating the difference between the estimated component of the arousal variable from the measured index of arousal. According to a particular embodiment, these means are provided in the form of a computational module. According to yet a further particular embodiment, the computational module is integrated with the computational module for on-line modelling and generating an estimation of a component of the arousal variable of the human or animal based on the at least one metabolism related variable.

In yet another embodiment, the system further comprises means allowing the control of a bioprocess input. According to this particular embodiment, the system includes means for comparing and determining the variance between the estimated component of the arousal variable and a preset reference arousal variable; means for comparing and determining the variance between the difference between the estimated component of the arousal variable and the measured arousal variable and a preset reference arousal variable component; and means for determining how one or more bioprocess inputs should be adjusted in relationship to the variance determined with one or both of the variance-determining means.

Typically, these three additional means will also be provided in the form of a computational module. According to one embodiment, these means are separate computational modules. According to another embodiment, these three means are integrated into one computational module. According to yet another embodiment, the means for determining the variance and/or the means for determining the adjustment are integrated with the means for on-line modelling an estimation of the component of the arousal variable and/or the means for on-line modelling the difference between the estimated component of the arousal variable from the measured arousal variable.

According to one aspect, systems according to the above-described embodiments are used for monitoring the status of an individual human, wherein the metabolism related variable is selected from the group consisting of training activity, body movement or body part movement, and power production; and the arousal variable is heart rate or muscle activity.

According to a specific embodiment, a system is provided that further comprises means for on-line modelling and predicting a bioresponse based on the input of at least the value of the unknown variable. Typically, this means is provided in the form of a computational module. According to a particular embodiment, this means or computational module is integrated with one or more of the other means or computational modules provided in the system. According to another embodiment, the means are provided separately.

Many bioresponses can be monitored using systems according to this embodiment. One of the particular bioresponses that is envisaged to monitor using systems according to this embodiment is NESAS.

According to a particular embodiment, the system further comprises means to output the modelled value. The means to output the modelled value is any means suitable for output. This can be a display device, but may also be e.g. a transmitting means. The output of the modelled value can be direct or indirect, i.e. it can be used directly (e.g. displayed as such), or it can be further processed or linked before it is generated as output. This output may or may not be directly used by systems according to different embodiments, e.g. by switching on or off additional devices.

According to another particular embodiment, the systems described in this application may further comprise alarm or signalling means. Typically, these alarm or signalling means will produce an alarm or signal when a monitored bioprocess input or output or a predicted model output exceeds a certain threshold. For instance, an alarm may be started when the measured value of the bioprocess output is significantly different from the estimated value of the bioprocess output (e.g. an arousal variable). Or a signal may be given to alter the training activity (as example of a bioprocess input) of an individual human or animal in order to follow a reference heart rate trajectory (as an example of a desired bioprocess output). Typically, the alarm or signalling means will make use of visual or sound signals, although other possibilities are also envisaged (e.g. radio waves). According to a particular embodiment, the alarm or signalling means is a part of the output means. According to another particular embodiment, the alarm or signalling means is operated by the output means.

According to another particular embodiment, the systems described in this application may further comprise controlling means. These controlling means are used to effectively control the individual human or animal, using the outputted information of the bioprocess. For instance, controlling means may alter the resistance of a home trainer or the speed or slope of an automated running device to control training activity, or may supply food or medication.

It is to be understood that the features of the methods and systems of the invention are not mutually exclusive and can be combined with each other. Further, the methods of the invention can be combined with the systems of the invention. According to a specific embodiment, the use of a computational module to model the value of one or more indices of arousal over time, based on a dynamic and adaptive data-based on-line modelling technique, wherein at least one of the bioprocess inputs is a metabolism related variable of a human or animal and at least one of the bioprocess outputs is an estimation of a component of the arousal variable of the human or animal based on the at least one metabolism related variable, in a computation system equipped with measuring means is envisaged.

To further illustrate the invention, the following Examples are provided. These serve illustrative purposes only, and shall not be considered as limiting the invention.

EXAMPLES

Example 1: Decomposition of Heart Rate

The total performance of a sports athlete will always be function of both his physical and mental status, and moreover, his physical performance is influenced by his mental status and vice versa (FIG. 3A).

In order to monitor and manage both the physical and mental performance (FIG. 3B) both the training effort (input signal) and resulting training effect on the body (output signal) are measured in real-time. In this way the Complex, Individual, Time-variant and Dynamic behaviour (CITD) of the individual can be handled. In the case of a sports athlete, this means that the individual athlete will be equipped with the necessary sensor technology to measure in real-time and telemetric the input and output signals to a data acquisition unit (FIG. 7A).

As output signal, the total heart rate is used. Total heart rate, because the heart rate signal measured by any means (from a simple heart rate monitor to a high technologic ECG measurement) always is and will be the total heart rate. This means that any measured heart rate signal contains components for the functioning of the basal body function, components of physical nature and a component due to (physiological) arousal (equation 1):

$$HR_{tot} = HR_{bmr} + HR_{mech} + HR_{heat} + HR_{PhAr} \quad (1a)$$
$$= HR_{phys} + HR_{PhAr} \quad (1b)$$

$HR_{tot}$ = total heart rate
$HR_{bmr}$ = Basal Metabolic Rate heart rate
$HR_{mech}$ = heart rate for mechanical activity
$HR_{heat}$ = heart rate for maintaining heat balance
$HR_{PhAr}$ = heart rate due to
(physiological manifestation of) arousal
$HR_{phys} = HR_{mech} + HR_{bmr} + HR_{heat}$ This means that in order to be able to reliable quantify the (physiological manifestation of) arousal component of heart rate, the total heart rate signal need to be decomposed into its physical and arousal component because total heart rate is a continuous and unquantified interplay of influences of both physical and arousal nature.

The fact that both the physical and the (physiological) arousal component of the total heart rate vary both intra- and interindividually is one of the reasons why any existing technique for quantification of the arousal component from total heart rate like will never be reliable enough. For instance the technique of Heart Rate Variability (HRV analysis or spectral analysis of the heart rate signal), extensively described in scientific literature for studying physiological arousal, is not yet proven reliable outside the laboratory environment when the individual in not restricted to constant and low levels of physical activity. It will not function correctly in every day life, e.g. during sport performances. HRV analysis and techniques, which may be reliable for subjects performing a constant mechanical activity cannot however be extrapolated directly to a realistic setting with variation in mechanical activity. This is because every form of and change in mechanical activity results in a different total heart rate. This means that the specific HRV spectral band of mental/arousal nature is diluted by 'noise' caused by the changing mechanical activity; and hence does not longer indicate solely the arousal aspect.

To solve this problem, the physical and arousal component of the measured total heart rate are to be separated (FIG. 7B). The basic idea behind the on-line separation of the physical and mental component of heart rate is the dominant relation between the physical activity of an individual and the physical component of his/her heart rate. When performing a physical training effort (e.g. 30 m sprint), the total measured heart rate will increase due to an increase in the physical component of heart rate, irrespective of possible additional arousal factors influencing total heart rate. This increase in the physical component of heart rate is a response to the measurable training activity (30 m sprint), and the reason here for is that the body needs to deliver extra metabolic energy to perform the requested physical activity. The physical component of the total heart is the means to deliver the needed extra metabolic energy to the muscles. Irrespective of the magnitude of the mental component of the heart rate there will always be a clear and direct relation between the performed physical activity and the physical heart rate component.

The presented technique for decomposition of total heart rate into a physical and arousal component contains the following, without being restricted to the hereafter summarized specifications. Both the input (training activity) and the output variable (heart rate) of the system (individual sportsmen), are measured in an on-line and continuous way as shown in FIG. 7C. However, an additional difficulty is imbedded in the individual and time-varying character of this relation between physical activity and the physical heart rate component. This relation does not only change between individuals, but also varies over time within the same individual (under the influence of e.g. sickness, food, weather conditions, type of shoes, medication, drug use, etc), as shown in FIG. 7C.

In order to obtain a reliable model, in addition to measuring in an on-line and continuous way both the input and the output variable, also the relation between input and output is identified and re-identified continuously and on-line. The relation between training activity (input) and heart rate (output) is identified and quantified by means of a compact mathematical relation (transfer function model) suited for on-line model identification.

A model that has been used to describe the relationship between training activity (input) and heart rate (output) is of the following general form, where y(t) is the time series of the measured output, u(t−nk) is the time series of the measured output, nk is the time delay between input and output and e(t) is the dynamic error term:

$$y(t) = \frac{B(q)}{F(q)}u(t-nk) + \frac{C(q)}{D(q)}e(t) \quad (2)$$

with $$F(q) = 1 + f_1 q^{-1} + \ldots + f_{nf} q^{-nf}$$

$$B(q) = b_1 + b_2 q^{-1} + \ldots + b_{nb} q^{-nb+1}$$

$$C(q) = 1 + c_1 q^{-1} + \ldots + c_{nc} q^{-nc}$$

$$F(q) = 1 + d_1 q^{-1} + \ldots + d_{nd} q^{-nd}$$

First of all, equation (2) is of remarkably similarity with equation (1 b) which relates physical and mental heart rate to the total (and measured) heart rate.

This can be written as follows:

$$y(t) = \frac{B(q)}{F(q)}u(t-nk) + \frac{C(q)}{D(q)}e(t) \quad (2)$$

$$HR_{tot} = HR_{phys} + HR_{PhAr} \quad (1b)$$

Hence:

$$HR_{phys} = \frac{B(q)}{F(q)}u(t-nk) \quad (3a)$$

$$HR_{PhAr} = \frac{C(q)}{D(q)}e(t) \quad (3b)$$

with $HR_{phys}$ and $HR_{PhAr}$ defined as in equations (1a) and (1b).

In modelling terms, this means that the transfer function that links the measured input directly to the measured output $$\left(\frac{B(q)}{F(q)}u(t-nk)\right)$$

in equation (2) describes the physical heart rate component. The arousal component of heart rate is then defined as the difference between the total hart rate (y in equation 2) and the physical heart rate component $$\left(\frac{B(q)}{F(q)}u(t-nk) \text{ in equation 2}\right).$$

This consequently also means that the error term $$\frac{C(q)}{D(q)}e(t)$$

in equation (2) contains that part of heart rate that is not directly linked to the training (physical) activity, and consists of predominantly arousal heart rate components. The reason for also attributing a transfer function model for the error term can be explained as follows. Consider the total error term from equation 2:

$$E(t) = \frac{C(q)}{D(q)}e(t)$$

With E(t) the total error term, e(t) the white noise error term and C(q) and D(q) as defined in equation (2). The typical structure of the total noise term E(t) of such a complex system can not be assumed to be purely white noise. There for, the error term e(t)—which is assumed to be white noise—is in term multiplied with a transfer function model structure to capture the non-white noise in the considered system. Remember the exactly the total error term $$\frac{C(q)}{D(q)}e(t)$$

is the difference between the total heart rate and its physical component, and thus equals the arousal component. This allows the arousal component of heart rate to fluctuate and change independently of the relation between total heart rate and activity, and even to fluctuate over different time levels (see further).

There exist several technical possibilities to solve this generic invention of the decomposition of total heart rate into a physical component based on on-line measurement and modelling of both a performance input variable and an arousal containing output variable like heart rate. The arousal component of heart rate is then defined as the difference between the total heart rate and the physical heart rate component. Hereunder two examples of technical solutions are presented, without constricting or limiting the invention to these.

A first technical example of real-time application of the generic decomposition of heart rate is through adaptive real-time modelling of the relation between input and output over a moving time window. At every time step, the relation between total heart rate and activity $$\left(\frac{B(q)}{F(q)}u(t-nk) \text{ in equation 2}\right)$$

is identified and the model parameters are estimated (FIG. 5). This enables calculation of that segment of heart rate that is directly linked with physical activity (equation 3a), the physical heart rate component. Hence, real-time calculation of the arousal component of heart rate(total heart−physical heart rate) is achieved.

One possible way to include basal metabolic heart rate and heart rate for heat balance is the following. Basal metabolic heart rate can be determined by a measurement in the morning. For instance a measurement of heart rate in the morning at the moment the person is waking up and still lying in bed, gives a good agreement with the basal metabolic heart rate. This basal metabolic heart rate can be considered constant during the time course of one day. The heart rate component for heat balance can be derived for each individual at every moment of the day based on the difference between his body temperature (e.g. measured by the torso's skin temperature) and the present and momentary environmental temperature.

As examples of this first technical solution, FIGS. 8A and 8B show the derivation of the arousal heart rate component based on on-line and continuous measurement of training activity and total heart rate. FIG. 8A shows, for a particular training exercise of 80 seconds, the measured total heart rate y(t) and the physical component of heart rate calculated from the identified transfer function model, by means of equation 3a. The (physiological) arousal component of heart rate for this exercise is the remaining part of the total heart rate that cannot be directly linked to the physical training activity (FIG. 8B).

A second technical example of real-time application of the generic decomposition of heart rate based on the difference in the dynamic behaviour of the model parameters of the physical and arousal component of heart rate.

When looking at the variation of the estimated model parameters that model the physical response of heart rate $$\left(\frac{B(q)}{F(q)}u(t-nk)\right)$$

and compare this with the variation of the estimated model parameters that model the arousal part $$\left(\frac{C(q)}{D(q)}e(t)\right),$$

then the arousal related parameters will vary much faster than the physical related parameters. This can be understood as follows: the model parameters that model the physical response of heart rate $$\left(\frac{B(q)}{F(q)}u(t-nk)\right)$$

are linked to the physical condition of an individual i.e. how an individual's heart rate responds to a particular activity or training effort. It is known in the art that physical condition of an individual can not change over a small period of time (e.g. a period of one up to more weeks). However, estimated model parameters that model the arousal part $$\left(\frac{C(q)}{D(q)}e(t)\right)$$

can change over every sample as a response to for instance acute stressors in the environment. FIG. 8C shows the variation of the model parameters over time for a specific physical training session. The model parameters that model the physical response of heart rate (B and F) do not vary a lot over this training session and their changes are relatively small. The model parameters that model the arousal response of heart rate (C and D) vary more over this training session and their changes are relatively higher.

An important consequence of the knowledge that the model parameters to model the physical status of the person cannot change in a short time period is the possibility to detect the use of doping by an athlete. It is possible to monitor the training inputs (e.g. power delivered during training on a bicycle) and process output (e.g. heart rate response of the cyclist) continuously during each training and sending this information to a database. The equipment to realise this is commercially available as for example the SRM measurement tools already used by most professional cyclist combined with telemetry and mobile and internet technology (See FIG. 9). Then the model can be calculated on how heart rate is responding to the delivered power which is the physical response of the heart rate to performance. This means that the value of the model parameters can be calculated continuously and they are a measure for the physical condition of the athlete. (FIGS. 9 and 10) This allows to follow continuously how the physical performance of the athlete is varying over time.

However, for each individual athlete the required training input and time period (e.g. 3 weeks) to improve the physical performance is known and can be stored in his individual dataset. It is also known that the physical status of the body cannot improve very fast (e.g. over a half day period) (FIG. 10). The only possible explanation of how these model parameters can change suddenly (e.g. in half a day instead of at least one or more weeks) is the use of doping. The technology to realise this method is fully available today. The data of all individual athletes can be transferred fully automatically to a central database where the software can run to detect the variation of the model parameters (FIG. 11) and signal suspicious changes.

Figure 3B:
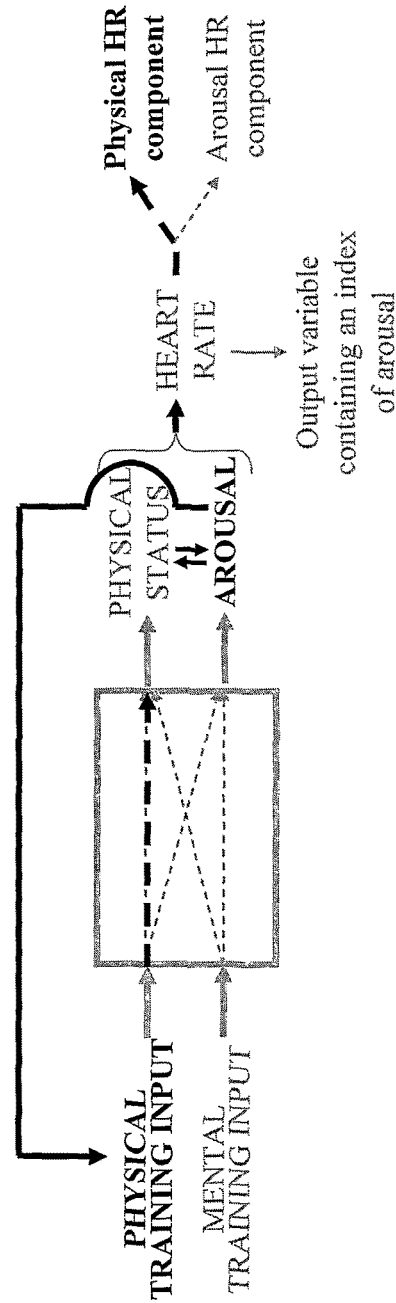

Based on this observation, the second technical example of real-time application of the generic decomposition of heart rate applies the following (FIGS. 8C, 8D). The model parameters that model the physical part are estimated on a clear physical effort (i.e. where the physical heart rate response is dominant) and these model parameters $$\frac{B(q)}{F(q)}u(t-nk)$$

are kept constant until the model is incapable of reliable predicting the output. Than of course a new physical model is estimated. While the physical model parameters are kept constant, the arousal component of heart rate(the difference between total heart rate and the physical component of heart rate) is modelled on every time step with a moving window (FIG. 3), allowing the arousal model $$\frac{C(q)}{D(q)}e(t)$$

to describe the difference between total heart rate and the physical component of heart rate (arousal component) as accurately as possible. A necessity in this technique is a reliable and accurate detection of dynamics in the input and/or output variables in order to estimate a physical model with as much dynamics in the physical heart rate as possible, and a few arousal heart rates as possible.

To detect dynamics in the system, one can use the system output (variable than contains an index for arousal, e.g. heart rate) but one can also use the system input (a performance related variable such as 3D accelerometer,). The assumption is made that all dynamics in system input need a dynamic response in the system output since e.g. every movement of the body needs metabolic energy to be delivered by a corresponding heart rate. However if dynamics is detected in heart rate as the system output without corresponding dynamics in the system input, than we know that the heart rate contains mainly arousal. Vice versa, if dynamics is detected in the system input than we know that we must assume that the output response contains a corresponding physical response.

Example 2: Individual and Real-Time Monitoring of Arousal of Athletes 2.1 Setup of the Experiment This example describes a methodology that was developed for monitoring and control of arousal of individuals. First of all, the mental or arousal component of heart rate is singled out based on the on-line and continuous measurement of training activity and total heart rate (see example 1).

Secondly, so-called 'emotional events' or 'arousal events' are calculated from the (physiological) arousal heart rate component.

The detection of emotional events starts from the calculated physical component of heart rate from on-line measured physical activity and on-line measured total heart rate. Based on this physical component of heart rate and the total heart rate, the arousal component of heart rate is calculated on-line by a real-time subtraction of the physical heart rate component from total heart rate. The occurrence of clear emotional events in the arousal component of heart rate is performed by a method comparable to a method proposed by Myrtek et al. (1999) who defines an emotional event based on total heart rate as follows: if the heart rate at time step t is 3 beats/min higher than the moving average of the past 3 minutes without a change in physical activity, than time step t contains a emotional event. The invention presented here differs in two ways with the prior art method. First, instantaneous calculation of the physical component of heart rate is used instead of measuring physical activity through motion sensors. Myrtek et al. (1999) themselves underline the necessity for an adequate baseline of heart rate to evaluate physical workload, but they offer no solution for this. The integration of the physical component of heart rate calculated from an individual's heart rate as is done here overcomes these shortcomings. Secondly, the dynamic behaviour of the arousal component of heart rate is used instead of the total heart rate to detect emotional events based on the moving average of 3 minutes and the distinctive increase of 3 beats/min. Any other means for determining emotion events in the arousal component of heart rate are not excluded by this invention.

Thirdly, the specific pattern of the mental or (physiological) arousal heart rate component is linked to either negative or positive emotional events. The dominant rule to distinguish negative and positive event in the arousal component of heart rate is based on following finding. We have shown that negative and positive events can be determined by the individual dynamic behaviour of the arousal component of heart rate. If the mean (physiological) arousal component of heart rate over a moving average of a certain time period (e.g. 4 minutes for football or soccer players) from the moment of the stimuli is higher that the arousal component of heart rate at the moment of the stimuli, the stimuli can be determined as a negative event.

Aside from this dominant determinant described above, a back-up scoring of negative and/or positive emotions is integrated, based on known procedures for such scoring. However, these procedures have always been applied on total heart rate (e.g. for individuals not involved in changing physical activity), while here negative and/or positive emotions are scored by applying these procedures to the arousal component of heart rate, which has been singled out first.

One described way to recognize negative emotions is delivered by Brosschot and Thayer (Brosschot and Thayer, 2003), which have shown that the latency of negative emotions is higher than the latency of positive emotions. This study showed that heart rate 5 minutes after an emotional event is higher that the heart rate at the time the emotional event occurred for a negative emotion. Similar, Anttonen and Surakka (2005) showed that especially the $6^{th}$ second from the stimulus onset and be used to distinct negative and positive stimuli.

Finally, this experimental approach is validated by comparing arousal determined by during activity by the here presented methods to arousal determined using state of the art traditional measures (i.e. bio-feedback variables such as temperature, ECG, EEG, EMG, Skin Conductance; blood and saliva hormones related to arousal (cortisol, Iga, . . . ), and specific scientific subjective questionnaires (POMS, RESTQ, . . . )).

2.2 Monitoring and Control of the Mental Status/Arousal Status of Professional Football (Soccer) Players The presented methodology and its capabilities for on-line monitoring the arousal status of individuals from on-line measurement of physical activity (input) and heart rate (output) is validated on professional soccer players. FIG. 12 shows the result of the developed mental/arousal monitor applied to a soccer game. The stems with positive values represent a minute with mainly positive emotions, while a stem with negative values represents a minute with mainly negative emotions. (Note that this is only for purposes of figure clarity: the actual arousal component has a positive value, it are the dynamics of the arousal component that are used to classify the value as due to positive or negative arousal). The double arrows at the bottom and top of FIG. 12 show the reference scoring of the arousal for this game (i.e. using traditional techniques, as described below). It is clear that the main trends from the reference agree with the type of arousal scored by the present particular embodiment.

In order to validate this methodology, there is a need for a scientific reference method for scoring the individual and time-variant (physiological) arousal. This scientific validation is performed by applying a scientific reference method for individual (physiological) arousal scoring. The momentaneous arousal status of an individual player is quantified based on psychophysiological and biofeedback variables, in combination with saliva hormones and scientific questionnaires.

Basically, all relevant scientific knowledge regarding arousal scoring is combined to this end. Amongst the measured variables are the typical bio-feedback variables (temperature, ECG, EEG, EMG, skin conductance, . . . ), blood and saliva hormones related to arousal (cortisol, Iga, . . . ), specific scientific subjective questionnaires (POMS, RESTQ,).

This way, a reliable and accurate scoring of the arousal status of an individual is obtained which is used as reference. This scoring reference is used for validation of the methods presented here where arousal status of an individual is derived based on the on-line measured physical activity and on-line measured total heart rate.

The arousal scoring technique starts from the calculated physical component of heart rate from on-line measured physical activity and on-line measured total heart rate. Based on this physical component of heart rate and the total heart rate, the arousal component of heart rate is calculated on-line by a real-time subtraction of the physical heart rate component from total heart rate. The occurrence of clear emotional events in the arousal component of heart rate is performed by a method as explained above.

For those time-steps that were scored as containing a non-metabolic or emotional event (i.e. an arousal event) in their heart rate, the physiological arousal component of heart rate is used to score these events being positive or negative, as explained above. Based on the above explained technique to calculate and score the arousal component of heart rate, each training session of the players is scored using a technique that takes into account the percentage and the magnitude of respectively negative and positive emotional (arousal) events in the arousal component of heart rate over a certain period of time to score the mental status of that individual during that certain time period. A session with more than 60 percent negative or positive emotional events is scored respectively as a negative and a positive session. All other sessions are scored based on the magnitude of both negative and positive emotion: if the negative emotions are relatively small compared to the positive emotions of the same session, this session is scored positive. If the positive emotions are relatively small compared to the negative emotion of the same session, this session is scored negative. If the negative emotions are relatively of the same magnitude as the positive emotions of the same session, this session is scored neutral.

The scores of the traditional mental variables (psycho physiological and biofeedback variables, in combination with saliva hormones and scientific questionnaires recorded after every training) were compared with the method presented here based on the arousal component of heart rate during the training. The results show that the methodology results in the desired properties: there is a 94% identity between the results obtained using the presented invention based on the arousal component of heart rate, calculated in real-time during training on the field, and the validation using multiple traditional variables after the training (FIG. 13A).

For sake of completeness, it was assessed whether the same result could be achieved using techniques known in the art. Indeed, some authors have already suggested that heart rate can be decomposed into e.g. an activity index (Moody, 1992). This was proposed to be able to minimize intra-patient heart rate variability.

The physical activity index proposed by Moody (1992) is calculated based on formula (4), with the scaling constants are fixed at $a_1=1$, $a_2=10$, $a_3=100$ and $Hr=40$, and the correction term for very low heart rate measurements c is set to 0, except in the situation where $HN(t)<25$ bpm, then c is equalled to 25 bpm$-$HN(t).

$$A(t) = c + \sqrt{a_1(H_N(t) - H_r)^2 + a_2 S(t)^2 + a_3 P(t)} \quad (4)$$

$$\text{with } H_N(t) = \frac{1}{2N} \sum_{n=-N}^{N-1} H(t + n\Delta t)$$

$$P(t) = \frac{1}{2N} \sum_{n=-N}^{N-1} (H(t + n\Delta t) - H_N(t))^2$$

$$S(t) = \left| H_{N/2}\left(t - \frac{N}{2}\Delta t\right) - H_{N/2}\left(t + \frac{N}{2}\Delta t\right) \right|$$

The Moody technique analyses the total heart rate as a three-dimensional space of mean heart rate $H_N(t)$, power in the heart rate $P(t)$ and stationarity of heart rate $S(t)$. By calculating the Euclidian distance between the constant resting heart rate and the momentary heart rate HR(t), an index of physical activity is derived.

When using the activity index according to Moody (1992) to score the individual and time-variant (physiological) arousal status as explained above, and when comparing these scores to the scores of the traditional reference (FIG. 13B), only 62% agreement is found with the state of the art control reference, instead of the 94% agreement when applying the currently presented method to score the individual and time-variant physiological arousal during activity (FIG. 13A).

This clearly demonstrates the added value of the presented technique for decomposition of heart rate into a (mental or) arousal and physical component.

While this example related to the monitoring of the arousal component, it should be stressed that the physical component of the index of arousal can be monitored and controlled in a similar way. In that case, the physical component of heart rate is singled out (see example 1). This will be illustrated in Example 3, but it is to be understood that both physical and arousal components of the index of arousal can be monitored and/or controlled on the same individual at the same time.

Example 3: Monitoring and Management of Physical Performance of Sport Athletes

FIG. 14A shows a general representation of how bioprocess control can be achieved for the example of a cyclist.

3.1 Materials and Methods

Test Installation

The experiments were performed on an ergometer (Tunturi T8). The ergometer was placed in a wind tunnel with dimensions of 2.3 m×1.5 m×2.1 m. The back wall of the wind tunnel consisted of 12 ventilators (fancom type 1435). A schematic overview is shown in FIG. 14B. The ergometer was connected to a computer via a LAN link and the time course of the effort level could be programmed (T-ware software). Every 5 seconds the following variables were logged: heart rate (bpm), cadence (1/minute) and effort level (W). For the heart rate measurement the cyclist had to wear a Polar T31 transmitter.

Experiments

First of all, for all experiments the physical component of heart rate was singled out and used for further analyses (see Example 1).

Two types of experiments were performed. A first series of experiments was used to model the physical component of heart rate response to variations in cadence of two test persons. In a second series of experiments the developed physical component of heart rate control algorithm was tested.

Modelling Experiments

In this example the modelling experiments were performed with two test persons. Test person 1 was a 20 years old male with a length of 1.90 m and a weight of 72 kg. Test person 2 was a 21 years old man with a length of 1.84 m and a weight of 85 kg. Both test persons sported frequently.

Each experiment lasted 60 minutes and all variables were stored with a time interval of 20 seconds resulting in 180 samples per experiment. During each experiment a step in cadence was applied. The procedure was as follows: the first 10 minutes cycling at cadence 1; the next 20 minutes cycling at cadence 2; the last 30 minutes cycling at cadence 1 again. Three different step changes in cadence were performed: 1) cadence 1:60, cadence 2:70; 2) cadence 1:60, cadence 2:80; 3) cadence 1:70, cadence 2:80. Each experiment was repeated four times by each test person resulting in (4×4×2) 32 step experiments. The effort level was set constant during the tests to 15 Nm.

Control Experiments

The control algorithm was tested on test person 2. Test person 1 operated the computer with the control algorithm. Four different trajectories in heart rate were defined.

Trajectory 1: 20 minutes at constant 120 bpm, 20 minutes linearly increasing to 150 bpm, and 20 minutes at constant 150 bpm.

Trajectory 2: 15 minutes at constant 120 bpm, 10 minutes linearly increasing to 140 bpm, 10 minutes at constant 140 bpm, 15 minutes linearly decreasing to 130 bpm, and 10 minutes at constant 130 bpm.

Trajectory 3: 10 minutes at constant 120 bpm, 10 minutes linearly increasing to 140 bpm, 10 minutes at constant 140 bpm, 10 minutes linearly decreasing to 120 bpm, 10 minutes at constant 120 bpm, 10 minutes linearly increasing to 140 bpm, 10 minutes at constant 140 bpm, 10 minutes linearly decreasing to 120 bpm, 10 minutes at constant 120 bpm.

Trajectory 4: 10 minutes at constant 120 bpm, 10 minutes linearly increasing to 140 bpm, 10 minutes at constant 140 bpm, 10 minutes linearly decreasing to 130 bpm, 10 minutes at constant 130 bpm, 10 minutes linearly increasing to 150 bpm, 10 minutes at constant 150 bpm, 10 minutes linearly decreasing to 120 bpm, 10 minutes at constant 120 bpm, 10 minutes linearly increasing to 140 bpm, 10 minutes at constant 140 bpm, 10 minutes linearly decreasing to 120 bpm, 10 minutes at constant 120 bpm, 10 minutes linearly increasing to 150 bpm, 10 minutes at constant 150 bpm, 10 minutes linearly decreasing to 130 bpm, 10 minutes at constant 130 bpm.

Modelling

In this example a single-input single-output (SISO) linear discrete transfer function model was used to describe the dynamic response of the total heart rate to cycling frequency (cadence). It had the following general structure:

$$y(t) = \frac{B(q)}{A(q)} u(t-nk) + \frac{C(q)}{D(q)} e(t) \quad (2)$$

where y(q) is the total heart rate (bpm) at time q u(q) is the input cadence (1/minute) at time q; e(q) is dynamic noise component, q is the time in s; B(q), A(q), C(q) and D(q) are polynomials with model parameters given by:

$$B(z^{-1}) = 1 + b_1 z^{-1} + b_2 z^{-2} + \ldots + b_{na} z^{-nb}$$

$$A(z^{-1}) = a_0 + a_1 z^{-1} + a_2 z^{-2} + \ldots + a_{nb} z^{-na}$$

$$C(z^{-1}) = 1 + c_1 z^{-1} + d_2 z^{-2} + \ldots + c_{na} z^{-nc}$$

$$D(z^{-1}) = d_0 + d_1 z^{-1} + d_2 z^{-2} + \ldots + d_{nb} z^{-nd}$$

where $a_j$, $b_j$, $c_j$, $d_j$ are the model parameters to be estimated; $z^{-1}$ is the backward shift operator, $z^{-1} \cdot y(k) = y(k-1)$; na, nb, nc, nd are the orders of the respective polynomials.

The transfer function that links the measured input directly to the measured output $$\left(\text{i.e. } \frac{B(q)}{A(q)} u(t-nk) \text{ in equation 2}\right)$$

describes the physical heart rate component. With measured input data and the online identified transfer function $$\frac{B(q)}{A(q)} u(t-nk)$$

the physical component of heart rate can be calculated on-line and continuously. It is only this physical component of heart rate $$\frac{B(q)}{A(q)} u(t-nk)$$

that the present example uses for modelling and monitoring of the physical performance of sport athletes, and that is used in the following descriptions of this section.

The model parameters of $$y_{phys} = \frac{B(q)}{A(q)} u(t-nk)$$

were estimated using a refined instrumental variable approach (Young, 1984). For each data set, the model parameters of Eqn. (2) were estimated and the resulting models were evaluated by the coefficient of determination $r^2$.

The modelling was carried out in Matlab® (version 7.0.1, The MathWorks Inc., Natick, Mass., U.S).

Control Algorithm

In this research we used model-based predictive control theory to control the heart rate of the cyclist by means of the control input cadence by using continuous feedback of the process input and output and making an explicit use of a model of the process to calculate the control signal by minimizing an objective function (Soeterboek, 1990; Camacho & Bordons, 1999). The general expression for the objective function is (Camacho & Bordons, 1999):

$$J(N_1, N_2, N_u) = \sum_{j=N_1}^{N_2} \delta(j)[\hat{y}(k+j|k) - r(k+j)]^2 + \sum_{j=1}^{N_u} \lambda(j)[\Delta u(k+j-1)]^2 \qquad (5)$$

where: $N_1$ is the minimum cost horizon; $N_2$ is the maximum cost horizon; $N_u$ is the control horizon, $\hat{y}(k+j|k)$ is the model-based predicted value of the process output y at time k, j time steps in the future; r(k+j) is the value of the reference or target trajectory at moment k+j; $\Delta u(k+j-1)$ is the change of control inlet at moment k+j−1 and $\delta(j)$, $\lambda(j)$ are weighting coefficients. In this research, the objective function was defined as:

$$J(1, 3, 3) = \sum_{j=N_1}^{3} \delta(j)\left[\hat{H}R(k+j|k) - r(k+j)\right]^2 + \sum_{j=1}^{3} \lambda(j)[\Delta v(k+j-1)]^2 \qquad (6)$$

where $\hat{H}R(k+j|k)$ is the physical component of heart rate of the cyclist in bpm predicted by the dynamic model of Eqn. (2); v is the cadence in 1/minute and r is the reference or target heart rate trajectory in bpm. The minimum cost horizon $N_1$ was set to 20 seconds and both the maximum cost horizon $N_2$ and the control horizon $N_u$ were set to 60 seconds. The weighting coefficients $\delta$ and $\lambda$ were set to 1 and 0.8 respectively.

Minimization of this cost function allowed to calculate the needed cycling speed in order to follow the previously target heart trajectory as close as possible.

3.2 Results

Based on the data of the step experiments it was demonstrated that the physical components of heart rate responses to variations in cadence can be modelled accurately by means of a first order transfer function model. In Table 3.1 an overview of the modelling accuracies in terms of $r^2$ are shown. Table 3.2 presents an overview of the errors between the target and the controlled physical component of heart rate trajectory. Further illustrations of the results are shown in FIG. 15

TABLE 3.1

Summary of the modelling results in terms of $R^2$.

| | | Step 60 - 70 - 60 | |
|---|---|---|---|
| | | Step up | Step down |
| Test person 1 | Test 1 | 0.78 | 0.56 |
| | Test 2 | 0.72 | 0.57 |
| | Test 3 | 0.79 | — |
| | Test 4 | 0.43 | 0.40 |
| Test person 2 | Test 1 | 0.86 | 0.51 |
| | Test 2 | 0.74 | — |
| | Test 3 | 0.58 | 0.46 |
| | Test 4 | 0.65 | — |

| | | Step 70 - 80 - 70 | |
|---|---|---|---|
| | | Step up | Step down |
| Test person 1 | Test 1 | 0.84 | 0.51 |
| | Test 2 | 0.76 | 0.21 |
| | Test 3 | 0.69 | 0.72 |
| | Test 4 | 0.81 | 0.68 |

TABLE 3.1-continued

Summary of the modelling results in terms of $R^2$.

| | | | |
|---|---|---|---|
| Test person 2 | Test 1 | 0.76 | — |
| | Test 2 | 0.63 | 0.59 |
| | Test 3 | 0.63 | — |
| | Test 4 | 0.65 | 0.38 |

| | | Step 60 - 80 - 60 | |
|---|---|---|---|
| | | Step up | Step down |
| Test person 1 | Test 1 | 0.92 | 0.88 |
| | Test 2 | 0.92 | 0.86 |
| | Test 3 | 0.96 | 0.88 |
| | Test 4 | 0.90 | 0.81 |
| Test person 2 | Test 1 | 0.89 | 0.60 |
| | Test 2 | 0.88 | 0.50 |
| | Test 3 | 0.85 | 0.72 |
| | Test 4 | 0.90 | 0.66 |

TABLE 3.2

Overview of the errors between the target and the controlled physical component of heart rate trajectory (bpm) expressed as means (±stdev).

| | Test 1 | Test 2 | Test 3 | Test 4 |
|---|---|---|---|---|
| Trajectory 1 | 1.1 (±3.5) | 0.5 (±4.0) | 0.4 (±3.7) | 0.6 (±3.7) |
| Trajectory 2 | 0.4 (±3.5) | 0.4 (±3.2) | 0.4 (±3.3) | 0.1 (±3.6) |
| Trajectory 3 | 0.1 (±4.7) | 0.1 (±4.6) | | |
| Trajectory 4 | 0.8 (±4.9) | 0.3 (±4.8) | | |

In addition to the control of the physical component of heart rate, it should be noted that it is possible at the same time to monitor and/or control the arousal component, using the methods as outlined in examples 1 and 2.

Example 4: Controlling Physiological Responses of Horses as a Basis for Performance Improvement 4.1 Introduction Compared to other sports, not much has been changed in the physical performance of athletic horses in the last century (Fregin and Thomas, 1983). Also the training methods have not evolved significantly (Gabel et al., 1983). In order to achieve a good combination of welfare and performance, it is important to have a good idea about the tolerance and the functional status (metabolic, cardiovascular, haematological, etc.) of athletic horses. Many physiologic variables that can be measured (on-line) in horses are valuable for determining the level of training, indicating health status and physical condition. Therefore, it would be an advantage if such variables could be, not only measured, but also analyzed on-line, allowing to optimize the training regime of the horse.

The recent (r)evolution in hardware and software makes it now possible to measure biological signals directly and on-line on living organisms and to process these signals by means of powerful algorithms (Aerts et al., 2003a,b). It is expected that such engineering approach applied to biological systems (from the sub cellular to the macro scale) will result in important developments in biology and medicine and is called 'systems biology' (Csete and Doyle, 2002; Kitano, 2002; Hood et al., 2004).

By coupling sensors for on-line measurement with compact processors (e.g. PDA) and on-line modelling/control algorithms, it should be possible to monitor and control physiological variables on the horse in an on-line way (during training or competition).

In this research, the objective was to explore the possibilities of using modern model-based algorithms to control the heart rate of horses (bpm) on-line by means of the control input running speed (km/h).

Forty-five experiments with five horses were carried out in order to generate measurements of physiological status during running. On the basis of these data, the dynamical characteristics of the different horses were quantified using mathematical models. In a next step, cardiac responses of two horses were controlled to a pre-defined target level by making use of the dynamical information of the individual horses. The relative control error for the two horses was on average 5%.

In the future, such an approach can be used for adjusting the work load of the horse, during training, directly to the immediate needs of horse (welfare) and trainer (performance).

4.2 Materials and Methods

Horses

In this research five horses were used. In Table 4.1, the characteristics of the horses are summarized. Horse 1 up to 4 were mares, horse 5 was a gelding.

TABLE 4.1

Overview of the used horses.

| | Height of the withers (m) | Weight (kg) | Type |
|---|---|---|---|
| Horse 1 | 1.78 | 617 | Belgian warmblood |
| Horse 2 | 1.68 | 592 | Selle Français |
| Horse 3 | 1.72 | 617 | Mecklenburg-Vorpommeren |
| Horse 4 | 1.60 | 601 | Selle Français |
| Horse 5 | 1.66 | 530 | Belgian warmblood |

Riders

The horses were rode by four riders. Data on the riders are summarized in Table 4.2. Riders 1 and 2 were men, riders 3 and 4 were women.

TABLE 4.2

Overview of the riders.

| | Length (m) | Weight (kg) | Experience (years) |
|---|---|---|---|
| Rider 1 | 1.74 | 64 | 7 |
| Rider 2 | 1.80 | 78 | 22 |
| Rider 3 | 1.74 | 65 | 12 |
| Rider 4 | 1.63 | 50 | 14 |

Sensors

Heart Rate.

The heart rates of the horses were measured by means of a Polar® S610i™ sensor (Polar Electro Oy, Kempele, Finland). The electrical heart signals were measured on the skin by means of two electrodes of the Polar® Equine T52H transmitter that sent the data to the watch. Heart rates were stored in the watch with a time interval of 5 seconds. The transmitter was attached to the saddle. The watch was worn by the rider. The positive electrode was attached to the skin under the saddle at the level of the withers. The negative electrode was placed at the level of the elbow joint under the saddle belt. Where the electrodes were attached, the coat was shaved. In order to improve the conductivity of the electrical signals between the skin and the electrodes, the skin was moistened by water. After each experiment, the data were transmitted from the watch to a PC by means of an infrared link. The data were first read in the software Polar® Equine SW4 and further processed in Matlab® (version 7.0.1, The MathWorks Inc., Natick, Mass., U.S). The absolute accuracy was 1±3.7 bpm.

Running Speed.

The running speed of the horse was measured by means of a Garmin® Forerunner™ 201 (Garmin Ltd., Romsey, U.K.). This GPS measured the position, the speed, and the travelled distance based on the data of maximum 12 satellites. The sample frequency was not constant and was influenced by the shape of the travelled trajectory. The GPS was attached to the saddle. After each experiment, the data could be transferred to a PC by means of a serial link. The relative error for the speed determination was 0.34%.

4.3 Experiments

Step Experiments.

In order to quantify the dynamic characteristics of the heart rate responses of horses, in total 45 step experiments were carried out with the five horses and the four riders. These experiments were used to develop a dynamic data-based model for each individual horse that could be used as a basis for controlling the heart rate. In Table 4.3 an overview is shown of the 45 step experiments with the different combinations of horses and riders. Every horse did nine step experiments (three repetitions with three riders). Each experiment consisted of five minutes of walking, 10 minutes of trotting and again 10 minutes of walking. The running velocities were not set to a fixed value for all horses, but were determined for each individual horse based on pre-experiments in order to let the horses run in a comfortable way.

TABLE 4.3

Overview of the 45 step experiments.

| | Horse 1 | Horse 2 | Horse 3 | Horse 4 | Horse 5 |
|---|---|---|---|---|---|
| Rider 1 | 3 | 3 | 3 | 3 | 3 |
| Rider 2 | 3 | | | 3 | 3 |
| Rider 3 | 3 | 3 | 3 | 3 | 3 |
| Rider 4 | | 3 | 3 | | |

Heart Rate Control Experiments.

For these experiments, horses 2 and 4 were used. Both were ridden by rider 3. For each horse a heart rate trajectory was defined based on the previous step experiments. Each heart rate control experiment was performed three times per horse.

These experiments were performed by two persons, namely the horse rider whose task was to let the horse run at the speed determined by the control algorithm and the second person who operated the PC with the control algorithm. More specifically, every 20 seconds the rider read the values for heart rate and running speed from the sensors and reported these to the operator. The operator read these values immediately into the control algorithm and communicated the new value of running speed, calculated in a second by the control algorithm, to the rider who adjusted the running speed of the horse to this new value. In this way, the calculations and the control actions were performed every 20 seconds.

Modelling

We used a single-input single-output (SISO) linear discrete transfer function model to describe the dynamic response of the heart rate to running speed. It had the following general structure:

$$y(t) = \frac{B(q)}{A(q)}u(t-nk) + \frac{C(q)}{D(q)}e(t) \quad (2)$$

where y(q) is the total heart rate (bpm) at time q u(q) is the input cadence (1/minute) at time q; e(q) is dynamic noise component, q is the time in s; B(q), A(q), C(q) and D(q) are polynomials with model parameters given by:

$$B(z^{-1}) = 1 + b_1 z^{-1} + b_2 z^{-2} + \ldots + b_{nd} z^{-nb}$$

$$A(z^{-1}) = a_0 + a_1 z^{-1} + a_2 z^{-2} + \ldots + a_{nb} z^{-na}$$

$$C(z^{-1}) = 1 + c_1 z^{-1} + d_2 z^{-2} + \ldots + c_{nd} z^{-nc}$$

$$D(z^{-1}) = d_0 + d_1 z^{-1} + d_2 z^{-2} + \ldots + d_{nb} z^{-nd}$$

where $a_j$, $b_j$, $c_j$, $d_j$ are the model parameters to be estimated; $z^{-1}$ is the backward shift operator, $z^{-1} \cdot y(k) = y(k-1)$; na, nb, nc, nd are the orders of the respective polynomials.

The model parameters were estimated using a refined instrumental variable approach (Young, 1984). For each data set, the model parameters of Eqn. (2) were estimated and the resulting models were evaluated by the coefficient of determination $r^2$.

Control Algorithm

In this research we used model-based predictive control theory to control the heart rate of the cyclist by means of the control input cadence by using continuous feedback of the process input and output and making an explicit use of a model of the process to calculate the control signal by minimizing an objective function (Soeterboek, 1990; Camacho & Bordons, 1999). The general expression for the objective function is (Camacho & Bordons, 1999):

$$J(N_1, N_2, N_u) = \sum_{j=N_1}^{N_2} \delta(j)[\hat{y}(k+j|k) - r(k+j)]^2 + \sum_{j=1}^{N_u} \lambda(j)[\Delta u(k+j-1)]^2 \quad (5)$$

where: $N_1$ is the minimum cost horizon; $N_2$ is the maximum cost horizon; $N_u$ is the control horizon, $\hat{y}(k+j|k)$ is the model-based predicted value of the process output y at time k, j time steps in the future; $r(k+j)$ is the value of the reference or target trajectory at moment k+j; $\Delta u(k+j-1)$ is the change of control inlet at moment k+j−1 and $\delta(j)$, $\lambda(j)$ are weighting coefficients. In this research, the objective function was defined as:

$$J(1, 3, 3) = \sum_{j=N_1}^{3} \delta(j)\left[\hat{H}R(k+j|k) - r(k+j)\right]^2 + \sum_{j=1}^{3} \lambda(j)[\Delta v(k+j-1)]^2 \quad (6)$$

where $\hat{H}R(k+j|k)$ is the physical component of heart rate of the cyclist in bpm predicted by the dynamic model of Eqn. (2); v is the cadence in 1/minute and r is the reference or target heart rate trajectory in bpm. The minimum cost horizon $N_1$ was set to 20 seconds and both the maximum cost horizon $N_2$ and the control horizon $N_u$ were set to 60 seconds. The weighting coefficients $\delta$ and $\lambda$ were set to 1 and 0.8 respectively.

Minimization of this cost function allowed to calculate the needed running speed in order to follow the previously target heart trajectory as close as possible.

4.4 Results

Modelling Heart Rate Response

The dynamic response of heart rate to steps up and down in running speed could be described accurately by means of a transfer function model (cf. table 4.4 and 4.5). In 90% of the cases, a first order model gave the best fit. For 69% of the models, the $r^2$ was higher than 0.90 and for 34% of the models, the $r^2$ was even higher than 0.95. The time delay between the heart rate response and the change in running speed was predominantly zero indicating that the heart rate responded within five seconds (one time interval) after a change in running speed.

TABLE 4.4

Modelling results of the 45 step experiments (per horse per rider in three repetitions) in terms of the coefficient of determination $r^2$ for the step up in heart rate.

| | Horse 1 | Horse 2 | Horse 3 | Horse 4 | Horse 5 |
|---|---|---|---|---|---|
| Rider 1 | 0.87, 0.84 0.73 | 0.78, 0.90 0.92 | 0.95, 0.92 0.95 | 0.95, 0.92 0.93 | 0.93, 0.89 0.78 |
| Rider 2 | 0.92, 0.77 0.89 | | | 0.85, 0.90 0.93 | 0.94, 0.88 0.88 |
| Rider 3 | 0.95, 0.82 0.94 | 0.93, 0.93 0.90 | 0.96, 0.96 0.95 | 0.93, 0.88 0.93 | 0.63 0.80, 0.87 |
| Rider 4 | | 0.94, 0.95 0.94 | 0.96, 0.80 0.88 | | |

TABLE 4.5

Modelling results of the 45 step experiments (per horse per rider in three repetitions) in terms of the coefficient of determination $r^2$ for the step down in heart rate.

| | Horse 1 | Horse 2 | Horse 3 | Horse 4 | Horse 5 |
|---|---|---|---|---|---|
| Rider 1 | 0.94, 0.96 0.95 | 0.75, 0.95 0.96 | 0.97, 0.97 0.95 | 0.95, 0.97 0.96 | 0.96, 0.96 0.92 |
| Rider 2 | 0.92, 0.82 0.96 | | | 0.95, 0.91 0.97 | 0.88, 0.91 0.74 |
| Rider 3 | 0.98, 0.91 0.81 | 0.95, 0.98 0.92 | 0.99, 0.97 0.98 | 0.97, 0.95 0.95 | 0.80, 0.96 0.95 |
| Rider 4 | | 0.96, 0.95 0.96 | 0.96, 0.93 0.93 | | |

Control Heart Rate Response

For horses 2 and 4, the heart rate was controlled on the basis of a model-based control algorithm (cf. Eqn. 6). In FIG. 16 an example is shown of the control results for race horse 4. As can be seen in the figure, heart rate could be controlled quite accurately. On average, the error between the defined target trajectory in heart rate and the actual controlled heart rate ranged between 0.2 and 1.4 bpm for the whole target heart rate trajectory. During the steady state part of the trajectory the average error was maximum 1.1 bpm. In the transient from one steady state in heart rate level to another level, the error could increase on average up to 5 bpm. This can be mainly explained by the fact that the horses could not run comfortably between the low level heart rate level (walk) and the higher level heart rate level (trot). A more detailed overview is given in table 4.6.

TABLE 4.6

Overview of the control errors of the heart rate controller for horses 2 and 4.

|  | Whole target trajectory | | Steady state target trajectory | | Transient target trajectory | |
| --- | --- | --- | --- | --- | --- | --- |
|  | Average (bpm) | SE (bpm) | Average (bpm) | SE (bpm) | Average (bpm) | SE (bpm) |
| Horse 2, trial 1 | −1.8 | 7.3 | −0.7 | 4.8 | −5.0 | 11.6 |
| Horse 2, trial 2 | −0.3 | 4.6 | −0.1 | 2.9 | −1.0 | 7.6 |
| Horse 2, trial 3 | −1.4 | 6.6 | −1.1 | 6.1 | −2.2 | 7.8 |
| Horse 4, trial 1 | −0.6 | 4.2 | −0.6 | 3.2 | −0.8 | 6.3 |
| Horse 4, trial 2 | −0.2 | 3.3 | 0.0 | 2.2 | −0.8 | 5.3 |
| Horse 4, trial 3 | −0.2 | 3.5 | −0.3 | 2.5 | 0.4 | 5.4 |

In all the experiments, the rider was able to adjust the running speed of the horses with an error of 0.5 to 1.0 km/h.

Conclusion

The combination of on-line measurements of biological signals with advanced control algorithms enable to control complex physiological processes such as heart rate responses. Such an approach could be used for adjusting the work load of the horse, during training, directly to the immediate needs of horse (welfare) and trainer (performance). Moreover, in addition to the physical component of the heart rate, the arousal component of heart rate can be monitored continuously, so that the welfare of the horse can further be increased. Arousal of the horse will for instance typically depend on the rider, on conditions that may frighten the horse, etc. As demonstrated in Examples 1 and 2, the arousal component of heart rate can be monitored separately, in addition to the physical component of heart rate.

Example 5: Early Detection of Sleepiness in an Active Subject

Introduction

This example relates to the detection of sleepiness in active subjects based on a specific embodiment of the methodology currently provided. For several output variables (heart rate, thermoregulatory rhythm and individual bio-rhythm), first the metabolic component is calculated based on an on-line adaptive model between a metabolic related input variable and the considered out variable. Next, the arousal component of the considered variable is real-time calculated as the difference between the considered output variable and its respective physical component. The obtained arousal components of the respective output variables are then used as input variables in a second model that monitors and predict the output variable sleepiness in real-time (FIG. 17).

A clear and undeniable link exists between sleepiness in active subjects (as defined in the following paragraphs) and arousal. A situation in which an individual is sleepy congregates with a situation of low arousal, and vice versa, a situation in which an individual is experiences a low level of sleepiness indicates a high level of arousal for that individual. Normal to Excessive Sleepiness in an Active Subject (NESAS) is function of and determined by the arousal level of the individual. This means that the (physiological) arousal component of heart rate (see example 1) can be calculated to be further used as model input in order to quantify and monitor the performance level with regard to Normal to Excessive Sleepiness in an Active Subject.

It is important to distinguish between active and non-active subjects (subject is used as synonym for individual human or animal, in the present examples, individual humans are monitored). A non-active subject can be defined as one who is making an effort to actually fall asleep. An active subject can be defined as a subject who is performing an activity, whereby the mentioned activity can require intensive physical activity (working, running, . . . ), or not (sitting, reading, . . . ). The principal criterion for an active subject is the intention to remain awake and perform, or to be 'active' and perform. An active subject who experiences sleepiness will fight the onset of sleep and strives for remaining mentally alert. Not only are the processes of sleepiness in non-active subjects (attempted sleep) and sleepiness in active subjects (struggle against sleep) characterised by distinct circumstances (cognitive effort to sleep/stay awake, posture, lighting conditions, . . . ), their very nature is substantial different which is expressed through discrepancies in sleep propensity scoring methods (e.g. Sangal et al., 1992) and cognitive responses to arousal (e.g. DeValck et al., 2004). The present example relates to normal to excessive sleepiness in active subjects.

Normal sleepiness is defined as all forms of sleep not comprised by the process of attempted sleep, while excessive sleepiness for the purpose of present is defined as the overwhelming and recurring need to sleep at times when a person really wants to be awake. It translates itself into having a low level of arousal, having difficulty in maintaining wakefulness and an increased likelihood of falling asleep in inappropriate situations. Excessive sleepiness refers to a propensity to fall asleep, nod or doze easily in relaxed or sedentary situations, or a need to exert extra effort to avoid sleeping in these situations. In addition to just normal or mild sleepiness, the excessive sleepiness can cause related symptoms, including poor memory, reduced concentration or attention, performance decrements and irritability. A person experiencing excessive sleepiness can suddenly fall into a sleep state with almost no warning whatsoever. Sleep attacks can occur at any time, even in mid-conversation, and many times a day.

Normal to Excessive Sleepiness in an Active Subject (NESAS) in this example means (excessive) unwanted sleepiness or tendency to fall asleep which occurs in an active subject or a subject at work. It concerns situation where an individual experiences low arousal and is susceptible to performance decrements due to his/her low level of arousal.

SUMMARY

The present example relates generally to an early warning system based on an index of arousal for Normal to Excessive Sleepiness in an Active Subject (NESAS) as opposed to the normal transition from wakefulness to sleep at bedtime. In particular, biological responses from the driver's body such as peripheral heat loss, physiological component of heart rate, biorhythm and driving performance are used as a monitor and early predictor for NESAS. Sensors integrated into interior of a transportation system or working environment, or intelligent finger clips, or intelligent gloves, or intelligent textiles or measurement of biological responses from the driver's body (peripheral heat loss, heart rate, biorhythm and driving performance). The signal is telemetrically transmitted to a central processing unit where individual NESAS is monitored, with the possibility to detect and predict alarming situations. This is particularly useful in situations of low external stimulation where alertness is required, and will enable on-line and centralized monitoring and evaluation of people performing a demanding task.

FIG. 17 draws the global methodology behind the predictive driver sleepiness monitor that feeds on 1) the decomposition of total heart rate into a physical and arousal component and on 2) a continuous feedback of information from the individual driver (biorhythm, heat balance and driving performance). The method for detection and prediction of NESAS is based on the decomposition of total heart rate in a physical and arousal component via a real-time adaptive model between on-line measurement data of the driver's activity (body movements, movements in the seat, etc) and of the driver's total heart rate. From this, the (physiological) arousal component of heart rate is combined with other on-line recorded output bio-response variables (biorhythm, heat balance and driving performance) to come to an individual index of arousal (or an index of sleepiness).

The present example thus describes a method for continuous monitoring, detection and prediction of NESAS, based at least in part on the arousal component of heart rate (determined first using the model allowing decomposition of heart rate). This allows in time detection of NESAS, even before the effect of this (normal to excessive) sleepiness is visible through a decrease in performance (e.g. driving simulator) or vigilance decline. Not only the recording of the signals, but also the analysis and model identification of the signals is performed in real-time so that handling of the subject's CITD behaviour can be guaranteed.

Description of Variables

Several variables that are known to diverge from their normal course and function in close relation to the event of sleepiness/arousal are monitored separately for signs of sleepiness/low arousal. The considered variables are signs of (absence of) arousal in the arousal component of heart rate, in the heat balance based Distal-to-Proximal-to-Microenvironmental Gradient (DPMG), in the individual and time-varying biorhythm and in driving performance.

A. Arousal Component of Heart Rate and Sleepiness/Arousal

On-line Heart rate and physical activity are used to calculate the physical component of heart rate, and hence the (physiological) arousal component of heart rate as explained above (e.g. Example 1).

The arousal component of heart rate of every minute is for this example compared to the moving average of the previous 3 min in order to detect so-called 'emotional events', in accordance with the monitoring technique described by Myrtek et al. (Myrtek et. al, 1999). But with the addition of solely using the (physiological) arousal component of heart rate and not the total heart rate signal. An emotional event is postulated as that situation where the heart rate of a given minute is at least 3 beats per minute greater than the moving average of the previous minutes with little or no increase in physical activity. If the individually and on-line measured physical activity increases, the minimal additional heart rate required to indicate an emotional event (HRPLUS) increases as well, according to Myrtek et al. (1999).

For all subjects from a sleep laboratory study, the occurrence of emotional or arousal events in the arousal component of heart rate is calculated during their 25 minutes simulator drive. For example, FIG. 18 visualizes the occurrence of emotional or arousal events in the arousal component of heart rate of a sleepy driver (left) and of a non sleepy (right) driver. The sleepy driver experiences clear emotional events while driving, indicating a loss of concentration and alertness. The non sleepy driver experiences not one emotional event during driving a vehicle, indicating high arousal and concentration during his task.

Table 5.1 compiles the results from the sleep laboratory study and the shift workers study. On a total of 24 subjects suffering from emotional (arousal) events in the arousal component of heart rate while driving, 22 (92%) are scored as sleepy drivers based on their EEG data or on subjective sleepiness scoring through the Stanford Sleepiness Scale. From the 34 subjects unaffected by emotional (arousal) events in the arousal component of heart rate, 21 are categorized as not subject to driver sleepiness. In classification terms, on a total of 58 subjects included in the study, 74% is correctly classified based on the calculated emotional HR.

TABLE 5.1

Overview of presence of sleep/no sleep in relation to the occurrence of emotional events (EE) in the physiological arousal component of heart rate for both datasets.

| | Number of subjects | True positive | False positive | Percentage correct |
|---|---|---|---|---|
| EE | 24 | 22 | 2 | 92% |
| No EE | 34 | 21 | 13 | 62% |
| Overall | 58 | 43 | 15 | 74% |

True positive indicates a correct classification; false positive indicates an incorrect classification.

B. Peripheral Heat Loss and Sleepiness/Arousal

The sleep process is subject to circadian variations (biorhythm), and is thoroughly linked with the arithmetic of core body temperature. Even more, the core body temperature's time course shows a functional link with both subjective sleepiness and the ability to initiate sleep (Campbell et al. 1994). Sleep initiation typically occurs when the circadian core body temperature rhythm is declining (Czeisler et al. 1980, Zulley et al. 1981, Dijk et al. 1995) and sleep onset latency (i.e. time needed to fall asleep) declines rapidly as core body temperature decreases and is shortest around the circadian core body temperature minimum.

One of the key physiological mechanisms behind the circadian variations in core body temperature is peripheral heat loss. More specifically, increased peripheral heat loss is the primary contributor to the evening decline in core body temperature associated with sleep initiation (Krauchi et al. 1994, Van Someren 2000). These thermoregulatory changes in core body temperature and peripheral heat loss are known to interact with the process of human sleep (Magnussen 1943, Kleitman et al. 1948, Brown 1979, Krauchi et al. 1999, Lack et al. 2002). In fact, peripheral heat loss is quantified as the best indicator for short sleep onset latency at normal bedtimes (Kanda et al. 1999, Krauchi et al. 2000, Sung et al. 2000). Skin regions at the body's extremities show increases in temperature during the 1.5 h period before sleep onset (Kleitman et al. 1948, Brown 1979, Collins et al. 1995, Krauchi et al 1997b, Van Den Heuvel et al. 1998, Kubo et al. 1999). Peripheral temperature changes that occur before or at sleep onset are also influenced by characteristics like lack of sleep, sleep disorder (Morris et al. 1990, Pache et al. 2001), ageing (Weitzman et al. 1982, Lushington et al. 2000), etc. The theorem that the sleep process is to some extent regulated by thermoregulatory changes—and not the other way round—gains more and more support (McGinty et al. 2001, Gilbert et al. 2004). Thermoregulation is thought to play a role both in the initiation and consolidation of the human sleep function (see FIG. 19). However, the fact that ambient temperature not only affects sleep onset but also sleep architecture, plus the fact that sleep stages are known to interact with our thermoregulatory system, indicates that thermoregulation itself is also affected by the sleep process (Muzet et al. 1984, Libert et al. 1988, Muzet 2004).

Recently, Quanten et al (2006a and 2006b) showed that the increase in peripheral heat loss is not restricted to situations of non-active attempted sleep onset at natural bed times and natural sleep conditions, but that peripheral heat loss of the same magnitude also occurs in situations of NESAS. A significant difference between 5-min time frames of peripheral heat loss between sleepy and non sleepy drivers was statistically derived.

The thermoregulatory functions in relation to sleep can be measured by recording of Core Body Temperature (e.g. thermocouple under armpit) and measurement of the Distal-to-Proximal Gradient (DPG). DPG is the gradient between peripheral skin temperature (finger of toe) and proximal skin temperature (forehead, chest, stomach, thigh, . . . ) as defined by Krauchi et al. (1997c). However, peripheral skin blood flow and the resulting distal heat loss are mechanisms that the thermoregulatory systems employ to maintain at thermoneutrality. Since the surrounding thermal microenvironment can evoke such thermoregulatory responses, the importance of the microenvironment in peripheral heat loss based sleepiness detection is clear.

Bearing this in mind, the formula to calculate the Distal-to-Proximal Gradient (DPG) can therefore be easily expanded in order to integrate the dynamic course of the thermal microenvironment, and remains applicable for on-line use:

$$DPMG(t)=T_{finger}(t)-T_{forehead}(t)-T_{eq}(t)[°C.] \quad (5.1)$$

where $T_{finger}(t)$ is the fingertip skin temperature or the distal skin temperature, $T_{forehead}(t)$ is the forehead skin temperature or proximal skin temperature, $T_{eq}(t)$ is the equivalent temperature, t is the time step and DPMG(t) is the thermal microenvironmental corrected Distal-to-Proximal Gradient (DPG) (° C.) or the Distal-to-Proximal-to-Microenvironmental Gradient (DPMG).

However, the question is when is an increase in Distal-to-Proximal Gradient (DPG) (or Distal-to-Proximal-to-Microenvironmental Gradient (DPMG)) over time in a particular subject substantial enough to talk about driver sleepiness? Therefore, the dynamic time course of the Distal-to-Proximal Gradient (DPG) of the individuals experiencing driver sleepiness is evaluated. Table 5.2 summarizes the values of the mean Distal-to-Proximal Gradient (DPG) in each time window of 5 minutes and the encountered significant differences. From table 5.2 it can be deduced that the smallest significant increase in Distal-to-Proximal Gradient (DPG) between two 5-min time frames is the 2.40° C. temperature increase between the mean Distal-to-Proximal Gradient (DPG) from minutes 5 till 10 and the mean Distal-to-Proximal Gradient (DPG) from minutes 20 till 25. So an increase of at least 2.40° C. per 5 minutes or a mean increase of 0.48° C./min over a 5 minute period is the decisive element when evaluating the dynamic course of Distal-to-Proximal Gradient (DPG) (and hence Distal-to-Proximal-to-Microenvironmental Gradient (DPMG)) for the presence of sleepiness signs. Additionally, the increase in Distal-to-Proximal Gradient (DPG) needs to be lasting throughout more than at least 10 minutes after the 5 minute period of the initial increase.

TABLE 5.2

Mean DPG in each time bin, the mean DPG increase between two time bins and the time bins to which the considered time bin is found significantly different.

| | Time (5 minutes) | | | | |
|---|---|---|---|---|---|
| | $T_{0-5}$ | $T_{5-10}$ | $T_{10-15}$ | $T_{15-20}$ | $T_{20-25}$ |
| Mean DPG (° C.) | 0.079 | 1.96 | 3.22 | 3.74 | 4.36 |
| Mean DPG increase (° C.) | 0 | 1.88 | 3.14 | 3.66 | 4.28 |
| Significantly different to | $T_{10-15}$ $T_{15-20}$ $T_{20-25}$ | $T_{20-25}$ | $T_{0-5}$ | $T_{0-5}$ | $T_{0-5}$ $T_{5-10}$ |

In order to guarantee possible on-line application and processing of the eventual system, a simple and compact detection technique for such Distal-to-Proximal-to-Microenvironmental Gradient (DPMG) sleepiness signs is implemented. By using a technique based on dynamic auto regression (FIG. 20), it is possible to evaluate the dynamic course of Distal-to-Proximal-to-Microenvironmental Gradient (DPMG) per 5 minute temperature window, and to obtain the information needed regarding mean temperature increase (slope) and the durability of the temperature increase (intercept). The full line in FIG. 20 represents the measured Distal-to-Proximal-to-Microenvironmental Gradient (DPMG) and the dotted line represents the dynamic auto regression model for 5 minute time window of DPMG. Both the intercept and the slope per 5 minute time window—and their changes over different time windows—are indicative of the dynamic course of DPMG.

C. Biorhythm and Sleepiness/Arousal

Since a lot of information is at hand regarding habitual sleep-wake rhythm of the subjects enrolled in the study. And since exceptions on the normal day to day routine are reported through the pre-test questionnaires, the possibility arises to determine the signs of sleepiness or 'susceptibility to sleep' based on the individual and time-varying biorhythm. This susceptibility to sleep in the biorhythm is simply defined here as the additive interaction of the homeostatic (process S) and circadian component (process C) of the two process model of sleep regulation (Borbely, 1982; Daan et. al, 1984) as shown in FIG. 21. This additive interaction of both components S—C delivers a measure for the level or susceptibility for sleep based on information regarding the sleep/wake behaviour during the preceding days, the normal biorhythm and the time of day (FIG. 21). Other authors have also applied the continuous interaction of S—C to determine levels of sleepiness (e.g. Borbeley et al., 1989; Folkard et. al, 1991; (Achermann et. al, 1992; Folkard et. al, 1991). The time course of S—C evolves under normal conditions between two thresholds $H_m$ (0.67) and $L_m$ (0.17), where sleep is initiated at the moment that S—C exceeds the upper threshold $H_m$ and sleep is terminated when S—C fall below the lower threshold $L_m$. Throughout two-thirds of the waking episode, the two processes compensate each other, resulting in an approximately horizontal level of S—C. In the evening (or the time of normal sleep onset) a steep rise in the trajectory of S—C occurs indicating augmenting sleepiness.

Of course the prediction derived from this widely adopted model (and without considering other components like sleep inertia W) does not deliver an exact quantification of the tendency to fall asleep or the arousal state of the individual subjects, since it is established on a population level and it assumes a mean circadian rhythm throughout all test subjects. However, a relative comparison between susceptibility for sleep from the biorhythms under different situations for a subject (e.g. shift worker) can be obtained in simple and direct way, and the attractive simplicity of the model allows on-line calculation of this factor. Therefore, the S—C interaction term is employed as a bio-rhythm term, where a situation with a relative S—C level of over 66% of the sleep initiation threshold $H_{im}$ (or S—C>0.5) is considered as a sign of sleepiness in the biorhythm and hence to be dangerous (this 66% value corresponds to the final hour before normal bedtime). Think of it as a restriction to drive a vehicle one hour before the normal hour of sleep onset, or the avoiding of the risk of for instance truck drivers to abandon their normal bio-rhythm in order to make the delivery. It is shown that after 17 hours awake (i.e. 7 hours of sleep per night) the driving ability is similar to that with an alcohol intoxication of 0.5%. The value of this relative S—C level displaying the subject's biorhythm is updated every 5 minutes.

D. Driving Performance and Sleepiness/Arousal

Driving performance is in the present context merely considered as a correction term. If this variable—for any reason whatsoever—deteriorates to such an extent that a potential dangerous situation arises irrespective of the presence of sign of sleepiness, the driver can no longer be classified as safe. In these cases the unsafe situation is also classified as subject to driver sleepiness for safety reasons, although sleepiness might not be the cause for bad driving performance.

It needs mentioning that the applied thresholds for driver performance evaluation are extreme cases of drivers misperforming, and relate to situations where few doubts regarding the safety consequences exist, in part by the lack of consensus in literature on the subject.

Driving simulator performance is assessed by two variables, (1) lane drifting, the standard deviation of the road position in cm/m lane and (2) speed deviation, the mean deviation from the posted speed limit in km/h. Since it is inaccurate and unreliable to define a threshold for speed deviation and lane drifting based on merely a statistical analysis, the decision is made to introduce meaningful thresholds that relate to extreme impairment of driver's performance. Both the variables lane drifting and speed deviation are mediated over a time interval of 60 seconds. Within this 1 minute period, a mean lane deviation higher that 25 cm per meter lane is considered as dangerous enough to stop the driving. A deviation of 25 cm per meter lane means that the deviation of the vehicle from the ideal driving position (middle of the lane) at that moment is ¼ of the lane width. Bearing in mind that the vehicle itself comprises over ½ of the lane, the potential danger is clear. For speed deviation, a mean deviation over 1 minute of 25 km/h downward from the set point—driving less than 75 km/h where the instruction of the simulator clearly indicates driving at a mean speed of 100 km/h—is interpreted as a dangerous loss of interest/attention from the subjects. The driving performance correction variable is calculated every minute.

Performance and Validation of Driver Sleepiness Detection and Prediction Algorithm This section overviews the developed driver sleepiness detection algorithm, its performance on the controlled laboratory study, its validation on shift workers, and its predictive character.

D.1. Driver Sleepiness Monitor

The core of the algorithm evolves around the detection of signs of sleepiness/arousal from information encaptured in the (physiological) arousal component of heart rate and in biological responses of the driver's body to the microenvironment in which he or she drives the vehicle. The flowchart in FIG. 22 overviews the general composition of the driver sleepiness detection algorithm. It evolves around detection signs of sleepiness in a one-edged way. Alert drivers are not detected per se, but are merely considered as those drivers from whom no signs of sleepiness are detected.

The driver sleepiness detection algorithm is developed and its performance is tested on a controlled laboratory study and in a more elaborated and life-like date set of the shift workers study. In the controlled laboratory study, EEG recordings of the test subjects during their simulated drivers are at hand. In total, this study results in a data set of 18 simulator drives. In 13 out of the 18 simulator drives, the EEG recording clearly classifies the subject as experiencing driver sleepiness. The driver sleepiness algorithm only misclassified one sleepy driver as being non-sleepy, and misclassified two alert driver as being sleepy. The sensitivity of the algorithm on this limited data set is 92% with a specificity of 60%. It needs to be mentioned that misclassifying an alert driver as being subject to driver sleepiness is considered as a less grave mistake than the other way around. In the shift workers study, 54 complete data sets are at hand from which the sleepiness level could be clearly differentiated by means of the scientific validated Stanford Sleepiness Scale, which results in 26 sleepy drivers and 28 alert drivers. The 54 simulator drives from the shift workers study hence consist of situations of clear presence or absence of driver sleepiness, where very doubtful subjects had to be excluded since no reliable classification for those subjects could be achieved based on the Stanford Sleepiness Scale. This needs mentioning when situating the performance of the driver sleepiness detection algorithm. From both groups (sleepy and non-sleepy), only one simulated drive is misclassified adding up to sensitivity of 96% and a specificity of 96%.

When compiling both data sets (table 5.3), a considerable amount of 72 simulated drivers are available of which 93% (67) is correctly classified, divided over 95% correct classification of sleepy drivers (sensitivity) and 91% correctness in classifying the alert drivers (specificity).

TABLE 5.3

Driver sleepiness detection results on all the driver simulator tests.

| Type of subjects | Number of tests | Correct classified | Percentage correct |
|---|---|---|---|
| Drivers | 72 | 67 | 93% |
| Sleepy drivers | 39 | 37 | 95% |
| Sleepy crashes | 15 | 15 | 100% |
| Alert drivers | 33 | 30 | 91% |

Overall, the detection performance of the algorithm is quite high with a sensitivity of 95% and a specificity of 91% over 72 simulator drives.

D.2. Predictive Character of the Driver Sleepiness Monitor

The main ground for the integration of the arousal component of heart rate and biological responses on-line measured on the driver, is the possible predictive character that these variables might bring to a driver sleepiness detection algorithm. In order to investigate the predictive character of the driver sleepiness algorithm, the occurrence and timing of crashes is to be predicted. The driving simulator software enables detecting of the timing of a crash, and this is compared with the timing of the detection of signs of sleepiness by the developed algorithm.

FIG. 23 shows the predictive power of the driver sleepiness algorithm based on the arousal component of heart rate, bio-responses and microenvironmental information for one specific simulator driver. During the 25 minute simulator drive, the subject—scored as subject to driver sleepiness based on the Stanford Sleepiness Scale—crashes one time. However, already after 10 minutes of simulated driving, sign of driver sleepiness are present. This holds a prediction of the crash due to driver sleepiness of 5 minutes and 20 seconds. Table 5.4 overviews the predictive power of the driver sleepiness detection algorithm in the controlled laboratory study, the shift workers study and on both studies together. The number of crashes, the crashes detected at least at the time of occurrence, the crashes predicted before their actual occurrence, the mean prediction horizon of the predicted crashes and their standard deviation over the mean prediction horizon. Of all the 72 simulated drives, 39 are subject to driver sleepiness and 15 of them crash during driving. All crashes are detected by the algorithm, and 14 out of 15 crashes can be predicted over a mean prediction horizon of 396 seconds before the moment of impact (standard deviation on mean prediction horizon is 290 seconds). This holds that all crashes, except one, are predicted over 6 and a half minute before the actual moment of impact due to the information embedded in the driver's biological responses.

TABLE 5.4

Overview of predictive power of the driver sleepiness detection algorithm in the controlled laboratory study, the shift workers study and overall. Indication of number of crashes, detected crashes, predicted crashes, mean prediction horizon and standard deviation on the mean prediction horizon.

| Exp. study | Type of subjects | Number of tests | Correct detected | Predicted crashes | Mean prediction horizon [sec] | Standard deviation [sec] |
|---|---|---|---|---|---|---|
| Sleep lab | Sleepy drivers | 13 | 12 | \ | \ | \ |
| | Sleepy crashes | 3 | 3 | 3 | 310 | 250 |
| Shift workers | Sleepy drivers | 26 | 25 | \ | \ | \ |
| | Sleepy crashes | 12 | 12 | 11 | 401 | 314 |
| All simulated drives | Sleepy drivers | 39 | 37 | \ | \ | \ |
| | Sleepy crashes | 15 | 15 | 14 | 396 | 290 |

Example 6: Using Image Information in a CITD Model

Introduction

It is envisaged that a metabolism or performance related variable of the individual can be quantified (and thus used as a model input) by using image analysis. From images the activity of movement or motion of the body can be calculated.

The output as well can be measured by using image analysis. From the images body movements or motions and all other image information that quantifies the behaviour of the body can be calculated.

It is well recognised that muscle activity and body movement are not limited to the one necessary for mechanical activity. One of the most widely used variables to measure (physiological) arousal in a (resting) subject is muscle activity, which is most often assessed using an EMG. However, arousal is also present in non-resting subjects, even more so than in resting ones. To measure arousal in a moving individual human or animal, it is however necessary to be able to distinguish between movement strictly related to task performance and movement not related thereto, which can be attributed to arousal. Image analysis can be applied to this end. When for example somebody walks to the door, an image can show the displacement of the body and this is a measure for the energy required to move this body to the door. However, depending on the mental/arousal status this movement can be done in several ways, with more action than the one needed to move the body. These movements can be calculated from the images as well and contains information about the arousal of the individual.

Depending on what movement is assessed, the arousal can be attributed to different parameters. For instance, when assessing head movement of an individual human, facial expression (or changes therein) can be linked to the arousal of the individual. When assessing total body movement, the movement of limbs that is not required for task performance (e.g. getting from A to B) can be attributed to arousal. As mentioned before, this does not exclude the possibility that there is an arousal component present in the input (e.g. in the head movement or the movement from A to B), but this component is taken into account by the 'arousal feedback' of the model.

In this example, images are recorded of a human face with a camera in frontal view. Footage is used of the driving simulator experiment described in example 5 (see FIG. 24A). In each image, the positions of features points on the face are estimated using a face mask consisting of 51 feature points, placed on consistent locations (e.g. eye corners, eyebrows, nose, mouth, face outline), as shown in FIG. 24B.

Modelling

The process monitored in the camera images is a combination of 2 sub-processes. One is the measured response of the facial features to the behaviour of the individual and this relation can be modelled. The remainder is the fact that this response is not exactly the same every time the behaviour is performed. This last component is a response to arousal and can be related to the arousal or mental status of the individual.

The process of individual behaviour and its response in facial features can be described as follows (FIG. 25):

Process input: $u(t)$=displacement of the facial features due to the rigid facial movement (translation and rotation of the head as a non-deformable body)

Process output: $y(t)$=average displacement of the facial features due to the total facial movement (translation, rotation and facial expressions)

Model output: $\hat{y}(t)$=the expected process output as a relation to the process input, described by the model The model output ŷ will not fully match the process output y because it only describes the signal in the process output y that is directly related to the process input u. The remainder, ('residue' or difference), is a response to arousal and can be related to the arousal or mental state of the individual.

In FIG. 26, actual values of process input, process output, model output and the calculated difference (residue) are shown over time. The difference between process output and model output is depicted graphically in FIG. 27. This difference corresponds to the movement of the facial features, after the rigid head movement is eliminated. Thus, in practice, this is the movement caused by facial expression. Facial expression is considered here as the arousal component of head (or facial) movement.

FIG. 28 shows the feasibility of detecting facial expression changes by image analysis, by automatic detection of eye blinks. The value of the model residue is determined over time. Comparing this value with non-automatically detected eye blinks shows a clear correlation between the peaks in the value of the difference and the occurrence of eye blinking. From the dynamics of this value, the occurrence of eye blinking can be derived.

The concept of automatically studying facial expression (as the arousal component of head movement) can be implemented in a wide range of applications. For instance, it may be used in the detection of pain (particularly useful for monitoring individuals unable to communicate accurately, e.g. people with dementia).

Example 7 Using Whole Body Image Information in a CITD Model

As explained in the introduction of Example 6, an arousal component can also be derived from the total movement of an individual human or animal. In the present example, this is illustrated for the analysis of modelling the gait of a mouse.

This can be applied to a mouse as a laboratory animal where the gait analysis is an important tool in the development of medication. FIG. 29 shows the experimental setup where a camera (c) can register a video from the bottom of a mouse walking on a glass plate lighted with lamps (a). Video-images are stored in a computer (e). FIG. 30 shows the model that is applied. As input, measured speed from the video and labelled running of the mouse was used, from which the paw coordinates (over time) are predicted by the model. The paw coordinates are the coordinates of the paw in relation to the geometric centre of the mouse in each image, plotted as a function of time. The difference between the predicted paw movement from the model and the actual measured paw movement is the paw movement that is not directly related to the running, i.e. the paw movement that can be attributed to arousal. Here, as in the previous example, the information on body movement is obtained by image analysis. This technique is adapting in real time for each individual mouse.

Another example is the automatic detection of activities of a laying hen related to a specific status of arousal. FIG. 31 shows the top view pictures of a laying hen that can be collected at 25 images per second. By taking the picture and applying well known subject recognition algorithms, the subject area and contour can be calculated (see FIG. 31). Then a simple model, an ellipse, can be fitted over each image. This results in a moving ellipse changing with all actions of the chicken. From the ellipse one can calculate the rigid movement (speed) of the total body of the chicken. This is used as the metabolic related input variable since the laying hen will use energy to move the body. As a measured process output the total movement is measured with a similar image technique that includes information (see further in posture parameters) of the total activity of the laying hen.

It is well known by ethologists that scratching of a chicken or laying hen is strongly related to the specific status of being relaxed which is a specific arousal status. By using the model, the part of the total movement (process output) that is related to the metabolic related variable (process input) is estimated (model output) (FIG. 32). By subtracting this model output from the total measured process output the arousal activities not related to the rigid body movement is calculated.

From the different dynamic variations of the ellipse parameters (long and width axis) the different activities like for example "scratching" can be recognized when subtracting the model output from the total movement. In this way scratching can be recognized (FIG. 33). This shows how the presented methodology has potential in the field of automatic continuous monitoring of animal welfare.

"Posture Parameters" and "Dynamics Parameters"

As a measured process output the total movement is measured with a real time image technique. Mathematically an ellipse can be described by two parameters: the length and the width of the ellipse. We call them "posture parameters" since they vary when the hen is changing the posture while doing several activities. Indeed than the length of these two parameters with change as well. Not only the rigid body movement but also all actions and activities without moving the position of the rigid body are now measurable such as picking food, scratching, spreading the wings, eating, drinking. Each of these activities has a specific dynamic variation of the posture parameters (see FIG. 33). When now applying a second model to model the dynamic behaviour of the posture parameters, the parameters of this second model are dynamic parameters d1 to do (FIG. 33).

Each activity like for example scratching has a unique combination of the dynamic behaviour of the p1 and p2 parameters and this is quantified in the combination of the values of the d-parameters (FIGS. 31C and 33). In the mathematical space (a plane for 2 parameters) the combination of values of the dynamic parameters are grouped within a certain volume or box like for example the scratching box on FIG. 40.

By making determining the limits of this box first on a number of hens and calculating the limits later in real time for an individual it is possible to adapt the limits to an individual since the parameters are calculated in real time.

Another example is the status of arousal in cow due to the process of giving birth. Similar to the chicken in this example the cow is filmed by using a top view camera (FIG. 35). As process input we measure the x-y coordinates of the centre point of the image of the cow. The x-y coordinates will vary as a function of time and give information of the metabolic energy the cow is using to move the body. As a process output we measure with real time image analysis the width to length ratio. The width to length ratio will vary with the different activities the cow is performing such as laying and standing, moving posture, etc.

From the model we can estimate the part of output related with the movement of the rigid body. The difference (or "model error" with total measured process output) is a measure for all other activities in the output than the part related to rigid body motion. FIG. 36 shows a result of experiments on 78 cows where images were taken during delivery. For a cow in the process of delivery these activities are strongly related to the arousal due to the delivery process. In this way a calving monitor can be developed as an example of continuous automatic measurement of arousal.

Example 8: Model-Based Detection of Emotion in Sound

Objective

The objective of this research was to investigate if it is possible to decompose the sound signal of an animal into a part that is related to normal locomotor activity and a part that is related to arousal based on a model describing the relation between the output sound production and the input animal activity (see FIG. 37).

Methods

1) Experiment

The objective of the experiment was to measure the sound production of a stallion during normal walking as well as in the presence of a mare (arousal). At the beginning of the experiment, the stallion was walking in his box while the mare was not in the neighbourhood. After 53 seconds of recording, the stallion heard the mare approaching. After 70 seconds, the stallion was facing the mare until second 355. After 355 seconds of recording the mare was led away from the stallion. The reported experimented lasted in total 387 seconds.

2) Measured Signals

The activity and sound production of a stallion was measured with and without a mare in the neighbourhood. Activity was measured with a 3D accelerometer at a sample rate of 40 Hz. The activity was calculated as the square root of the sum of the squared individual acceleration components (x-, y- and z-direction). Sound was recorded with a microphone at a sampling rate of 32 kHz. Sound intensity was calculated by squaring the raw sound signal. The sound signal was resampled to a frequency of 1 Hz. The activity signal (40 Hz) was reduced to a frequency of 1 Hz by summing up the signal in blocks of 40 seconds. As a result, every data point represents the sum of the previous 40 samples. The signals as used for the modelling are shown in FIG. 38 and FIG. 39.

3) Modelling

Based on the measured activity and sound production of the first 60 seconds, a second order transfer function was estimated by using a recursive instrumental variable method (Young, 1984). The resulting model structure looked as follows:

$$y(k) = \frac{b_1 z^{-1} + b_2 z^{-2}}{1 + a_1 z^{-1} + a_2 z^{-2}} u(k)$$

with $y(k)$ is the sound intensity; $u(k)$ is the activity; $a_i$ and $b_j$ are the model parameters; $k$ is the discrete time instant; $z^{-1}$ is the backward shift operator ($z^{-1}y(k)=y(k-1)$).

The estimated model parameters were: $a_1=-0.9421$; $a_2=0.5570$; $b_1=-0.0012$; $b_2=0.0046$. (The time delay was 1).

The model, describing the sound production response to the activity of the horse under normal conditions (no excitation by the mare), was used to simulate the entire sound production time series (with and without the mare).

Results

The modelled sound production was compared with the measured sound production and the errors between model and measurements were calculated. In FIG. 40 it can be seen that the sound production of the stallion can be modelled with a small error when the mare is not in the neighbourhood (first 53 seconds and after second 355). When the stallion hears, smells and/or sees the mare, the modelled sound production of the stallion does not match any more with the measured sound production, indicating emotional components that are not described by the model (between seconds 54 and 355). This was quantified as the model errors passing a threshold value. In this example, the threshold was set to ±0.015. These values were calculated as the maximum difference between the modelled and measured sound intensity during the first 50 seconds (period when the mare not present). In this way, a model was used to decompose sound of the horse in a locomotion and an emotion related part.

REFERENCES

Abrahamsson, P. 1996. Furnished cages and aviaries for laying hens: effects on production, health and use of facilities. Swedish University of Agricultural Sciences. Upsala. Department of Animal Nutrition and Management. Report 234.

Achermann, P. and Borbeley, A. A., 1992. Combining various models of sleep regulation. Journal of sleep research, 1, p. 144-147.

Aerts J.-M., Buyse J., Decuypere E., Berckmans, D., 2003a. Order identification of the dynamic heat production response of broiler chickens to steps in temperature and light intensity. Trans. ASAE 46(2), 467-473.

Aerts J.-M., Van Buggenhout S., Lippens M., Buyse J., Decuypere E., Vranken E., Berckmans, D., 2003b. Active control of the growth trajectory of broiler chickens based on on-line animal responses. Poultry Sci. 82(12), 1853-1862.

Anderson J C, Linden W, Habra M E. The importance of examining blood pressure reactivity and recovery in anger provocation research. Int J Psychophysiol. 2005; 57(3): 159-63.

Anttonen J, Surakka, V. Emotions and heart rate while sitting on a chair. Proceedings of CHI 2005: Affect and Intimacy, April 2-7, Portland, Oreg., USA, p. 491-499, 2005.

Berckmans, D., De Moor, M., and De Moor, B., 1992, New model concept to control the energy and mass transfer in a three-dimensional imperfectly mixed ventilated space, Air distribution in rooms. 3. international conference on air distribution in rooms: air movement in large spaces, Aalborg (Denmark), p. 151-16.

Boonen C, on-line measurement and modelling of dynamic plant responses to variations of the microenvironment, PhD thesis nr. 641 at the faculty of Bioscience Engineering, K.U.leuven, pp. 115, T.

Borbely, A. A., 1982. A two-process model of sleep regulation. Human Neurobiology, 13, p. 417-42.

Borbely, A A, Achermann, P., Trachsel, L., Tobler, I., 1989, Sleep Initiation and Initial Sleep Intensity-Interactions of Homeostatic and Circadian Mechanisms: Journal of Biological Rhythms, 4, p. 149-160.

Brosschot & Thayer (2003) J. F. Brosschot and J. F. Thayer, Heart rate is longer after negative emotions than after positive emotions, International Journal of Psychophysiology 50 (2003), pp. 181-18.

Brown, C. C. Toe temperature change: a measure of sleep onset? Waking Sleeping, 1979, 3: 353-359.

Burbridge J A, Larsen R J, Barch D M, 2005. Affective reactivity in language: The role of psychophysiological arousal, Emotion 5 (2): 145-15.

Camacho E. F., and Bordons C. 1999. Model predictive control. Berlin: Springer-Verlag.

Clarenbach, P, Greulich, W. (2000) Parkinson's disease and sleep—results of the group discussion. Journal of Neurology, 247, Suppl 4, IV/34-.

Collins, K. J., Abdel-Rahman, T. A., Goodwin, J., and McTiffin, L., 1995. Circadian body temperature and the effect of cold stress in elderly and young people. Age Ageing, 24, p. 485-489.

Cowings P S, Kellar M A, Folen R A, Toscano W B, Burge J D. Autogenic Feedback Training Exercise and pilot performance: enhanced functioning under search-and-rescue flying conditions. Int J Aviat Psychol. 2001; 11(3): 303-15.

Csete, M. and Doyle, J. C., 2002. Reverse Engineering of Biological Complexity. Science, 295, p. 1664-1668.

Czeisler, C. A., Weitzman, E. D., Moore-Ede, M. C., Zimmerman, J. C. and Knauer, R. S. Human sleep: its duration and organization depends on its circadian phase. 1980; 210, p. 1264-1267.

Daan, S., Beersma, D. G. M., and Borbely, A A., 1984. Timing of human sleep: recovery process gated by a circadian pacemaker. American Journal of Physiology, 246, (2 pt.2), p. R161-R18.

De Valck, E., Cluydts, R. & Pirrera, S. (2004) Effect of cognitive arousal on sleep latency, somatic and cortical arousal following partial sleep deprivation. Journal of Sleep Research, in press.

De Valck, E., 2004. Identification and assessment of the contributing factors to daytime sleepiness. Vrij Universiteit Brussel, PhD thesis at the faculty of psychology and physiological psychology, pp. 22.

De Waard, D. & Brookhuis, K. A. (1991). Assessing driver status: a demonstration experiment on the road. Accident Analysis and Prevention, 23, 297-307.

Dijk, D. J. and Czeisler, C. A., 1995. Contribution of the circadian pace-maker and the sleep homeostat to sleep propensity, sleep structure and electroencephalographic slow waves and sleep spindle activity in humans. Journal of Neuroscience, 15, p. 3562-3538.

Folkard, S. and Akerstedt, T., 1991. A three process model of sleep regulation of alertness and sleepiness. In: Ogilvie, Broughton, eds. Sleep, arousal, and performance: problems and promises. Boston, Brikhauser, p. 11-26.

Gilbert, S. S., Van den Heuvel, C. J, Ferguson, S. A., Dawson, D. (2004), Thermoregulation as a sleep signalling system, Sleep Medicine Reviews, 8, 81-93.

Golten and Verwer (1991). Control system Design and Simulation, McGraw-H ill.

Goodwin and Sin, 1984 G. C. Goodwin and K. S. Sin, Adaptive filtering prediction and control, Prentice-Hall, Englewood Cliffs, N J (1984).

Hales, J. R. Skin arteriovenous anastomoses, their controle nad role in thermoregulation. 1985: 233-245.

Hartwell, L. H., Hopfield, J. J., Leibler, S., and Murray, A. W., 1999. From molecular to modular cell biology. Nature, 402, p. C47-052.

Hood, L., Heath, J. R., Phelps, M. E. and B. Y. Lin. 2004. Systems biology and new technologies enable predictive and preventative medicine. Science 306:640-643.

Horne, J. A. & Baulk, S. D. Awareness of sleepiness when driving. Psychophysiology, 2004, 41: 161-165.

Kanda, K., Tochihara, Y., and Ohnaka, T., 1999. bathing before sleep in the young and the elderly. European Journal of applied physiology and occupational physiology, 80 (2), p. 71-75.

Kitano, H., 2002. Computational Systems Biology. Nature, 420 (6912), p. 206-210.

Kleitman, R., Ramsaroop, A., and Engelmannn, T., 1948. Variations in skin temperature of the feet and hands and the onset of sleep. Federations Proceedings, 7, pp. 66.

Kräuchi, K. and Wirz-Justice, A. Circadian rhythm of heat production, heart rate, and skin and core temperature under masking conditions in men. Am. J. Physiol., 1994, 267: R819-R829.

Kräuchi, K., Cajochen, C., Werth, E. and Wirz-Justice, A. Warm feet promote the rapid onset of sleep. Nature, 1999, 401: 36-37.

Kräuchi, K., Cajochen, C., Werth, E. and Wirz-Justice, A. Functional link between distal vasodilatation and sleep-onset latency? Am. J. Physiol., 2000, 278: R741-R748.

Kräuchi, K., Cajochen, C. and Wirz-Justice, A. A relationship between heat loss and sleepiness: Effects of a postural change and melatonin administration. J. Appl. Physiol., 1997c, 83: 134-139.

Krauchi, K. and Wirz-Justice, A., 2001. Circadian clues to sleep onset mechanism. Neuropsychopharmacology, 25 (Suppl. 5), pp. S95-S96.

Krauchi, K., Cajochen, C., Mori, D., Graw, P., and Wirz-Justice, A., 1997b. Early evening melatonin and S-20098 advance circadian phase and nocturnal regulation of core body temperature. American Journal of Physiology, 272, p. R1178-1188.

Kubo, H., Yanase, T., and Akagi, H., 1999. Sleep stage and skin temperature regulation during night-sleep in winter. Psychiatry Clinical Neuroscience, 53, p. 121-123.

Lack, L. and Gradisar, M. Acute finger temperature changes predict sleep onset over a 45-h period. 2002; 11, (4): 275-282.

Libert, J. P., Di Nisi, J. D., Fukuda, H., Muzet, J., Ehrhart, J., and Amoros, C., 1988. Effect of continuous heat exposure on sleep stages in humans. Sleep, 11, (2), p. 195-209.

Ljung, 1987. System Identification: theory for the user, p. 303-304, New Jersey: Prentice Hall.

Lushington, K., dawson, D., and Lack, L., 2000. Core body temperature is elevated during constant wakefulness is elderly poor sleepers. Sleep, 23, (4), p. 504-510.

Magnussen, G., 1943. On narcolepsy II. Studies on diurnal variations in the skin temperatures in narcoleptics. Acta Psychiatr Neurol, 18, p. 457-485.

McAdams, H. H. and Sharipo, L., 1995. Circuit Simulation of Genetic Networks. Science, 269, p. 650-656.

Mcginty, D. and Szymusiak, R., 2001. Brain Structures and Mechanisms Involved in the Generation of Nrem Sleep: Focus on the Preoptic Hypothalamus, 5 (4), p. 323-342.

Moody, J., 1992. ECG-based indices of physical activity. Computers in cardiology, p. 403-406.

Morris, M., Lack, L., and Dawson, D., 1990. Sleep-onset insomniacs have delayed temperature rhythms. Sleep, 13 (1), p. 1-14.

Muzet, A., 2004. Does the physical environment interact with the sleep process? Guest editorial for Sleep Medicine Reviews, 8, p. 77-79.

Muzet, A., Libert, J. P., and Candas, V., 1984. Ambient-Temperature and Human Sleep. Experientia, 40 (5), p. 425-429.

Myrtek, M., Fichtler, A., Strittmatter, M., and Brugner, G., 1999. Stress and strain of blue and white collar workers during leisure time: results of psychophysiological and behavioural monitoring. Applied ergonomics, 30, p. 341-351.
Pache, M., Krauchi, K., Cajochen, C., Wirz-Justice, A., Dubler, B., and Flammer, J., 2001. Cold feet and prolonged sleep-onset latency in vasopastic syndrome. Lancet, 358 (9276), p. 125-126.
Pennisi, E. Systems Biology: Tracing Life's Circuitry. Science 302, 1646. 2003 Quanten, S., 2005. Integration of on-line bio-response signals for process monitoring and control in transportation systems, PhD thesis nr. 679 at the faculty of Bioscience Engineering, K.U.leuven, pp. 135.
Quanten, S., De Valck, E., Cluydts, R., Aerts, J.-M., and Berckmans, D., 2006. Individualized and time-variant model for the functional link between thermoregulation and sleep onset. Journal of Sleep Research, 15 (2), p. 183-198, SCI 3.400.
Quanten, S., De Valck, E., Cluydts, R., Aerts, J.-M., and Berckmans, D., 2006. Thermoregulatory changes at driver sleepiness. International Journal of Vehicle Design Special Issue on "Driver Comfort & Safety: measurements on vehicle drivers", 42 (½), p. 87-100, SCI 0.340.
Reyner, L. A. & Horne, J. A. Falling asleep whilst driving: are drivers aware of prior sleepiness? International Journal of Legal Medicine, 1998, 111: 120-123.
Rubinstein, E. H. and Sessler, D. I. Skin-temperature gradients correlate with fingertip blood flow in humans. 1990; 73, 541-545.
Sangal, R. B., Thomas, L. and Mitler, M. M. Maintenance of wakefulness test and multiple sleep latency test: measurement of different abilities in patients with sleep disorders. Chest, 1992, 101: 898-902.
Soeterboek A. R. M. 1992. Predictive control. A unified approach. New York: Prentice Hall.
Sung, E. J. and Tochihara, Y., 2000. Effects of bathing and hot footbath on sleep in winter. Journal of Physiol Anthropol Appl Human Science, 19 (1), p. 21-27.
Tomlin, C. J. and Axelrod, J. D., 2005. Understanding biology by reverse engineering the control. Proceedings of the National Academy of sciences of the united states of America, 102 (12), p. 4219-4220.
Van den Heuvel, C. J., Ferguson, S. A., Dawson, D., Gilbert, S. S., 2003. Comparison of digital infrared thermal imaging (DITI) with contact thermometry: pilot data from a sleep research laboratory. Physiological Measurement, 24 (3), 717-725.
Van Someren, E. J. W., 2000. More than a marker/interaction between the circadian regulation of temperature and sleep, age related changes and treatment possibilities. Chronobiology international, 17 (3), p. 313-354.
Weitzman, E. D., Moline, M. L., Czeisler, C. A., and Zimmerman, J. C., 1982. Chronobiology of aging: temperature, sleep-wake rhythms and entrainment. Neurobiol Ageing, 3 (4), p. 299-309.
Robert M. Yerkes and John D. Dodson (1908) The relation of strength of stimulus to rapidity of habit-formation, Journal of Comparative Neurology and Psychology, 18, 459-482.
Young P C (1984). Recursive estimation and time series analysis: an introduction. Springer-Verlag. Berlin.
Young, P. C. and Jakeman, A. J., 1979. Refined instrumental variable methods of recursive time-series analysis: part II, single input output systems. International Journal of Control, 30, p. 1-30.
Young, P. C. and Wallis, S. G. Solute transport and dispersion in channels. Beven, K. J. and Kirkby, M. J. Channel Networks. 129-173. 93. Chichester, UK., J. Wiley.
Zulley, J., Wever, R., and Aschoff, J., 1981. The independence of onset and duration of sleep on the circadian rhythm of rectal temperature. Pflugers Arch, 391, p. 314-318.

The invention claimed is:
1. A method of monitoring an estimation of an arousal component of a heart rate ($HR_{PhAr}$) of an individual human or animal on the basis of a model capable of integrating measured, real-time information on one or more bioprocess inputs and one or more bioprocess outputs and linking the information to the estimation of the arousal component of the heart rate of the individual human or animal ($HR_{PhAr}$), the heart rate having a physical component ($HR_{phys}$) and the arousal component ($HR_{PhAr}$), the method being executed in a computer under the control of a program stored in the computer and comprising:
using at least one sensor for measuring real-time information on bioprocess inputs and/or bioprocess outputs,
generating the model on-line,
inputting, to the model, the real-time information on bioprocesses of the human or animal,
generating, responsive to the input real-time information, model outputs using a dynamic and adaptive data-based on-line modelling technique, wherein at least one of the bioprocess inputs or outputs used as model input is a metabolism-related variable relating to the metabolic energy and/or mobilized energy of the human or animal, which is a measurable factor affecting the bioprocess, and at least one of the model outputs is an estimated component of the heart rate ($HR_{mech}$) based on at least the one metabolism-related variable relating to the metabolic energy and/or mobilized energy, and wherein the model is updated on-line by adapting parameters of the model in real-time based on estimating and predicting the model outputs and comparing the model outputs in real-time with measured bioprocess outputs,
measuring in real-time the measured heart rate of the individual human or animal ($HR_{tot}$),
outputting information about the measured heart rate ($HR_{tot}$) to an output component, and
using the information about the heart rate ($HR_{tot}$) to control said physical component ($HR_{phys}$) or said arousal component ($HR_{PhAr}$), by adapting at least one of the bioprocess inputs and/or an environmental variable changing a relationship between the bioprocess input and the bioprocess output,
determining a value for an unknown variable attributed to the estimation of the arousal component ($HR_{PhAr}$) from a set of equations, wherein at least the heart rate ($HR_{tot}$) and the estimated component of the heart rate ($HR_{mech}$) are known variables, and
using the value of the unknown variable to monitor and/or control the arousal component of the heart rate ($HR_{PhAr}$),
wherein a component of the heart rate relating to basal metabolism ($HR_{bmr}$) and a component of the heart rate relating to heat balance ($HR_{heat}$) are additional known variables in the set of equations,
wherein the estimation of the arousal component ($HR_{PhAr}$) is determined by subtracting in real-time (a) the component of the heart rate relating to basal metabolism ($HR_{bmr}$) and the component of the heart rate relating to heat balance ($HR_{heat}$) from (b) the difference between the real-time measured heart rate ($HR_{tot}$) and a mechanical activity component, the mechanical activity component being the estimated component of the heart rate ($HR_{mech}$), wherein the resulting difference between (b) and (a) is the value of the unknown variable attributed to the estimation of the arousal component ($HR_{PhAr}$), wherein generating the model on-line includes expressing the real-time measured heart rate as $$y(t) = \frac{B(q)}{F(q)}u(t-nk) + \frac{C(q)}{D(q)}e(t)$$

in which the mechanical activity component, being the estimated component of the heart rate ($HR_{mech}$) with a time delay nk, the component of the heart rate relating to basal metabolism ($HR_{bmr}$) and the component of the heart rate relating to heat balance ($HR_{heat}$), are the physical component ($HR_{phys}$) expressed as $$\frac{B(q)}{F(q)}u(t-nk)$$

and in which the error is the difference between the real-time measured heart rate ($HR_{tot}$) and the physical component of the heart rate ($HR_{phys}$) expressed as $$\frac{C(q)}{D(q)}e(t)$$

wherein y(t) is a time series of a measured bioprocess output being the real-time measured heart rate ($HR_{tot}$);

t is time;

u(t−nk) is a time series of a measured bioprocess input being the physical activity used as model input;

nk is a time delay between the bioprocess input and the bioprocess output;

e(t) is a dynamic error term describing the unknown variable attributed to the estimation of the arousal component of the heart rate ($HR_{PhAr}$);

B(q), F(q), C(q) and D(q) are polynomials including model parameters that are adapted for updating the model based on estimating and predicting the model outputs and comparing the latter with measured bioprocess outputs; and q is a backward shift operator.

2. The method according to claim 1, further comprising the steps of:

using the value of the unknown variable as a model input in an additional model or algorithm for monitoring or controlling purposes, and generating a second unknown variable, and using the second unknown variable as additional model input in the additional model or algorithm for monitoring or controlling purposes.

3. The method according to claim 2, wherein the model output of the additional model or algorithm is used for the continuous detection of normal to excessive sleepiness in an active subject (NESAS).

4. The method according to claim 1, wherein the value of the unknown variable is determined over time, resulting in dynamics of the unknown variable, and the value of the unknown variable is classified as containing arousal events or not, depending on the dynamics of the unknown variable.

5. The method according to claim 4, wherein the arousal events are further classified as contributing to positive, neutral or negative arousal depending on the dynamics of the unknown variable.

6. The method according to claim 1, further comprising the step of using the estimated component of the heart rate to monitor and/or control the physical component of the heart rate.

7. The method according to claim 6, further comprising taking into account, in addition to the estimated component of the heart rate based on the at least one metabolism related variable, the component of the heart rate relating to basal metabolism and the component of the heart rate relating to heat balance, to monitor and/or control the physical component of the heart rate.

8. The method according to claim 6, wherein the dynamics of the model parameters modelling the physical status of the individual are used to detect whether the individual has taken or been administered doping.

9. The method according to claim 1, wherein the animal is mammalian or avian or a horse, cow, chicken or a human.

10. The method according to claim 1, wherein the metabolism related variable is selected from training activity, body movement or body part movement, and power production.

11. The method according to claim 1, wherein the model takes into account effects of external disturbances or variables considered as external disturbances to redefine the relation between bioprocess inputs and bioprocess outputs.

12. The method of claim 1, wherein the control of said at least one variable of said physical component or said arousal component increases efficiency of an activity of said human or animal.

13. The method of claim 12, wherein said activity is training activity, body movement or body part movement, or power production.

14. The method of claim 13, wherein said training activity is athletic training.

15. The method of claim 1, wherein the output component is a display, an alarm device, and/or a machine used by the human or animal.

16. The method according to claim 1, wherein physical related model parameters concerning the mechanical activity component, being the estimated component of the heart rate, are estimated on a clear physical effort when a physical heart rate response is dominant, and wherein the unknown variable is determined and attributed to the arousal component of the heart rate while the physical related model parameters are kept constant.

17. The method according to claim 1, further comprising the step of using the value of the unknown variable as a model input in an additional model or algorithm for monitoring or controlling purposes.

18. The method according to claim 1, further comprising the step of generating a second unknown variable, and using the second unknown variable as additional model input in the additional model or algorithm for monitoring or controlling purposes.

19. The method according to claim 1, further comprising the step of classifying the measured heart rate, being the bioprocess output, as containing arousal events when dynamics is detected in the measured heart rate without a corresponding dynamics in the metabolism-related variable relating to the metabolic energy and/or mobilized energy of the human or animal, being the bioprocess input.

20. A system for monitoring an estimation of an arousal component of a heart rate of an active individual human or animal ($HR_{PhAr}$), the heart rate ($HR_{tot}$) having a physical ($HR_{phys}$) and the arousal component ($HR_{PhAr}$), comprising
(a) at least one sensor for measuring real-time information regarding bioprocess inputs and bioprocess outputs, wherein at least one of the bioprocess inputs or outputs is a variable relating to the metabolic energy and/or mobilized energy of the human or animal, which is a measurable factor affecting the bioprocess;
(b) measured real-time information;
(c) a first processor connected to communicate with the first device for on-line modelling and generating an estimated component of the heart rate of the human or animal ($HR_{mech}$), based on at least the variable relating to the metabolic energy and/or mobilized energy, said first processor further configured and operable to on-line adapt model parameters in real-time, based on estimating and predicting model outputs and comparing the predicted model outputs in real-time with the measured bioprocess outputs; and
an output component operably coupled to the first device, that prompts a change in a status of the human or animal by adapting at least one of the bioprocess inputs and/or an environmental variable changing a relationship between the bioprocess input and the bioprocess output, wherein the estimation of the arousal component ($HR_{PhAh}$) is determined by subtracting (i) a component of the heart rate relating to basal metabolism ($HR_{bmr}$) and a component of the heart rate relating to heat balance ($HR_{heat}$) from (ii) the difference between the heart rate ($HR_{tot}$) and a mechanical activity component, the mechanical activity component being the estimated component of the heart rate ($HR_{mech}$), wherein the resulting difference between (ii) and (i) is the estimation of the arousal component ($HR_{PhAr}$),
wherein the first device and the first processor are adapted to use a model in which the real-time measured heart rate ($HR_{tot}$) is expressed as $$y(t) = \frac{B(q)}{F(q)} u(t-nk) + \frac{C(q)}{D(q)} e(t)$$

in which the mechanical activity component, being the estimated component of the heart rate ($HR_{mech}$) with a time delay nk, the component of the heart rate relating to basal metabolism ($HR_{bmr}$) and the component of the heart rate relating to heat balance ($HR_{heat}$), are the physical component ($HR_{phys}$) expressed as $$\frac{B(q)}{F(q)} u(t-nk)$$

and in which the error is the difference between the real-time measured heart rate ($HR_{tot}$) and the physical component of the heart rate ($HR_{phys}$) expressed as $$\frac{C(q)}{D(q)} e(t)$$

wherein
y(t) is a time series of a measured bioprocess output being the real-time measured heart rate ($HR_{tot}$);
t is time;
u(t−nk) is a time series of a measured bioprocess input being the physical activity used as model input;
nk is a time delay between the bioprocess input and the bioprocess output;
e(t) is a dynamic error term describing the unknown variable attributed to the estimation of the arousal component of the heart rate ($HR_{PhAr}$),
B(q), F(q), C(q) and D(q) are polynomials including model parameters that are adapted for updating the model based on estimating and predicting the model outputs and comparing the latter with measured bioprocess outputs; and
q is a backward shift operator.

21. The system of claim 20, further comprising:
(d) a second processor configured and operable to communicate with the first device for on-line modelling and generating the value of an unknown variable from a set of equations wherein the measured heart rate ($HR_{tot}$) and the estimated component of the heart rate ($HR_{mech}$) 1 are known variables.

22. The system of claim 21 for controlling the heart rate, further comprising:
(e) a first computational module for comparing and determining a variance between the estimated component of the heart rate ($HR_{mech}$) land a preset reference physical component of the heart rate;
(f) a second computational module for comparing and determining a variance between the generated value of the unknown variable and a preset reference arousal component;
(g) controller to determine how one or more bioprocess inputs should be adjusted in relationship to the variance determined by at least one of the first and second computational modules.

23. The system of claim 21, further comprising a computational module for on-line modelling and predicting a bio response based on the input of at least the value of the unknown variable.

24. The system according to claim 21, wherein the second processor is configured and operable to use the value of an unknown variable to monitor and/or control the arousal component of the heart rate, wherein a component of the heart rate relating to basal metabolism and a component of the heart rate relating to heat balance are additional known variables in the set of equations.

25. The system of claim 20, wherein the variable relating to the metabolic energy and/or mobilized energy the metabolism related variable is selected from the group consisting of training activity, body movement or body part movement, and power production.

26. The system of claim 25, wherein said activity is athletic training.

27. The system of claim 20, wherein the control of said at least one variable of said physical component or said arousal component increases efficiency of an activity of said human or animal.

28. The system of claim 20, wherein the first device comprises a sensor or electrode.

29. The system of claim 20, wherein said first device is a personal computer, a PDA, a smart phone, or a global positioning system (GPS) device.

30. The system of claim 20, wherein the first processor is in wired or wireless communication with the first device.

31. The system of claim 20, wherein the output component is a display, an alarm device, or a machine used by human or animal.

32. The system of claim 20, wherein the first processor is configured and operable to:
to estimate physical related model parameters concerning the mechanical activity component, being the estimated component of the heart rate, on a clear physical effort when physical heart rate response is dominant and to determine the unknown variable and attribute it to the arousal component of the heart rate while the physical related model parameters are kept constant.

33. The system of claim 20, wherein the first processor is configured and operable to: classify the measured heart rate, being the bioprocess output, as containing arousal events when dynamics is detected in the measured heart rate without a corresponding dynamics in the metabolism-related variable relating to the metabolic energy and/or mobilized energy of the human or animal, being the bioprocess input.

34. A computer program product, tangibly embodied in a non-transitory machine-readable medium for execution by a processor, the computer program product being operable to cause data processing for use in a system for monitoring an estimation of an arousal component of heart rate of an individual human or animal, the heart rate ($HR_{tot}$) having a physical component ($HR_{phys}$) and the arousal component ($HR_{PhAr}$),
the computer program comprising software code which when executed on a processing engine having a processor and memory provides:
(a) software code for collecting and storing real-time information on bioprocess inputs and outputs, wherein at least one of the bioprocess inputs is a variable relating to the metabolic energy and/or mobilized energy of the human or animal, which is a measurable factor affecting the bioprocess; and
(b) software code for on-line modelling and generating an estimation of a component of the heart rate of the human or animal ($HR_{mech}$), based on the variable relating to the metabolic energy and/or mobilized energy,
the computer program product being adapted to estimate the arousal component ($HR_{PhAr}$) by subtracting the estimated component of the heart rate ($HR_{mech}$), the component of the heart rate relating to basal metabolism ($HR_{bmr}$) and the component of the heart rate relating to heat balance ($HR_{heat}$) from the measured heart rate ($HR_{tot}$) and the resulting difference is a value of an unknown variable attributed to the arousal component of the heart rate ($HR_{PhAr}$)
wherein the computer program further comprises a model in which the real-time measured heart rate ($HR_{tot}$) is expressed as $$y(t) = \frac{B(q)}{F(q)} u(t-nk) + \frac{C(q)}{D(q)} e(t)$$

in which the mechanical activity component, being the estimated component of the heart rate ($HR_{mech}$) with a time delay nk, the component of the heart rate relating to basal metabolism ($HR_{bmr}$) and the component of the heart rate relating to heat balance ($HR_{heat}$), are the physical component ($HR_{phys}$) expressed as $$\frac{B(q)}{F(q)} u(t-nk)$$

and in which the error is the difference between the real-time measured heart rate ($HR_{tot}$) and the physical component of the heart rate ($HR_{phys}$) expressed as $$\frac{C(q)}{D(q)} e(t)$$

wherein
y(t) is a time series of a measured bioprocess output being the real-time measured heart rate ($HR_{tot}$);
t is time;
u(t−nk) is a time series of a measured bioprocess input being the physical activity used as model input;
nk is a time delay between the bioprocess input and the bioprocess output;
e(t) is a dynamic error term describing the unknown variable attributed to the estimation of the arousal component of the heart rate ($HR_{PhAr}$);
B(q), F(q), C(q) and D(q) are polynomials including model parameters that are adapted for updating the model based on estimating and predicting the model outputs and comparing the latter with measured bioprocess outputs; and
q is a backward shift operator.

* * * * *